(12) United States Patent
Kreft et al.

(10) Patent No.: US 7,547,725 B2
(45) Date of Patent: Jun. 16, 2009

(54) FLUORO- AND TRIFLUOROALKYL-CONTAINING HETEROCYCLIC SULFONAMIDE INHIBITORS OF BETA AMYLOID PRODUCTION AND DERIVATIVES THEREOF

(75) Inventors: Anthony Frank Kreft, Langhorne, PA (US); Lynn Resnick, Parlin, NJ (US); Scott Christian Mayer, Bridgewater, NJ (US); George Diamantidis, Randolph, NJ (US); Derek Cecil Cole, New City, NY (US); Boyd Lynn Harrison, Princeton Junction, NJ (US); Minsheng Zhang, Warren, NJ (US); Molly Hoke, Hightstown, NJ (US); Tingzhong Wang, Pomona, NY (US); Rocco John Galante, Oakland, NJ (US)

(73) Assignee: Wyeth, Madison, NJ (US)

( * ) Notice: Subject to any disclaimer, the term of this patent is extended or adjusted under 35 U.S.C. 154(b) by 105 days.

(21) Appl. No.: 11/818,630

(22) Filed: Jun. 15, 2007

(65) Prior Publication Data

US 2007/0254929 A1 Nov. 1, 2007

Related U.S. Application Data

(63) Continuation of application No. 10/810,517, filed on Mar. 26, 2004, now Pat. No. 7,300,951.

(60) Provisional application No. 60/459,228, filed on Mar. 31, 2003.

(51) Int. Cl.
  *A61K 31/381* (2006.01)
  *C07D 333/10* (2006.01)
  *C07D 333/34* (2006.01)

(52) U.S. Cl. .......................... 514/445; 549/29; 549/62; 549/65; 514/438

(58) Field of Classification Search .................. 549/29, 549/62, 65; 514/438, 445
See application file for complete search history.

(56) References Cited

U.S. PATENT DOCUMENTS

| | | | |
|---|---|---|---|
| 5,464,853 A | 11/1995 | Chan et al. | |
| 5,514,691 A | 5/1996 | Chan et al. | |
| 5,571,821 A | 11/1996 | Chan et al. | |
| 5,591,761 A | 1/1997 | Chan et al. | |
| 5,593,846 A | 1/1997 | Schenk | |
| 5,594,021 A | 1/1997 | Chan et al. | |
| 5,624,937 A | 4/1997 | Reel | |
| 5,703,129 A | 12/1997 | Felsenstein | |
| 5,852,007 A | 12/1998 | Chatterjee | |
| 5,981,168 A | 11/1999 | Reiner | |
| 6,248,775 B1 | 6/2001 | Vasquez | |
| 6,376,523 B1 | 4/2002 | Chan et al. | |
| 6,566,536 B2 | 5/2003 | Muller et al. | |
| 6,610,734 B2 | 8/2003 | Kreft et al. | |
| 6,657,070 B2 | 12/2003 | Resnick | |
| 6,800,764 B2 | 10/2004 | Kreft et al. | |
| 6,878,742 B2 | 4/2005 | Kreft et al. | |
| 7,166,622 B2 | 1/2007 | Kreft et al. | |
| 7,300,951 B2* | 11/2007 | Kreft et al. | 514/445 |
| 2004/0198778 A1 | 10/2004 | Kreft et al. | |
| 2005/0171180 A1 | 8/2005 | Resnick et al. | |
| 2005/0196813 A1 | 9/2005 | Kreft et al. | |
| 2007/0037778 A1 | 2/2007 | Kreft et al. | |

FOREIGN PATENT DOCUMENTS

| | | |
|---|---|---|
| EP | 510700 A2 | 10/1992 |
| EP | 652009 | 5/1995 |
| EP | 1172361 A1 | 12/1999 |
| EP | 1088821 A1 | 4/2001 |
| JP | 5-148233 | 6/1993 |
| JP | 11-343279 | 1/2002 |
| WO | WO-95/29904 A1 | 11/1995 |
| WO | WO-98/03166 A1 | 1/1998 |
| WO | WO-98/22104 A3 | 5/1998 |

(Continued)

OTHER PUBLICATIONS

Abstract of Japanese Patent No. JP-11-343279 Jan. 26, 2002.

(Continued)

*Primary Examiner*—Golam M Shameem
(74) *Attorney, Agent, or Firm*—Scott K. Larsen; Howson & Howson LLP

(57) ABSTRACT

Compounds of Formula (I),

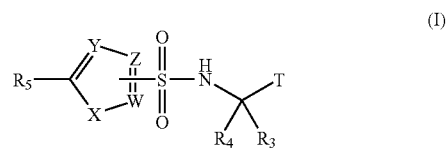

are provided where T is CHO, $COR_8$, or $C(OH)R_1R_2$; $R_1$ and $R_2$ are hydrogen, optionally substituted lower alkyl, $CF_3$, optionally substituted alkenyl, or optionally substituted alkynyl; $R_3$ is hydrogen or optionally substituted lower alkyl; $R_4$ is $(CF_3)_n$alkyl, $(CF_3)_n$(substituted alkyl), $(CF_3)_n$alkylphenyl, $(CF_3)_n$alkyl(substituted phenyl), or $(F)_n$cycloalkyl; n=1-3; $R_5$ is hydrogen, halogen, $CF_3$, diene fused to Y when Y=C, or substituted diene fused to Y when Y=C; W, Y and Z are C, $CR_6$ or N where at least one of W, Y or Z are C; $R_6$ is hydrogen, halogen, or optionally substituted lower alkyl; X is O, S, $SO_2$, or $NR_7$; $R_7$ is hydrogen, optionally substituted lower alkyl, optionally substituted benzyl, or optionally substituted phenyl; and $R_8$ is lower alkyl, $CF_3$, or optionally substituted phenyl. Methods of preparing and using these compounds for inhibiting beta amyloid production and for treatment of Alzheimer's Disease and Down's syndrome are also described.

30 Claims, No Drawings

FOREIGN PATENT DOCUMENTS

| | | |
|---|---|---|
| WO | WO-98/22493 A2 | 5/1998 |
| WO | WO-00/09107 A2 | 2/2000 |
| WO | WO-00/50391 A1 | 8/2000 |
| WO | WO-01/23379 A1 | 4/2001 |
| WO | WO-01/27091 A1 | 4/2001 |
| WO | WO-01/27108 A1 | 4/2001 |
| WO | WO-01/70677 A1 | 9/2001 |
| WO | WO-02/057252 A1 | 7/2002 |
| WO | WO-03/050063 A1 | 6/2003 |
| WO | WO-03/103660 A1 | 12/2003 |
| WO | WO-2005/073198 | 8/2005 |

OTHER PUBLICATIONS

Augelli-Szafran et al., "β-amyloid as a target for Alzheimer's Disease therapy", Annual Reports in Medicinal Chemistry, Ch. 3:21-30, 1999.

Dodart et al., "The β-amyloid precursor protein and its derivatives: From biology to learning and memory process", Reviews in the Neurosciences, 11(2-3):75-93, 2000.

Dovey et al., "Functional gamma-secretase inhibitors reduce beta-amyloid peptide levels in brain", J. Neurochem., 76:173-181, Jan. 2001.

Esler et al., "Transition-state analogue inhibitors of β-secretase bind directly to presenilin-1", Nature Cell Bio., 2:428-434, Jul. 2000.

Findeis et al., "Modified-peptide inhibitors of amyloid β-peptide polymerization", Biochem., 38(21):6791-6800, May 1999.

Ghosh et al., "Design of potent inhibitors for human brain memapsin 2 (β-secretase)", J. Am. Chem. Soc., 122:3522-3523, 2000.

Goate, A., "Monogenetic determinants of Alzheimer's Disease: APP mutations", Cell. Mol. Life Sci., 54:897-901, Sep. 1998.

Han et al., "Total asymmetric synthesis of highly constrained amino acids isopropyl-2',6'-dimethyl-tyrosines", Tetrahedron Letters, 38(29):5135-5138, 1997.

John et al., "Chapter 2. Alzheimer's Disease: Recent advances on the amyloid hypothesis", Ann. Reports Med. Chem., 32:11-20, 1997.

Josien, H., "Recent advances in the development of gamma-secretase inhibitors", Curr. Opin. Drug. Discov. Devel., 5(4):513-525, Jul. 2002.

Larner et al., "Review—Central and peripheral nervous systems—Alzheimer's disease: Towards therapeutic manipulation of the amyloid precursor protein and amyloid peptides", Exp. Opin. Ther. Patents, 7(10):1115-1127, 1997.

Li et al., "Photoactivated β-secretase inhibitors directed to the active site covalently label presenilin 1", Nature, 405:689-694, Jun. 2000.

Li et al., "The amyloid precursor protein of Alzheimer's Disease in human brain and blood", J. of Leuko. Bio., 66:567-574, Oct. 1999.

Moore et al., "Inhibition of β-amyloid formation as a therapeutic strategy", Exp. Opin. Ther. Patents, 9(2):135-146, 1999.

Näslund et al., "Correlation between elevated levels of amyloid β-peptide in the brain and cognitive decline", JAMA, 283(12):1571-1577, Mar. 2000.

Olson et al., "Chapter 4. Secretase inhibitors as therapeutics for Alzheimer's Disease", Ann. Reports in Med. Chem., 35:31, 2000.

Rishton et al., "Fenchylamine sulfonamide inhibitors of amyloid peptide production by the β-secretase proteolytic pathway: potential small-molecule therapeutic agents for the treatment of Alzheimer's Disease", J. Med. Chem., 43(12):2297-2299, Jun. 15, 2000.

Roggo, S., "Inhibition of BACE, A promising approach to Alzheimer's Disease therapy", Curr. Top. Med. Chem., 2(4):359-370, Apr. 2002.

Sabbagh et al., "β-amyloid and treatment opportunities for Alzheimer's Disease", Alzheimer's Disease Review, 3:1-19, 1997.

Sinha et al., "Purification and cloning of amyloid precursor protein β-secretase from human brain", Nature, 402:537-540, Dec. 1999.

Skovronsky et al., "β-secretase revealed: Starting gate for race to novel therapies for Alzheimer's Disease", TIPS, 21:161-163, May 2000.

Small et al., "Alzheimer's Disease and the amyloid protein: What is the role of amyloid?", J. of Neurochem., 73(2):443-449, Aug. 1999.

Testa et al., "Prodrugs revisited: The "Ad Hoc" approach as a complement to ligand design", Med. Res. Rev., 16(3):233-241, May 1996.

Tung et al., "Design of substrate-based inhibitors of human β-secretase", J. Med. Chem., 45(2):259-262, 2002.

Varghese et al., "Chapter 2. Alzheimer's Disease: Recent Advances on the Amyloid Hypothesis", Ann. Reports Med. Chem., 32:11, 1997.

Wagner et al., "Modulation of amyloid protein precursor processing as a means of retarding progression of Alzheimer's Disease", J. Clin. Invest., 104(10):1329-1332, Nov. 1999.

Wermuth et al., "Molecular variations based on Isosteric replacements", The Prac. of Med. Chem., 203-237, 1996.

Wolfe et al., "A substrate-based difluoro ketone selectively inhibits Alzheimer's β-secretase activity", J. Med. Chem., 41:6-9, Jan. 1, 1998.

* cited by examiner

US 7,547,725 B2

FLUORO- AND TRIFLUOROALKYL-CONTAINING HETEROCYCLIC SULFONAMIDE INHIBITORS OF BETA AMYLOID PRODUCTION AND DERIVATIVES THEREOF

CROSS-REFERENCE TO RELATED APPLICATIONS

This application is a continuation of U.S. patent application Ser. No. 10/810,517, filed Mar. 26, 2004 now U.S. Pat. No. 7,300,951, which claims the benefit of the priority under 35 USC § 119(e) of U.S. Provisional Patent Application No. 60/459,228, filed Mar. 31, 2003, now abandoned.

BACKGROUND OF THE INVENTION

This invention relates to inhibitors of beta amyloid production, which have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in brain not only precede tau pathology but also correlate with cognitive decline. Further suggesting a causative role for beta amyloid in AD, recent studies have shown that aggregated beta amyloid is toxic to neurons in cell culture.

Beta amyloid protein is composed mainly of 39 to 42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

There continues to be a need for compositions useful in inhibiting beta amyloid production and in the treatment of the effects of conditions associated therewith.

SUMMARY OF THE INVENTION

These compounds are useful for the treatment of conditions in which beta amyloid levels are elevated (e.g., AD, Down's Syndrome). Systemic administration of these compounds to subjects at risk of, or suffering from, these diseases lowers beta amyloid protein levels with subsequent reduction in the toxic beta amyloid aggregates in the brains of these patients.

Advantageously, the trifluoroalkyl- and fluoro-containing heterocyclic sulfonamide compounds within formula (I) have been found to have unexpectedly good beta-amyloid inhibitory activity. The compounds of formula (I) are characterized by increased stability against oxidation (Phase 1 metabolic stability), as compared to the corresponding compounds without the trifluoroalkyl or fluoro groups. Further, compounds within formula (I) as identified herein have been found to have increased metabolic stability and circulating half-life, and thus, enhanced bioactivity as compared to the corresponding compound without the trifluoroalkyl or fluoro groups.

Additionally, trifluoroalkyl- and fluoro-containing compounds within formula (I) have been found to have increased potency as compared to the corresponding unfluorinated compounds. Thus, the compounds of the invention are anticipated to be useful in lower doses than prior art compounds.

These and other aspects of the invention will be apparent to one of skill in the art upon reading of the following detailed description of the invention.

DETAILED DESCRIPTION OF THE INVENTION

The invention consists of compounds of Formula (I), their pharmaceutical formulations, and their use in modulating beta amyloid production in subjects at risk for, or suffering from, AD or other diseases resulting from elevated levels of beta amyloid protein in the brain. The present invention therefore provides compounds of Formula (I):

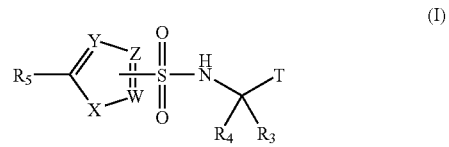

(I)

wherein, T is selected from the group consisting of CHO, $COR_8$, and $C(OH)R_1R_2$; $R_1$ and $R_2$ are independently selected from the group consisting of hydrogen, lower alkyl, substituted lower alkyl, $CF_3$, alkenyl, substituted alkenyl, alkynyl, and substituted alkynyl; $R_3$ is selected from the group consisting of hydrogen, lower alkyl and substituted lower alkyl; $R_4$ is selected from the group consisting of $(CF_3)_n$alkyl, $(CF_3)_n$(substituted alkyl), $(CF_3)_n$alkylphenyl, $(CF_3)_n$alkyl (substituted phenyl), and $(F)_n$cycloalkyl; n=1-3; $R_5$ is selected from the group consisting of hydrogen, halogen, $CF_3$, diene fused to Y when Y=C, and substituted diene fused to Y when Y=C; W, Y and Z are independently selected from the group consisting of C, $CR_6$ and N with the proviso that at least one of W or Y or Z must be C; $R_6$ is selected from the group consisting of hydrogen, halogen, lower alkyl, and substituted lower alkyl; X is selected from the group consisting of O, S, $SO_2$, and $NR_7$; $R_7$ is selected from the group consisting of hydrogen, lower alkyl, substituted lower alkyl, benzyl, substituted benzyl, phenyl, and substituted phenyl; and $R_8$ is selected from the group consisting of lower alkyl, $CF_3$, phenyl, and substituted phenyl; and pharmaceutically acceptable salts and/or hydrates or prodrugs thereof.

Of these compounds, the preferred members are those in which $R_4$ is $(CF_3)_n$alkyl, such as $CF_3$, $CF_3CH_2$, $CH(CH_3)CH_2CF_3$, $CH(CH_2CF_3)_2$, or $CH(CF_3)_2$. Other preferred members include compounds where $R_4$ is $(F)_n$cycloalkyl, preferably, $(F)_2$cycloalkyl, more preferably $(F)_2$cyclohexane and bicyclo[3.1.0]hexane, and most preferably 4,4-difluorocyclohexane and 4,4-difluorobicyclo[3.1.0]-3-hexane.

In one embodiment, T is $C(OH)R_1R_2$, $R_1$ and $R_2$ are hydrogen, $R_3$ is hydrogen, $R_4$ is $(CF_3)_2CH$, preferably $R_4$ is of S-stereochemistry, $R_5$ is halogen, and W=C, X=S, Y=CH, Z=CH with the sulfonamide attached to C-2 of the thiophene ring.

In another embodiment, T is CHO, $R_1$ and $R_2$ are hydrogen, $R_3$ is hydrogen, $R_4$ is $CH(CH_3)CH_2CF_3$, $R_5$ is halogen, and W=C, X=S, Y=CH, Z=CH with the sulfonamide attached to C-2 of the thiophene ring.

In a further embodiment, T is $C(O)R_8$, $R_1$ and $R_2$ are hydrogen, $R_3$ is hydrogen, $R_4$ is $CF_3CH_2(CH_3)CH$, $R_5$ is halogen, $R_8$ is $CH_3$, and W=C, X=S, Y=CH, Z=CH with the sulfonamide attached to C-2 of the thiophene ring.

In yet another embodiment, T is $C(OH)R_1R_2$, $R_1$ and $R_2$ are hydrogen, $R_3$ is hydrogen, $R_4$ is $(CH_2CF_3)_2CH$, $R_5$ is halogen, and W=C, X=S, Y=CH, Z=CH with the sulfonamide attached to C-2 of the thiophene ring.

In still a further embodiment, T is $C(OH)R_1R_2$, $R_1$ and $R_2$ are $CH_3$, $R_3$ is hydrogen, $R_4$ is $CF_3CH_2(CH_3)CH$, $R_5$ is halogen, and W=C, X=S, Y=CH, Z=CH with the sulfonamide attached to C-2 of the thiophene ring.

In another embodiment, T is $C(OH)R_1R_2$, $R_1$ is $CH_3$, $R_2$ is hydrogen, $R_3$ is hydrogen, $R_4$ is $(CF_3)_2CH$, $R_5$ is halogen, and W=C, X=S, Y=CH, Z=CH with the sulfonamide attached to C-2 of the thiophene ring.

In yet a further embodiment, T is $C(OH)R_1R_2$, $R_1$ and $R_2$ are hydrogen, $R_3$ is hydrogen, $R_4$ is $(F)_2$cycloalkyl, $R_5$ is halogen, and W=C, X=S, Y=CH, Z=CH with the sulfonamide attached to C-2 of the thiophene ring.

The point of attachment of the W—X—Y-Z-C heterocyclic ring to the $SO_2$ group is not a limitation of the present invention. However, in one preferred embodiment, the ring is attached to the $SO_2$ group through a carbon-atom. However, the ring may be attached through a N heteroatom.

The compounds of the invention may contain one or more asymmetric carbon atoms and some of the compounds may contain one or more asymmetric (chiral) centers and may thus give rise to optical isomers and diastereomers. While shown without respect to stereochemistry in Formula (I), when the compounds of Formula (I) contain one or more chiral centers, at least the chiral center of the β-amino alcohol is of S-stereochemistry. Most preferably, the carbon atom to which N, $R_3$ and $R_4$ are attached is of S-stereochemistry. Thus, the invention includes such optical isomers and disastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein to refer to both straight- and branched-chain saturated aliphatic hydrocarbon groups having one to ten carbon atoms, preferably one to eight carbon atoms and, most preferably, one to six carbon atoms; as used herein, the term "lower alkyl" refers to straight- and branched-chain saturated aliphatic hydrocarbon groups having one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl groups with at least one carbon-carbon triple bond and two to eight carbon atoms, preferably two to six carbon atoms.

The terms "substituted alkyl", "substituted alkenyl", and "substituted alkynyl" refer to alkyl, alkenyl, and alkynyl groups as just described having from one to three substituents including halogen, CN, OH, $NO_2$, amino, aryl, heterocyclic, substituted aryl, substituted heterocyclic, alkoxy, substituted alkoxy, aryloxy, substituted aryloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

The term "cycloalkyl" is used herein to describe a carbon-based saturated ring having more than 3 carbon-atoms and which forms a stable ring. The term cycloalkyl can include groups where two or more cycloalkyl groups have been fused to form a stable multicyclic ring. Preferably, cycloalkyl refers to a ring having about 4 to about 9 carbon atoms, and more preferably about 6 carbon atoms.

The term "substituted cycloalkyl" is used herein to refer to a cycloalkyl group as just described and having from one to five substituents including, without limitation, hydrogen, halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, aminoalkyl, and substituted aminoalkyl.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane.

The term "substituted aryl" refers to aryl as just defined having one to four substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "diene" refers to an unsaturated hydrocarbon or diolefin having two double bonds. The term "substituted diene" refers to a diene which is substituted with one to two substituents including halogen, CN, OH, $NO_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

As "diene" and "substituted diene" are used in the context of $R_5$, an embodiment in which the substituted diene is 3-chloro-1,3-butadiene which is fused to the thiophene ring at $R^5$ and Y to form a benzothiophene. Other suitable dienes include 1,3-butadienyl- and 2-trifluoromethyl-1,3-butadienyl. However, other suitable substituted and unsubstituted dienes may be readily selected from among the compounds as defined herein.

The term "substituted benzyl" refers to a benzyl group, having substituted on the benzene ring, one to five substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "heterocyclic" is used herein to describe a stable 4- to 7-membered monocyclic or a stable multicyclic heterocyclic ring which is saturated, partially unsaturated, or unsaturated, and which includes carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocyclic" is used herein to describe the heterocyclic just defined having one to four substituents including halogen, CN, OH, $NO_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

Where the terms "substituted alkyl" or "substituted alkylphenyl" are recited, the substitution may occur at the alkyl group or on the corresponding base compound.

The term "alkoxy" is used herein to refer to the OR group, where R is alkyl or substituted alkyl.

The term "aryloxy" is used herein to refer to the OR group, where R is aryl or substituted aryl.

The term "arylthio" is used herein to refer to the SR group, where R is aryl or substituted aryl.

The term "alkylcarbonyl" is used herein to refer to the RCO group, where R is alkyl or substituted alkyl.

The term "alkylcarboxy" is used herein to refer to the COOR group, where R is alkyl or substituted alkyl.

The term "aminoalkyl" refers to both secondary and tertiary amines wherein the alkyl or substituted alkyl groups, containing one to eight carbon atoms, which may be either same or different and the point of attachment is on the nitrogen atom.

The term "halogen" refers to Cl, Br, F, or I.

The term "ring" structure, includes a monocyclic structure, a bridged cyclo structure, and fused cyclo structures, unless the type of ring structure is otherwise specified.

The compounds of the present invention can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include diethanolamine, ethylenediamine, and salts with alkali metals or alkaline earth metals, such as sodium (e.g., sodium hydroxide), potassium (e.g., potassium hydroxide), calcium (e.g., calcium hydroxide) or magnesium (e.g., magnesium hydroxide).

These salts, as well as other compounds of the invention may be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

In one embodiment, the compounds of Formula (I) are thiophenesulfonamides, and more desirably, 5-halo thiophenesulfonamides, and most desirably, 5-halo thiophene sulfonamides with β-branches in the side chain of a primary alcohol. Thus, with respect to Formula (I), the compound of the invention desirably has a structure in which $R_1$ and $R_2$ are hydrogen; $R_3$ is hydrogen, $R_4$ is $(CF_3)_2CH$ of S-stereochemistry, $R_5$ is halogen, W=C, X=S, Y=CH, Z=CH with the sulfonamide attached to C-2 of the thiophene ring.

In another embodiment, the compounds of Formula (I) are furansulfonamides.

Thus, with respect to Formula (I), the compound of the invention has a structure in which X is O. In one desirable embodiment, the furansulfonamides are characterized by β-branches in the side chain of a primary alcohol.

In yet another embodiment, the compounds of Formula (I) are pyrazole sulfonamides. Thus, with respect to Formula (I), the compound has a structure in which X is $NR_7$, W is N and Z and Y are C or $CR_6$, with the proviso that at least one of Y or Z must be C.

These and the other compounds of the invention can be prepared following the Schemes illustrated below.

Synthesis

The compounds of the present invention can be prepared in a number of ways well known to one skilled in the art of organic synthesis. The compounds of the present invention can be prepared using the methods described below, together with synthetic methods known in the synthetic organic arts or variations of these methods by one skilled in the art. (See, generally, Comprehensive Organic Synthesis, "Selectivity, Strategy & Efficiency in Modern Organic Chemistry", ed., I. Fleming, Pergamon Press, New York (1991); Comprehensive Organic Chemistry, "The Synthesis and Reactions of Organic Compounds", ed. J. F. Stoddard, Pergamon Press, New York (1979)). Preferred methods include, but are not limited to, those outlined below.

A first method of preparation consists of reaction of a 1,2-aminoalcohol II with the appropriate sulfonyl halide in the presence of a base such as triethylamine (TEA) and in a suitable solvent to afford compounds of Formula III. For compounds where $R_2$ and $R_1$ are hydrogen, oxidation of the N-sulfonyl primary alcohol with pyridinium chlorochromate (PCC), the Dess Martin periodinane reagent [D. B. Dess, J. C. Martin, J. Org. Chem., 48:4155 (1983)] or under Swern conditions [Omura et al, J. Org. Chem., 41:957 (1976)] then affords the corresponding aldehyde IV which can be reacted with Grignard reagents (RMgX, where R is an organic radical and X is a halogen) to afford the secondary alcohols V as a mixture of diastereomers which can be separated by high performance liquid chromatography (HPLC) (Scheme 1).

Scheme 1

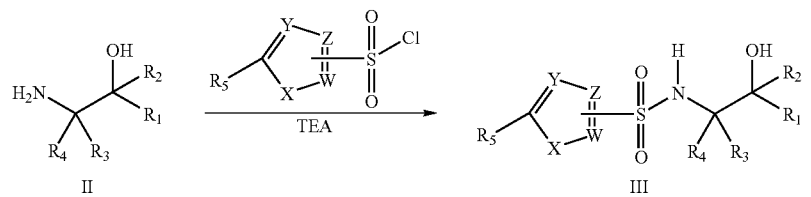

PCC or Dess-Martin when in III, $R_1$=$R_2$=H

-continued

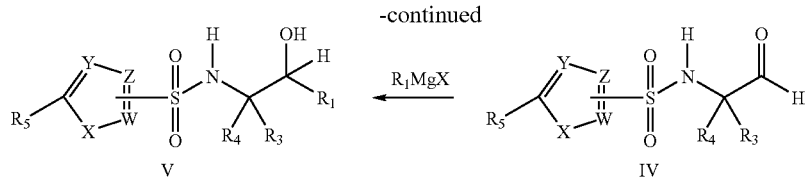

A second method of preparation involves reaction of an α-amino acid or ester IX with the appropriate sulfonyl halide in the presence of a base such as triethylamine and in a suitable solvent to afford compounds of Formula X (Scheme 2). The intermediate N-sulfonyl acid X (Rx=H) can be converted to the corresponding primary alcohol VIII ($R^1$=$R_2$=H) utilizing standard methodology such as lithium aluminum hydride (LiAlH$_4$), B$_2$H$_6$ or cyanuric chloride/NaBH$_4$. The intermediate N-sulfonyl ester X (Rx=alkyl, Bn) can also be reduced to the corresponding primary alcohol VIII ($R_1$=$R_2$=H) utilizing standard methodology such as LiAlH$_4$. Alternatively, the intermediate N-sulfonyl ester X (Rx=alkyl, Bn) can be converted to the aldehyde IV with DIBAL. Finally, the intermediate N-sulfonyl ester X (Rx=alkyl, Bn) can be reacted with 2 equivalents of Grignard reagent to afford the tertiary alcohols III with $R_1$=$R_2$. Alternatively, for tertiary alcohols III with $R_1$ not equal to $R_2$, the corresponding Weinreb amide of the N-sulfonyl acid can be prepared and sequentially reacted with $R_1$MgX and $R_2$MgX.

In a variation of the second method to prepare the primary alcohols, an α-amino acid or ester (or N-protected derivative thereof) VI is first converted to the corresponding primary 1,2-aminoalcohol VII (using the methodology outlined in the previous paragraph), which is subsequently, after deprotection (if necessary), reacted with the appropriate sulfonyl halide (Scheme 3) to afford compounds of Formula VIII.

Scheme 3

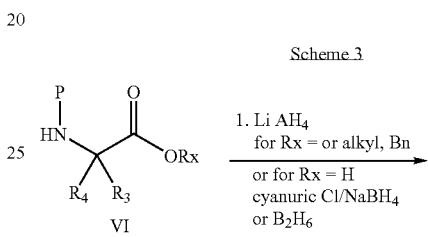

Scheme 2

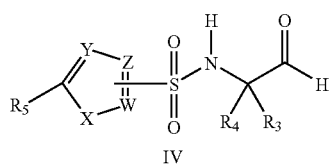

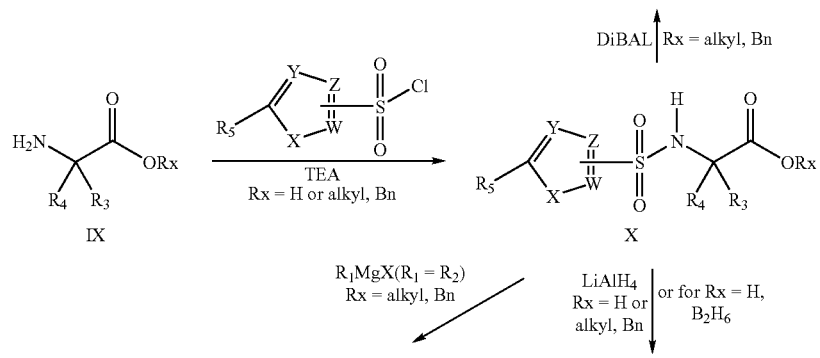

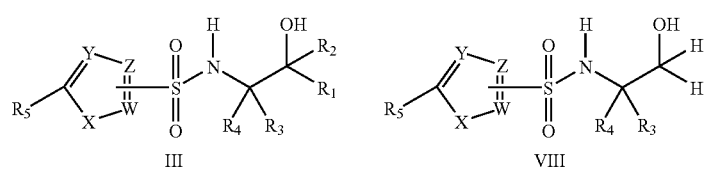

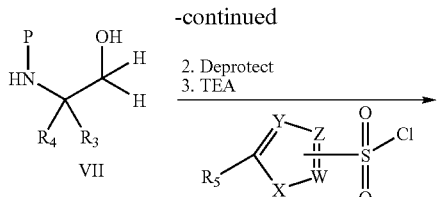

P = H or protecting group

For preparation of compounds derived from unnatural α-amino acids containing beta branching in the amino acid side chain, a method of preparation based on the work of Hruby (Tet. Lett. 38: 5135-5138 (1997)) is outlined in Scheme 4. This route entails formation of the α,β-unsaturated amide XIV of the Evans chiral auxiliary from an acylbromide XI via a Horner-Emmons reaction sequence, followed by conjugate addition of an organocuprate, trapping of the resulting enolate anion XV with N-Bromosuccinamide (NBS), displacement of the bromide XVI with azide anion (provided by tetramethylguanidinium azide (TMGA) or sodium azide to afford XVII, followed by reduction to the 1,2-amino alcohol and subsequent sulfonylation to afford the target compound XVIII.

When the heterocycle attached to the sulfonamide in the above alcohols is thiophene, the corresponding sulfone derivative XX may be obtained by oxidation of the thiophene compound XIX with 3-Chloroperoxybenzoic acid (MCPBA) (Scheme 5).

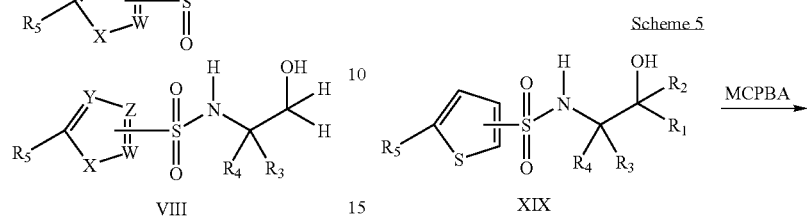

An alternate preparation of sulfonamides derived from unnatural 1,2-aminoalcohols utilizes the Bucherer modification of the Strecker α-amino acid synthesis (Scheme 6). In this route, an aldehyde XXI is reacted with cyanide anion and ammonium carbonate to afford the hydantoin XXII, which is hydrolyzed to the α-amino acid XXIII. This compound is then reduced to XXIV and sulfonylated to afford the desired compounds of Formula XXV. Alternatively, the intermediate amino acid XXIII can be first sulfonylated to afford XXVI

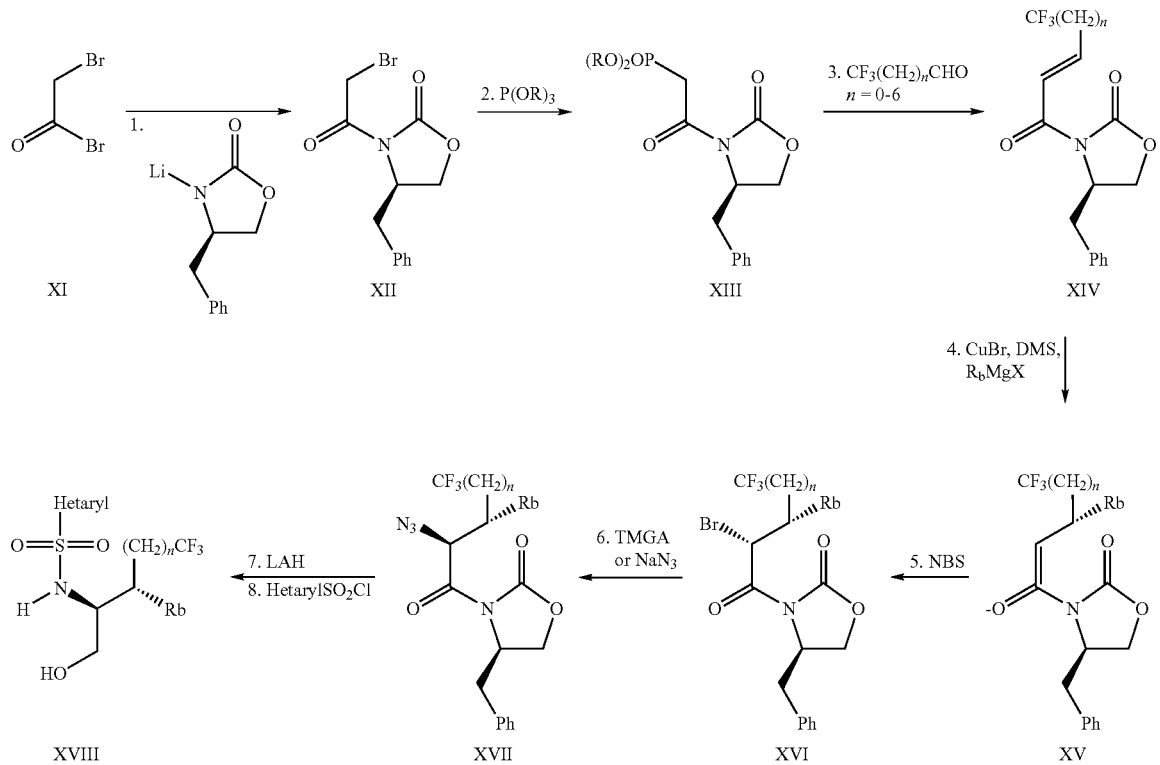

which is then reduced to XXV. The racemic products XXIII, XXV or XXVI can be resolved to the desired S enantiomer using standard methodology by one skilled in the art.

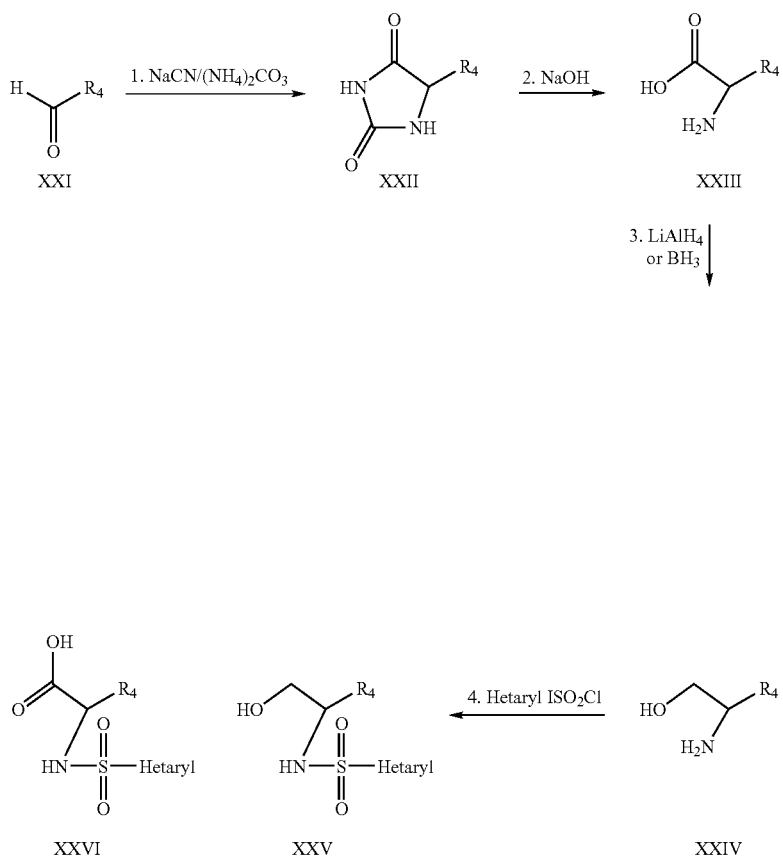

For sulfonamides derived from 1,2-aminoalcohols in the secondary alcohol series with $R_1$=H and $R_2$=$CF_3$ (compound XXVII), a method of preparation has been devised that is outlined in Scheme 7 starting from the aldehyde IV (prepared as in Scheme 1).

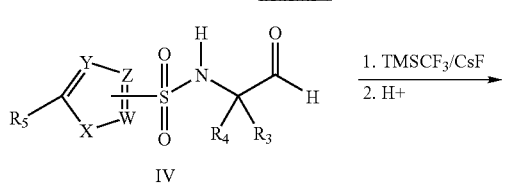

-continued

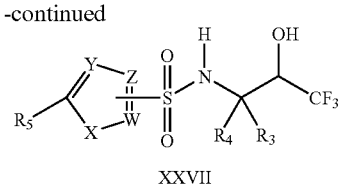

XXVII

When the heterocycle attached to the sulfonamide in the above alcohols is thiophene, the corresponding 5-iodo and 5-fluoro-thiophene derivatives may be obtained by conversion of the 5-bromo-thiophene derivative XXVIII (obtained as in Scheme 1) to a 5-trialkyltin-thiophene intermediate XXIX which can be converted to either the 5-iodo-thiophene (XXXI) by treatment with sodium iodide and chloramine T or the 5-fluoro-thiophene analog (XXX) by treatment with the SELECTFLUOR® reagent (Aldrich Chem Co.) (Scheme 8).

Scheme 8

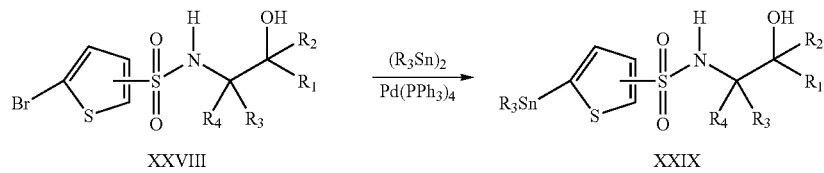

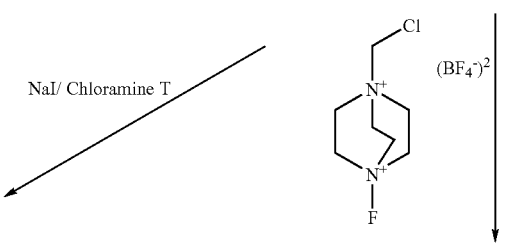

Another method of preparing chirally pure N-sulfonyl 1,2-amino alcohols derived from α-amino acids is outlined in Scheme 9. This method initially involves formation of the α,β-unsaturated amide XXXIV of the Evans chiral auxiliary from the bromoacetyl bromide XI via a Horner-Emmons reaction sequence. Conjugate addition of an organocuprate and protonation of the resulting enolate anion affords XXXV, which is then converted to the corresponding enolate and electrophilically aminated with trisyl azide to afford the key intermediate XXXVI (J. Am. Chem. Soc. 109: 6881-6883 (1987)). The azide intermediate XXXVI is then hydrolyzed to the α-azido acid XXXVII and reduced to the chirally pure α-amino acid XXXVIII which can be converted to the corresponding N-sulfonyl 1,2-amino alcohols by methods previously described above (e.g., Schemes 2 or 3).

Scheme 9

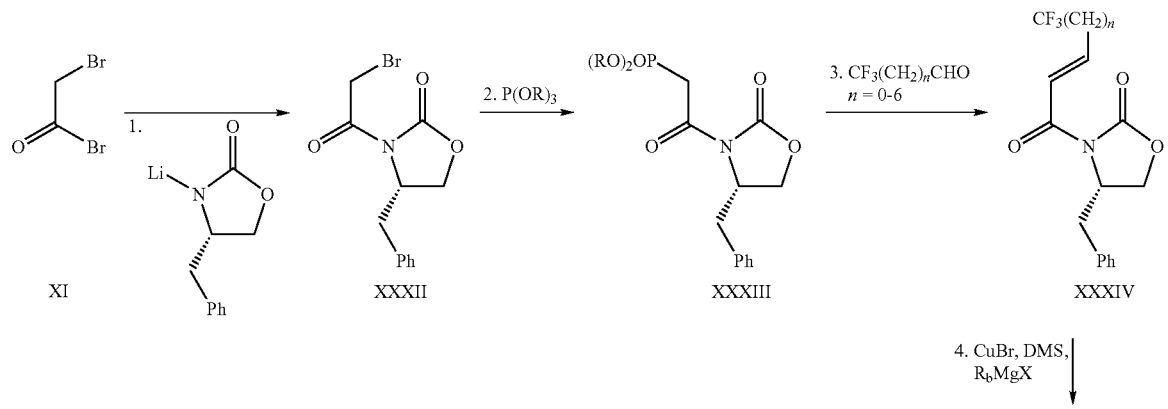

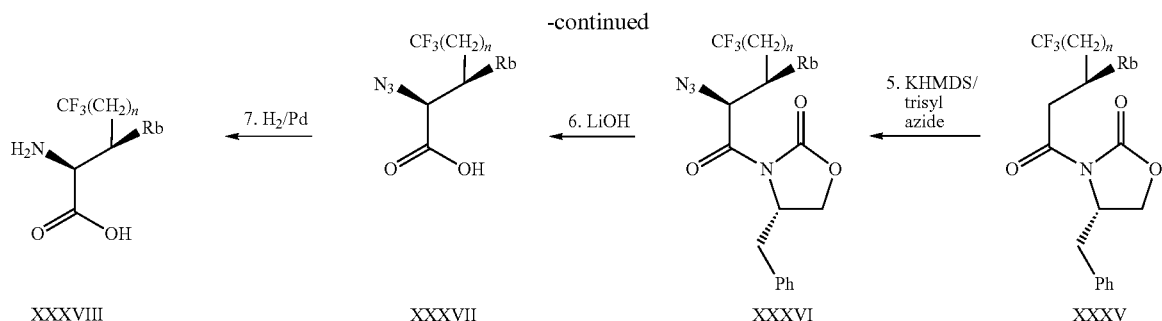

Finally, chirally pure α-amino acids XLI, one of the possible synthetic precursors of chiral N-sulfonyl 2-amino alcohols XLIII, can also be prepared utilizing asymmetric variants of the Strecker α-amino acid synthesis as outlined in Schemes 10 (J. Org. Chem. 61:440-441 (1996)) and 11 (J. Org. Chem. 54:1055-1062 (1989)).

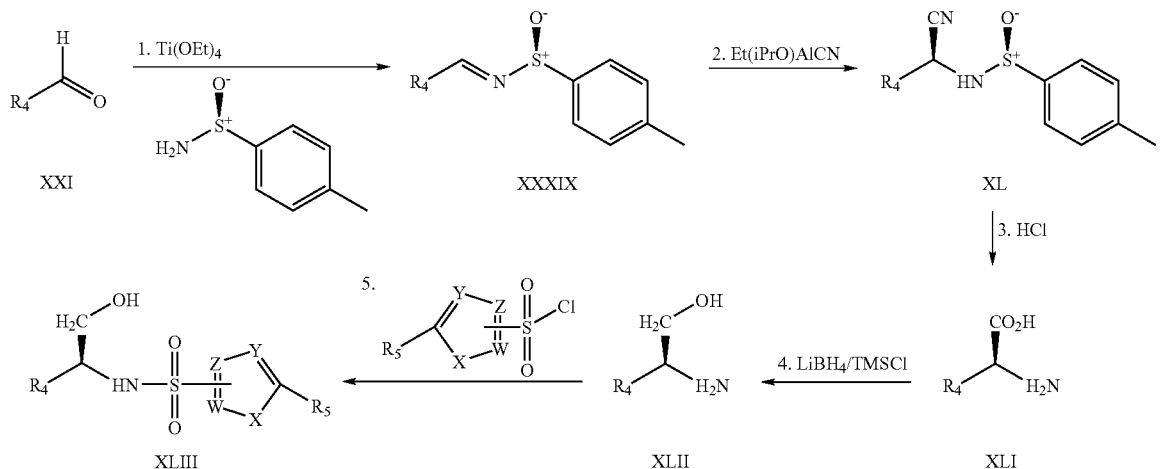

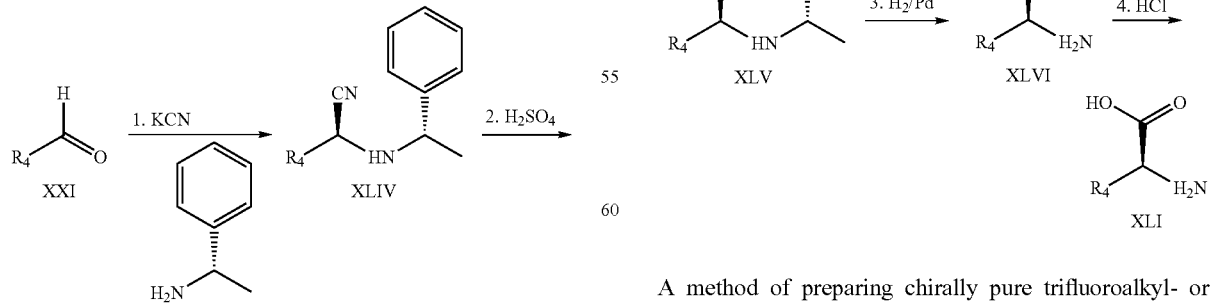

A method of preparing chirally pure trifluoroalkyl- or fluoro-containing heterocyclic sulfonamide compounds according to Formula (I) is outlined in Schemes 12 and 13. Scheme 12 outlines procedures described in the literature for formation of a suitable aminoester XLVII [W. H. Vine, et al, J Med Chem. 1981, 24: 1043-1047 and R. Keese, et al, Synthesis, 1996, 695-696]. Based on the literature and the teachings herein, one of skill in the art will recognize that, depending upon the desired aminoester, one can readily select another trifluoromethyl aldehyde in step 3 depending upon the substituents selected for $R_{4'}$ and $R_{3'}$, another chiral auxiliary in step 4, or utilize other reagents, substituents, or other reaction conditions in any of the outlined steps. However, if $R_{3'}$ is not equal to $R_{4'}$, then a mixture of olefin isomers is obtained in step 3 of Scheme 12 which requires separation before Step 4.

Scheme 12

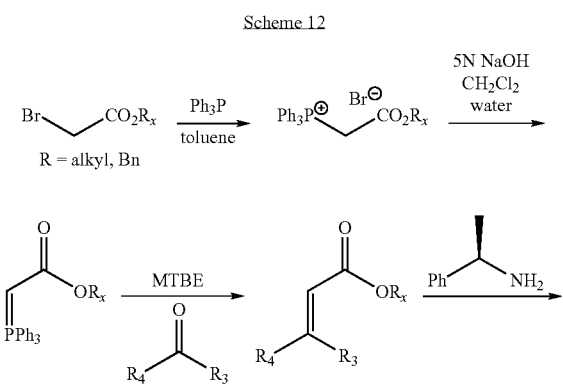

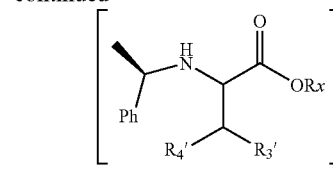

XLVII

~1:1 mix diasteromers

In Scheme 13, the aminoester XLVIII is filtered; it has been found that recrystallization at this step, which is described in the literature as essential, is not required. The intermediate aminoester XLVIII is converted to N-benzyl amino alcohol with DIBAL-H. The N-benzyl amino alcohol XLIX is hydrogenated in the presence of a suitable catalyst to provide an aminoalcohol L. The catalyst is removed via filtration and the solution concentrated to a solid. The aminoalcohol L is sulfonylated with BSA/triethylamine/DMAP (or another suitable agent, e.g. TMSCl/amine base) and a desired heterocyclic sulfonylchloride. The reaction is quenched to remove the silyl ether group (e.g., with aqueous HCl/THF) and filtered (e.g., using an $SiO_2$ plug) with ethyl acetate/hexane in a ratio which permits crystallization of the chirally pure trifluoromethyl-containing heterocyclic sulfonamide of Formula (I) of the invention.

Scheme 13

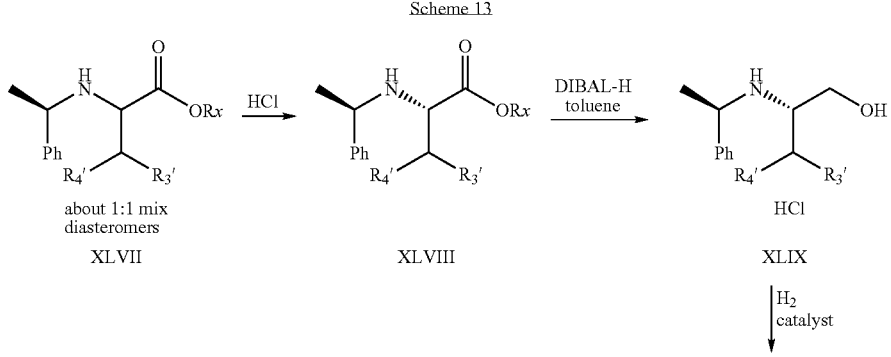

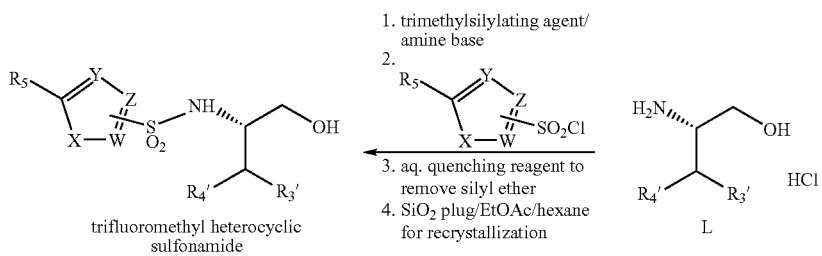

In addition to being useful for preparing the compounds of the invention, the method of Scheme 13 may be readily used for the preparation of trifluoroalkyl-, including trifluoromethyl-, and fluoro-containing compounds. More particularly, this method may be useful for preparing other trifluoroalkyl-, trifluoromethyl-, or fluoro-containing sulfonamides from a diastereomeric mixture of an aminoester having at least one chiral center and at least one trifluoroalkyl or fluoro group attached to at least one chiral center through an alkyl group or at least one fluoro group attached to a cycloalkyl group. As defined herein, the alkyl group may link one or more trifluoroalkyl to the chiral center directly. Alternatively, the trifluoroalkyl can be located on a substituent of a substituted alkyl group.

The compounds of the invention can also be prepared by reacting a secondary alcohol V with pyridinium chlorochromate (PCC) or the Dess Martin periodinane reagent [D. B. Dess, J. C. Martin, J. Org. Chem., 48:4155 (1983)] to afford the corresponding aldehyde LI (Scheme 14).

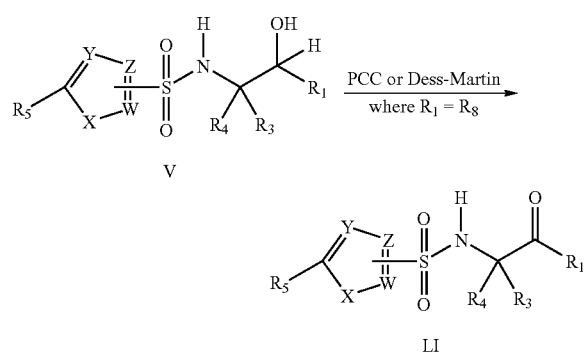

Scheme 14

A further method of preparing a trifluoromethylated or fluorinated heterocyclic sulfonamide compound includes the steps of (a) filtering a diastereomeric mixture of an aminoester, said aminoester having at least one chiral center and at least one trifluoromethyl or fluoro group attached to at least one chiral center through an alkyl group; (b) treating the aminoester with DIBAL-H in toluene to afford N-benzyl amino alcohol; (c) hydrogenating the N-benzyl amino alcohol with a catalyst and affording an amino alcohol; (d) sulfonylating the amino alcohol of (c) with a heterocyclic sulfonyl chloride; and (e) crystallizing the sulfonylated product of (d) to afford to chirally pure trifluoromethylated or fluorinated heterocyclic sulfonamide compound.

Another method of preparing trifluoromethylated or fluorinated heterocyclic sulfonamide compounds includes treating a trifluoromethylated or fluorinated aldehyde with a dehydrating agent and a chiral sulfinamide to form a trifluoromethylated or fluorinated chiral sulfinamide. One of skill in the art would readily be able to determine a suitable dehydrating agent for use in the present method including, without limitation, titanium ethoxide, magnesium sulfate, or molecular sieves such as 4 Å molecular sieves. The trifluoromethylated or fluorinated chiral sulfinamide can then be treated with a cyanating agent to form a trifluoromethylated or fluorinated diastereomeric α-amino nitrile, respectively. The selection of the cyanating agent for use in the present invention is within one skilled in the art and can include ethyl isopropoxy aluminum cyanide, among others. The trifluoromethylated or fluorinated diastereomeric α-amino nitrile can then be isolated and optionally purified using techniques known to those of skill in the art. Alternatively, the trifluoromethylated or fluorinated diastereomeric α-amino nitrile can be hydrolyzed to a trifluoromethylated or fluorinated α-amino acid, respectively, using techniques and agents known to those of skill in the art. The trifluoromethylated or fluorinated α-amino acid can then be reduced to a trifluoromethylated or fluorinated β-amino alcohol, respectively, using techniques and agents known to those of skill in the art. The trifluoromethylated or fluorinated β-amino alcohol can be reacted with a heterocyclic sulfonyl chloride to form the corresponding trifluoromethylated or fluorinated heterocyclic sulfonamide of the present invention.

Still a further method of the invention includes a method of preparing a trifluoromethylated or fluorinated heterocyclic sulfonamide compound, said method including the steps of: (a) treating a trifluoromethylated or fluorinated aldehyde with a dehydrating agent and a chiral sulfinamide to form a trifluoromethylated or fluorinated chiral sulfinamide; (b) treating said trifluoromethylated or fluorinated chiral sulfinimide with a cyanating agent to form a trifluoromethylated or fluorinated diastereomeric α-amino nitrile; (c) hydrolyzing said trifluoromethylated or fluorinated diastereomeric α-amino nitrile to a trifluoromethylated α-amino acid; (d) reducing said trifluoromethylated or fluorinated α-amino acid to a trifluoromethylated or fluorinated β-amino alcohol; and (e) reacting said trifluoromethylated or fluorinated β-amino alcohol with a heterocyclic sulfonyl chloride to form said trifluoromethylated or fluorinated heterocyclic sulfonamide.

Methods of Use

Compounds of Formula (I) are inhibitors of beta amyloid production. In preliminary studies using protease specific assays, exemplary compounds of Formula (I) have been shown to exhibit specific inhibition with respect to protease activity. Thus, the compounds of the present invention are useful for treatment and prevention of a variety of conditions in which modulation of beta amyloid levels provides a therapeutic benefit. Such conditions include, e.g., amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome, mild cognitive impairment (MCI), among others.

In addition, the compounds of Formula (I) may be utilized in generating reagents useful in diagnosis of conditions associated with abnormal levels of beta amyloid. For example, the compounds of Formula (I) may be used to generate antibodies, which would be useful in a variety of diagnostic assays. Methods for generating monoclonal, polyclonal, recombinant, and synthetic antibodies or fragments thereof, are well known to those of skill in the art. (See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Kohler and Milstein and the many known modifications thereof; PCT Patent Application No. PCT/GB85/00392; British Patent Application Publication No. GB2188638A; Amit et al., Science, 233:747-753 (1986); Queen et al., Proc. Nat'l. Acad. Sci. USA, 86:10029-10033 (1989); International Patent Publication No. WO90/07861; and Riechmann et al., Nature, 332:323-327 (1988); Huse et al, Science, 246:1275-1281 (1988)). Alternatively, the compounds of Formula (I) may themselves be used in such diagnostic assays. Regardless of the reagent selected (e.g., antibody or compound of Formula (I)), suitable diagnostic formats including, e.g., radioimmunoassays and enzyme-linked immunosorbent assays (ELISAs), are well known to those of skill in the art and are not a limitation on this embodiment of the invention.

The beta amyloid inhibitory activity of many of the compounds of the present invention has been determined using the Repressor Release Assay (RRA). See, Table 5 below. A compound is considered active in RRA if it leads to at least a 1.5 fold increase in luciferase activity at 20 µg/mL and is non-toxic.

Additionally, cellular, cell-free and in vivo screening methods to detect inhibitors of beta amyloid production are known in the art. Such assays may include radioimmunoassays and enzyme-linked immunosorbent assay (ELISA), among others. See, e.g., P. D. Mehta, et al., Techniques in Diagnostic Pathology, vol. 2, eds., Bullock et al, Academic Press, Boston, pages 99-112 (1991), International Patent Publication No. WO 98/22493, European Patent No. 0652009, and U.S. Pat. Nos. 5,703,129 and 5,593,846. Selection of an appropriate in vitro or in vivo screening assay is not a limitation of the present invention.

Pharmaceutical Formulation

The compounds of this invention may be administered to a subject by any desirable route, taking into consideration the specific condition for which it has been selected. By subject is meant any suitable mammal, including humans, domestic animals (e.g., canines and felines), and livestock, which have been recognized as having or at risk of having one or more of the conditions for which modulation of beta amyloid levels is desirable. Thus, the compounds of the invention are useful for treatment and/or prevention of a number of human and veterinary conditions. As used herein, "prevention" encompasses prevention of symptoms in a subject who has been identified as at risk for the condition, but has not yet been diagnosed with the same and/or who has not yet presented any symptoms thereof.

These compounds may be delivered or administered by any suitable route of delivery, e.g., oral, injection, inhalation (including oral, intranasal and intratracheal), intravenous, subcutaneous, intramuscular, sublingual, intracranial, epidural, intratracheal, rectal, vaginal, among others. Most desirably, the compounds are delivered orally, by inhalation or by a suitable parenteral route. The compounds may be formulated in combination with conventional pharmaceutical carriers that are physiologically compatible. Optionally, one or more of the compounds of the invention may be mixed with other active agents.

Suitable physiologically compatible carriers may be readily selected by one of skill in the art. For example, suitable solid carriers include, among others, one or more substances which may also act as flavoring agents, lubricants, solubilizers, suspending agents, fillers, glidants, compression aids, binders or tablet-disintegrating agents or an encapsulating material. In powders, the carrier is a finely divided solid, which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium or dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, suspending agents, thickening agents, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil, arachis oil, corn oil, peanut oil, and sesame oil). For parenteral administration the carrier can also be an oily ester such as ethyl oleate and isopropyl myristate. Sterile liquid carriers are used in sterile liquid form compositions for parenteral administration.

Optionally, additives customarily employed in the preparation of pharmaceutical compositions may be included in the compositions of the invention. Such components include, e.g., sweeteners or other flavoring agents, coloring agents, preservatives, and antioxidants, e.g., vitamin E, ascorbic acid, BHT and BHA.

Liquid pharmaceutical compositions that are sterile solutions or suspensions can be utilized by, for example, intramuscular, intraperitoneal or subcutaneous injection. Sterile solutions can also be administered intravenously. Oral administration may be either liquid or solid composition form.

Suitably, when prepared for use as an inhalant, the pharmaceutical compositions are prepared as fluid unit doses using a compound of the invention and a suitable pharmaceutical vehicle for delivery by an atomizing spray pump, or by dry powder for insufflation. For use as aerosols, the compound of the invention is formulated for and packaged in a pressurized aerosol container together with a gaseous or liquefied propellant, for example, dichlorodifluoromethane, carbon dioxide, nitrogen, propane, and the like, with the usual components such as cosolvents and wetting agents, as may be necessary or desirable. For example, the invention provides for delivery of a metered dose for oral or intranasal inhalation in one, two, or more actuations. Suitably, a dose is delivered in one or two actuations. However, other suitable delivery methods may be readily determined.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

As described herein, a therapeutically or prophylactically useful amount of a compound of the invention is that amount of a compound which alleviates the symptoms of the disease, e.g., AD, or which prevents the onset of symptoms, or the onset of more severe symptoms. The useful amounts of a compound may vary depending upon the formulation and route of delivery. For example, higher amounts may be delivered orally than when the compound is formulated for injection or inhalation, in order to deliver a biologically equivalent amount of the drug. Suitably, an individual dose (i.e., per unit) of a compound of the invention is in the range from about 1 µg/kg to about 10 g/kg. However, because compounds of the invention have improved bioactivity as compared to similar compounds lacking the trifluoroalkyl or fluoro substituents of the invention, these doses may suitably be selected from a lower range, e.g., from about 1 μg/kg to about 200 mg/kg more preferably 10 μg/kg to about 10 mg/kg, and most preferably about 100 μg/kg to about 1 mg/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds of this invention, a starting dose of about 375 to 500 mg per day with gradual increase in the daily dose to about 1000 mg per day may provide the desired dosage level in the human.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. Nos. 5,756,127 and 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

The following examples are provided to illustrate the production and activity of representative compounds of the invention and to illustrate their performance in a screening assay. One skilled in the art will appreciate that although specific reagents and conditions are outlined in the following examples, these reagents and conditions are not a limitation on the present invention.

EXAMPLES

Example 1

5-Chloro-N-[(1S,2R)-4,4,4-trifluoro-1-(hydroxymethyl)-2-methylbutyl]thiophene-2-sulfonamide A. Method 1

1. 2-Methyl-4,4,4-trifluorobutanal

To 2-methyl-4,4,4-trifluoro-1-butanol (7.5 g, 53 mmol) in methylene chloride ($CH_2Cl_2$) (125 mL) at 0° C. was added Dess-Martin periodinane (26.5 g, 63.3 mmol). The reaction mixture was warmed to 25° C. and stirred for 20 min. To this mixture was added diethyl ether ($Et_2O$-200 mL) followed by a solution of $Na_2S_2O_3$ (29.0 g, 185 mmol) in a saturated aqueous solution of sodium bicarbonate ($NaHCO_3$) (200 mL) and 100 mL of water. The milky white mixture was stirred until both phases were homogeneous. The phases were separated and the organic extract washed with saturated aqueous $NaHCO_3$ (25 mL) and aqueous 1 N $Na_2S_2O_3$ (25 mL) and dried using magnesium sulfate ($MgSO_4$). Solvents were removed by distillation at atmospheric pressure to give 2-methyl-4,4,4-trifluorobutanal (6.5 g, 88%). $^1H$ nuclear magnetic resonance (NMR) spectrum matched that which was reported in the literature (J. Fluorine Chem. 36: 163-170 (1987).

2. 5-(3,3,3-Trifluoro-1-methylpropyl)imidazolidine-2,4-dione

To sodium cyanide (18.4 g, 375 mmol) and ammonium carbonate (39.0 g, 500 mmol) in $H_2O$ (450 mL) was added 2-methyl-4,4,4-trifluorobutanal (17.5 g, 125 mmol) in ethanol (450 mL). The reaction mixture was heated to 90° C. for 17 h. After cooling to 25° C., about 500 mL of solvent was removed in vacuo. Concentrated HCl was added to acidify the mixture to a pH of about 1 to about 2 and a precipitate formed. The mixture was filtered and washed with aqueous 1 N HCl to give 5-(3,3,3-trifluoro-1-methylpropyl)imidazolidine-2,4-dione as a white solid (15.5 g, 59%).

Mass Spectrum (−ESI): 309 (M−H)⁻.
Anal: Calc'd for $C_7H_9F_3N_2O_2$ C, 40.01; H, 4.32; N, 13.33. Found: C, 39.91; H, 4.10; N, 13.20.

3. N-[(5-Chlorothien-2-yl)sulfonyl]-5,5,5-trifluoroisoleucine 5-(3,3,3-Trifluoro-1-methylpropyl)imidazolidine-2,4-dione (15.54 g, 73.95 mmol) was dissolved in a 150 mL solution of aqueous sodium hydroxide (NaOH-11.83 g, 295.8 mmol). The solution was heated by microwave in a sealed vessel for 1 hour. (Microwave conditions: 15 min. at about 100% power, 150° C., 50 psi, then 5 min 0% power, then 15 min at about 100% power, 150° C., 50 psi, then repeat sequence.) Water and ammonium hydroxide were removed from the reaction mixture in vacuo and the resulting crude amino acid and NaOH mixture was used in the next reaction without further purification.

The crude amino acid and NaOH mixture was dissolved in 300 mL of water. The mixture was cooled to about 0° C. in an ice bath. 5-Chlorothiophene-2-sulfonyl chloride (17.6 g, 81 mmol) was dissolved in 100 mL of Tetrahydrofuran (THF)

and added dropwise to the reaction mixture over 0.5 h. After 1 h the reaction mixture was allowed to warm gradually to 25° C. and stirred for 16 h. THF was removed in vacuo and then the mixture was acidified to pH of about 1 with aqueous 1 N HCl. After about 15 min, a precipitate began to crash out of the milky white mixture. After 1 h the mixture was cooled to 0° C. for 1 h and then filtered. The precipitate washed with aqueous 1 N HCl to give N-[(5-chlorothien-2-yl)sulfonyl]-5,5,5-trifluoroisoleucine as a white solid (15.2 g, 56%). Mass Spectrum (−ESI): 364 (M−H)−.

Anal: Calc'd for $C_{10}H_{11}F_3NO_4S_2$ C, 32.84; H, 3.03; N, 3.83.

Found: C, 32.45; H, 2.94; N, 3.79.

4. 5-Chloro-N-[(1S,2R)-4,4,4-trifluoro-1-(hydroxymethyl)-2-methylbutyl]thiophene-2-sulfonamide To N-[(5-chlorothien-2-yl)sulfonyl]-5,5,5-trifluoroisoleucine (15.2 g, 41.6 mmol) in THF (500 mL) at 0° C. was added a solution of 1 M borane tetrahydrofuran complex in THF (208 mL, 208 mmol) dropwise. After 15 min the reaction mixture was warmed to 25° C. and stirred for 18 h. It was then quenched slowly with a solution of 10% AcOH in MeOH (100 mL). Volatiles were removed in vacuo. The residue was then dissolved in ethyl acetate (EtOAc) (500 mL) and washed with saturated aqueous NaHCO₃ (3×100 mL), dried using sodium sulfate (Na₂SO₄), and concentrated to a white solid (13.3 g, 91% yield). Diastereomers were separated by HPLC (Luna silica gel column, 3:7 MTBE-hexane, diastereomer 1 elutes at 10.9 min, diastereomer 2 elutes at 15.3 min). Diastereomer 2 was resolved into pure enantiomers by preparative chiral SFC [chiralpak AD, 3:7 isopropanol-carbon dioxide, enantiomer 1 elutes at 4.5 min and enantiomer 2 elutes at 5.6 min]. Enantiomer 1 was then recrystallized with EtOAc/heptane, 1:4 to give 5-chloro-N-[(1S,2R)-4,4,4-trifluoro-1-(hydroxymethyl)-2-methylbutyl]thiophene-2-sulfonamide, mp 136-137° C.

$[\alpha]_D^{25}$=+45.62° (c=1% SOLUTION, MeOH). Mass Spectrum (−ESI): 350 (M−H)−.

Anal: Calc'd for $C_{10}H_{13}ClF_3NO_3S_2$ C, 34.14; H, 3.72; N, 3.98.

Found: C, 34.12; H, 3.45; N, 3.88.

B. Method 2

1. (4R)-4-Benzyl-3-(4,4,4-trifluorobutanoyl)-1,3-oxazolidin-2-one

To a solution of 4,4,4-trifluorobutyric acid (10.00 g, 70.38 mmol) in THF (150 mL) at −78° C. was added triethylamine (10.3 mL, 73.9 mmol) and pivaloyl chloride (9.1 mL, 74 mmol). The reaction mixture was warmed to 0° C. and stirred for 1.5 h. In a separate flask a solution of n-BuLi (31 mL, 2.5 M in hexane, 77 mmol) was added over 10 min to a −78° C. solution of (R)-(+)-4-benzyl-2-oxazolidinone (13.7 g, 77.4 mmol) in THF (150 mL) and the mixture was stirred for 1 hour.

The thick slurry of the mixed anhydride was cooled to −78° C., and poured through an addition funnel into the lithiated oxazolidinone solution. The mixture was allowed to warm gradually to 25° C. overnight. The mixture was then diluted with EtOAc (500 mL) and washed with aqueous 1 N HCl (500 mL), saturated aqueous NaHCO₃ (500 mL), and saturated aqueous NaCl (500 mL), then dried (Na₂SO₄) and concentrated. Flash chromatography (eluent: 1:4 EtOAc-hexane) provided (4R)-4-benzyl-3-(4,4,4-trifluorobutanoyl)-1,3-oxazolidin-2-one (18.29 g, 86%) as a colorless oil.

$[\alpha]_D^{25}$=−89.10° (c=1% SOLUTION, DMSO). Mass Spectrum (−ESI): 300 (M−H)−.

Anal: Calc'd for $C_{14}H_{14}F_3NO_3$ C, 55.82; H, 4.68; N, 4.65. Found: C, 56.03; H, 4.67; N, 4.62.

2. (4R)-4-Benzyl-3-[(2R)-4,4,4-trifluoro-2-methylbutanoyl]-1,3-oxazolidin-2-one To a solution of sodium bis(trimethylsilyl)amide (57 mL, 1.0 M in THF, 57 mmol) in THF (250 mL) at −40° C. was added (4R)-4-benzyl-3-(4,4,4-trifluorobutanoyl)-1,3-oxazolidin-2-one (15.60 g, 51.78 mmol) in THF (250 mL) dropwise over 15 min. After 1 h, iodomethane (4.2 mL, 67 mmol) was added. After 3 h, the reaction mixture was warmed to −20° C. for about 20 min. The mixture was quenched with saturated aqueous ammonium chloride (NH₄Cl) (300 mL) and then extracted with EtOAc (2×300 mL), dried using Na₂SO₄, and concentrated. Flash chromatography (eluent: 1:9 EtOAc-hexane) provided (4R)-4-benzyl-3-[(2R)-4,4,4-trifluoro-2-methylbutanoyl]-1,3-oxazolidin-2-one (12.04 g, 74%) as a colorless oil.

$[\alpha]_D^{25}$=−98.68° (c=1% SOLUTION, DMSO). Mass Spectrum (+EI): 315 (M+H)+.

Anal: Calc'd for $C_{15}H_{16}F_3NO_3$ C, 57.14; H, 5.11; N, 4.44. Found: C, 57.18; H, 5.24; N, 4.38.

3. (2R)-4,4,4-Trifluoro-2-methylbutan-1-ol

A solution of lithium borohydride (23 mL, 2.0 M in THF, 45 mmol) was added dropwise to a solution of (4R)-4-benzyl-3-[(2R)-4,4,4-trifluoro-2-methylbutanoyl]-1,3-oxazolidin-2-one (12.9 g, 40.9 mmol) and water (810 μL, 45.0 mmol) in diethyl ether (200 mL) at 0° C. The reaction mixture was allowed to warm to 25° C. and, after 1 h, was cooled to 0° C. and quenched with aqueous 1 N NaOH (124 mL). The mixture was warmed to 25° C. and stirred until both layers were homogeneous. The layers were separated and the organic extract washed with brine, dried using MgSO₄ and concentrated. Flash chromatography (eluent: 3:7 ether-petether) provided (2R)-4,4,4-trifluoro-2-methylbutan-1-ol (5.05 g, 87%) as a colorless oil. ¹H NMR was identical to that which was found in the literature (J. Med. Chem. 37: 1282-1297 (1994)).

4. (S)-N-[(3R)-Methyl-4,4,4-trifluoro-butylidene]-p-toluenesulfinamide

To (2R)-4,4,4-trifluoro-2-methylbutan-1-ol (2.90 g, 20.4 mmol) in CH₂Cl₂ (50 mL) at 0° C. was added Dess-Martin periodinane (10.24 g, 24.49 mmol). After 15 min, the reaction mixture was warmed to 25° C. and stirred for 1 h. This mixture was then diluted with diethyl ether (50 mL) and added to Na₂S₂O₃ (11.29 g, 71.44 mmol) dissolved in a saturated solution of aqueous NaHCO₃ (100 mL). The milky white mixture was stirred until both layers were homogeneous. The phases were separated and the organic extract was dried (MgSO₄) and filtered to give a solution of (2R)-4,4,4-trifluoro-2-methylbutanal which was used in the next step without removal of solvents.

To the crude aldehyde solution was added titanium (IV) ethoxide (15 mL, 20% Ti, 82 mmol) followed by (S)-(+)-toluenesulfinamide (3.48 g, 22.4 mmol) and the solution was heated to reflux for 3 h. The mixture was then cooled to 0° C. and water (75 mL) was added to precipitate titanium salts. The suspension was filtered through the Celite® reagent and the filter cake washed with CH₂Cl₂. The layers of the filtrate were separated and the aqueous layer was extracted with CH₂Cl₂. The combined organic extracts were dried using Na₂SO₄ and concentrated. Flash chromatography (eluent: 1:9 EtOAc-hexane) provided (S)-N-[(3R)-methyl-4,4,4-trifluoro-butylidene]-p-toluenesulfinamide (3.03 g, 54%) as a yellow oil. Mass Spectrum (−ESI): 276 (M−H)⁻.

5. N-[(1S,2R)-1-Cyano-4,4,4-trifluoro-2-methylbutyl]-4-methylbenzenesulfinamide To diethylaluminum cyanide (16 mL, 1.0 M in toluene, 16 mmol) in THF (40 mL) at 0° C. was added isopropanol (i-PrOH) (840 µL, 11.0 mmol). After 15 min, this solution was added to a −78° C. solution of (S)-N-[(3R)-methyl-4,4,4-trifluoro-butylidene]-p-toluenesulfinamide (3.03 g, 10.9 mmol) in THF (60 mL). After 15 min, the reaction mixture was warmed to 25° C. After 1 h, thin layer chromatography (TLC—1:9 EtOAc-hexane) indicated consumption of starting material. The mixture was cooled to −78° C. and saturated aqueous ammonium chloride (100 mL) was added. The resulting suspension was filtered through the Celite® reagent, and the filter pad washed with EtOAc (100 mL). The layers of the filtrate were separated and the aqueous layer was extracted with EtOAc. The combined organic extracts were dried using Na₂SO₄ and concentrated. The crude mixture, which according to ¹H NMR was a 1:3 mixture of diastereomers, was precipitated with diethyl ether/hexanes and the product was collected. Two additional crops of product were obtained by repeating the precipitation procedure on the concentrated filtrate. N-[(1S,2R)-1-cyano-4,4,4-trifluoro-2-methylbutyl]-4-methylbenzenesulfinamide (2.34 g, 70%) was obtained as a single diastereomer. $[\alpha]_D^{25}$=+35.46° (c=1% SOLUTION, CHCl₃). Mass Spectrum (+ESI): 305 (M+H)⁺.

Anal: Calc'd for C₁₃H₁₅F₃N₂OS C, 51.31; H, 4.97; N, 9.20.
Found: C, 51.16; H, 4.96; N, 9.08.

6. 5,5,5-Trifluoro-L-alloisoleucine hydrochloride

A suspension of N-[(1S,2R)-1-cyano-4,4,4-trifluoro-2-methylbutyl]-4-methylbenzenesulfinamide (2.34 g, 7.69 mmol) in concentrated hydrochloric acid (75 mL) was heated to reflux for 18.5 h. After cooling to 25° C., the reaction mixture washed with diethyl ether several times. The aqueous layer was concentrated to give a mixture of 5,5,5-trifluoro-L-alloisoleucine, NH₄Cl, and toluenesulfonic acid (2.35 g). The crude amino acid was used in the next step without further purification. Mass spectrum (−ESI): 309 (M−H)⁻.

7. (2S,3R)-2-Amino-5,5,5-trifluoro-3-methylpentan-1-ol

To a solution of lithium borohydride (7.7 mL, 2.0 N in THF, 15 mmol) in THF (20 mL) at 0° C. was added chlorotrimethylsilane (3.9 mL, 31 mmol). The reaction mixture was warmed to 25° C. and, after 30 min, added dropwise to a 0° C. suspension of crude amino acid hydrochloride salt (7.7 mmol) in THF (60 mL). The mixture was warmed to 25° C., and after 21 h, quenched with methanol (MeOH). The volatiles were removed in vacuo to give a residue which was dissolved in about 50 mL of aqueous 1 N NaOH, extracted with chloroform (CHCl₃) (4×75 mL), dried (Na₂SO₄) and concentrated to (2S,3R)-2-amino-5,5,5-trifluoro-3-methylpentan-1-ol as a yellow oil (1.07 g, 81%). Mass Spectrum (+ESI): 172 (M+H)⁺.

8. 5-Chloro-N-[(1S,2R)-4,4,4-trifluoro-1-(hydroxymethyl)-2-methylbutyl]thiophene-2-sulfonamide To (2S,3R)-2-amino-5,5,5-trifluoro-3-methylpentan-1-ol (1.07 g, 6.25 mmol) and triethylamine (0.87 mL, 6.2 mmol) in CH₂Cl₂ (15 mL) at 0° C. was added dropwise a solution of 5-chlorothiophene-2-sulfonylchloride (1.34 g, 6.25 mmol) in CH₂Cl₂ (15 mL). The reaction mixture was warmed to 25° C. and stirred for 24 h. It was then diluted with EtOAc (100 mL) and washed with aqueous 0.1 N HCl (50 mL) and brine (50 mL). The aqueous layer was extracted with EtOAc (50 mL). The combined organic extracts were dried using Na₂SO₄ and concentrated. Flash chromatography (eluent: 3:7 EtOAc-hexane) provided 5-chloro-N-[(1S,2R)-4,4,4-trifluoro-1-(hydroxymethyl)-2-methylbutyl]thiophene-2-sulfonamide (1.66 g, 75%) as a white solid. Recrystallization (EtOAc-heptane, 1:4) provided white needles (1.39 g, 84% recovery), mp 136-137° C.

Anal: Calc'd for C₁₀H₁₃ClF₃NO₃S₂ C, 34.14; H, 3.72; N, 3.98.
Found: C, 34.24; H, 3.97; N, 3.87.

C. Method 3

1. (4S)-4-Benzyl-3-(bromoacetyl)-1,3-oxazolidin-2-one

To a solution of S-(−)-4-benzyl-2-oxazolidinone (20.0 g, 112.86 mmol) in THF (200 mL) was added nBuLi (2.5M in hexanes, 47.4 mL, 118.51 mmol) dropwise at −78° C. The solution was stirred at −78° C. for 30 min followed by the addition of bromo acetyl bromide (25.0 g, 10.81 mL, 124.15 mmol). The solution was allowed to warm to 25° C. overnight (19 h). An aliquot was taken and TLC (1:2 EtOAc-hexane) indicated that the reaction was complete. It was diluted with ethyl acetate (200 mL) and the organic layer washed with saturated aqueous NaHCO₃ (2×50 mL). The organic layer was dried over MgSO₄, filtered and concentrated to obtain a crude brown oil (34 g). The crude product was purified by flash chromatography, eluent: 1:4 EtOAc-hexane, to furnish (4S)-4-benzyl-3-(bromoacetyl)-1,3-oxazolidin-2-one as a colorless oil (33.2 g, 98.6%). Mass Spectrum (−ESI): 297 (M−H)⁻.

2. Dimethyl-2-[(4S)-4-benzyl-2-oxo-1,3-oxazolidin-3-yl]-2-oxoethylphosphonate (4S)-4-Benzyl-3-(bromoacetyl)-1,3-oxazolidin-2-one (33.0 g, 110.68 mmol) and triethylphosphite (39.2 mL, 33.2 mmol) were heated at 120° C. for 18 h. An aliquot was taken and TLC (1:2 EtOAc-hexane) indicated that reaction was complete. The reaction was cooled to 25° C., diluted with ethyl acetate (200 mL) and the organic layer washed with saturated aqueous NaHCO₃ (2×50 mL). The organic layer was dried over MgSO₄, filtered, and concentrated to obtain dimethyl-2-[(4S)-4-benzyl-2-oxo-1,3-oxazolidin-3-yl]-2-oxoethylphosphonate as crude yellow oil (36 g, 99.3%).
Mass Spectrum (−ESI): 326 (M−H)⁻.

3. (4S)-4-Benzyl-3-[(2E)-5,5,5-trifluoropent-2-enoyl]1,3-oxazolidin-2-one

To a solution of dimethyl-2-[(4S)-4-benzyl-2-oxo-1,3-oxazolidin-3-yl]-2-oxoethylphosphonate (36 g, 109.97 mmol) in THF (200 mL) was added KHMDS (0.5M, 242 mL, 120.97 mmol), at −78° C. The solution was allowed to warm to 25° C. over 30 min and 3,3,3-trifluoropropionaldehyde (13.55 g, 120.97 mmol) was added at −20° C. The solution was allowed to warm to 25° C. overnight (19 h). An aliquot was taken and TLC (1:2 EtOAc-hexane) indicated that reaction was complete. The reaction was quenched by addition of saturated aqueous $NaHCO_3$ (50 mL). The aqueous layer was washed with ethyl acetate (3×100 mL). The organic layer was dried over $MgSO_4$, filtered and concentrated to obtain a light brown oil (32.1 g). The crude product was purified by flash chromatography, eluent: 1:6 EtOAc-hexane, to furnish (4S)-4-benzyl-3-[(2E)-5,5,5-trifluoropent-2-enoyl]1,3-oxazolidin-2-one as a colorless oil (17.7 g, 55.1%). Mass Spectrum (−ESI): 312 (M−H)⁻.

Anal: Calc'd for $C_{15}H_{14}NF_3O_3$ C, 57.51; H, 4.50; N, 4.47
Found: C, 57.05; H, 4.75; N, 4.52.

4. (4S)-4-Benzyl-3-[(3S)-5,5,5-trifluoro-3-methylpentanoyl]-1,3-oxazolidin-2-one A slurry of copper bromide (I)-dimethyl sulfide complex (9.45 g, 45.96 mmol) in THF (200 mL) and dimethyl sulfide (100 mL) as co-solvent was cooled to −40° C. and methyl magnesium bromide (30.64 mL, 91.93 mmol) was added dropwise for 10 min. The slurry was stirred for 40 min while warming to −15° C. The greenish slurry was cooled to −40° C. and (4S)-4-benzyl-3-[(2E)-5,5,5-trifluoropent-2-enoyl]1,3-oxazolidin-2-one (12 g, 38.30 mmol) was added dropwise as a solution in THF (15 mL) at −40° C. The reaction was allowed to warm to 25° C. overnight (18 h). The reaction was quenched with saturated aqueous $NH_4Cl$ (20 mL). A precipitate formed. It was filtered, the mother liquor was diluted with EtOAc (250 mL) and the organic layer washed with saturated aqueous sodium chloride (NaCl—100 mL). The organic layer was dried over $MgSO_4$, filtered and concentrated to obtain a crude semi-solid. The crude semi-solid was not soluble in $CH_2Cl_2$, MeOH, and EtOAc, partially soluble in dimethylsulfoxide (DMSO). The crude product was treated with 1N HCl (100 mL) and the aqueous layer washed with EtOAc (2×150 mL). The organic layer was dried over $MgSO_4$, filtered, concentrated to obtain a yellow oil (12.1 g). The crude product was purified by flash chromatography, eluent: 1:4 EtOAc-hexane, to furnish (4S)-4-benzyl-3-[(3S)-5,5,5-trifluoro-3-methylpentanoyl]-1,3-oxazolidin-2-one as a colorless oil (8.2 g, 67.8%).

Mass Spectrum (+ESI): 330 (M+H)⁺.
Anal: Calc'd for $C_{16}H_{18}NF_3O_3$ C, 58.36; H, 5.51; N, 4.25.
Found: C, 58.36; H, 5.70; N, 4.19.

5. (S)-3-[(2S,3R)-2-Azido-5,5,5-trifluoro-3-methylpentanoyl]-benzyl-1,3-oxazolidin-2-one A solution of (4S)-4-benzyl-3-[(3S)-5,5,5-trifluoro-3-methylpentanoyl]-1,3-oxazolidin-2-one (8.2 g, 24.90 mmol) in THF (100 mL) was cooled to −78° C. and KHMDS (potassium hexamethyldisilazane—59.7 mL, 29.88 mmol) was added dropwise over a period of 10 min. After stirring at −78° C. for 1 h, a pre-cooled (−78° C., 50 min) solution of 2,4,6-triisopropylbenzenesulfonyl azide (10.1 g, 32.37 mmol) was added via cannula over a period of 10 min. After an additional 10 min at −78° C., glacial acetic acid (6.7 mL, 112.05 mmol) was added all at once through a funnel. After 5 min at −78° C. anhydrous potassium acetate (9.77 g, 99.6 mmol) was added. The −78° C. bath was lowered and the reaction mixture was allowed to warm to 25° C. overnight (19 h). The reaction mixture was diluted with EtOAc (200 mL) and the organic phase washed with saturated aqueous potassium phosphate monobasic (2×100 mL) and saturated aqueous NaCl (100 mL). The organic layer was dried over $MgSO_4$, filtered and concentrated to obtain a yellow oil (9.5 g). The crude product was purified by flash chromatography, eluent: 1:4 EtOAc-hexane, to furnish (S)-3-[(2S,3R)-2-azido-5,5,5-trifluoro-3-methylpentanol]-4-benzyl-1,3-oxazolidin-2-one as a colorless oil (7.2 g, 73.7%). Mass Spectrum (−ESI): 342 (M−$N_2$)⁻.

6. (2S,3R)-2-Azido-5,5,5-trifluoro-3-methylpentanoic acid

To a solution of (S)-3-[(2S,3R)-2-azido-5,5,5-trifluoro-3-methylpentanol]-4-benzyl-1,3-oxazolidin-2-one (7.2 g, 19.44 mmol) in $THF:H_2O$ (3:1, 120 mL) in $N_2$ atmosphere was added lithium hydroxide (LiOH) monohydride (1.63 g, 38.88 mmol) at 0° C. The reaction was monitored by TLC (1:2 EtOAc/Hex). After 3 h, solid $NaHCO_3$ (6.0 g) was added. The slurry was diluted with saturated aqueous $NaHCO_3$ (20 mL) and $H_2O$ (40 mL) and extracted with EtOAc (3×100 mL). The organic layer was extracted with saturated aqueous $NaHCO_3$ (20 mL). The EtOAc contains the chiral auxiliary and was set aside. The combined $NaHCO_3$ layers were acidified to a pH less than 2. The acidified aqueous layer was extracted with EtOAc (3×100 mL). The organic layer was dried over $MgSO_4$, filtered and concentrated to obtain (2S,3R)-2-azido-5,5,5-trifluoro-3-methylpentanoic acid as a yellow oil (3.2 g, 98%). Mass Spectrum (−ESI): 183 (M−$N_2$)⁻.

7. 5,5,5-Trifluoro-L-alloisoleucine (2S,3R)-2-azido-5,5,5-trifluoro-3-methylpentanoic acid (3.2 g, 17.27 mmol), 10% palladium on carbon (0.79 g), glacial acetic acid (37 mL) and water (90 mL) was placed under an atmosphere of hydrogen (40 psi) and shaken on Parr hydrogenator. After 20 h, the reaction mixture was filtered through a pad of the Celite® reagent which was rinsed well with $H_2O$ (20 mL). The filtrate was concentrated under reduced pressure to produce a white solid. The solid was triturated with EtOAc (200 mL), filtered and washed once more with EtOAc (200 mL) then air dried to give 5,5,5-trifluoro-L-alloisoleucine as a white solid (2.7 g, 96%). Mass Spectrum (−ESI): 184 (M−H)⁻.

Anal: Calc'd for $C_6H_{10}NF_3O_2$+0.12 HCl C, 38.13; H, 5.50; N, 6.94.
Found: C, 38.03; H, 5.38; N, 7.39.

8. (2S,3R)-2-Amino-5,5,5-trifluoro-3-methylpentan-1-ol

To a stirring solution of lithium borohydride (14.5 mL of a 2M solution in THF, 29 mmol) at 0° C. was added chlorotrimethylsilane (7.38 mL, 58 mmol) dropwise over a period of 30 min. The ice bath was removed and the resulting slurry was stirred at 25° C. for 30 min. The reaction mixture was cooled to 0° C. and 5,5,5-trifluoro-L-alloisoleucine (2.7 g, 16.98 mmol) was added in portions as a solid over a period of 15 min. The reaction mixture was allowed to warm slowly to 25° C. as the ice bath melted. After 3 days at 25° C., the reaction mixture was cooled to 0° C., and methanol (22 mL) was carefully added over a period of 30 min. The solution was stirred at 25° C. for an additional 40 min, then concentrated under reduced pressure in a water bath at 60° C. The resulting slurry was made basic with 20% sodium hydroxide (10 mL). Water (10 mL) was added, and the entire aqueous layer was extracted with methylene chloride (100 mL) and dried over $MgSO_4$. The organic phase was filtered and evaporated to produce (2S,3R)-2-amino-5,5,5-trifluoro-3-methylpentan-1-ol as a crude oil (2.6 g, 89.6%).

Mass Spectrum (−ESI): 170 (M−H)⁻.

9. 5-Chloro-N-[(1S,2R)-4,4,4-trifluoro-1-(hydroxymethyl)-2-methylbutyl]thiophene-2-sulfonamide To a stirred solution of (2S,3R)-2-amino-5,5,5-trifluoro-3-methylpentan-1-ol (2.6 g, 15.18 mmol), triethylamine (4.2 mL, 30.38 mmol) and methylene chloride (50 mL) cooled to 0° C., was added 5-chlorothiophene-2-sulfonyl chloride (4.8 g, 18.22 mmol) as a solution in methylene chloride (5 mL), dropwise. After 15 min, the ice bath was removed and the reaction allowed to attain 25° C. overnight. The reaction was quenched by pouring it into saturated sodium bicarbonate solution (25 mL) and additional methylene chloride (150 mL). The organic phase was separated and washed sequentially with 1N HCl solution, $H_2O$, brine and dried over $MgSO_4$. The organic phase was filtered and evaporated to produce a crude oil (6.1 g) that was purified by flash chromatography using ethyl acetate-hexane, 1-6 as eluent. This produced the title compound 5-chloro-N-[(1S,2R)-4,4,4-trifluoro-1-(hydroxymethyl)-2-methylbutyl]thiophene-2-sulfonamide as a white amorphous solid (5.15 g, 96.4%). The product contained impurities. The white amorphous solid was further purified by recrystallization from 1:4 EtOAc-heptane. The mixture of solvents was added to 5-chloro-N-[(1S,2R)-4,4,4-trifluoro-1-(hydroxymethyl)-2-methylbutyl] thiophene-2-sulfonamide, heated to obtain a solution, allowed to cool to 25° C. for 3 h and then stored at 0° C. for 19 hours. A crystalline white solid precipitated, was filtered and washed with ice-cold heptane to obtain a white crystalline solid (2.7 g, 40.9%). The recrystallized material still contained impurities. The white solid (2.7 g) was further purified by prep-chiral HPLC [SFC; AD, 25×0.46 cm; mobile phase, 8:2 hexane-I-PrOH (1 mL/min)] to obtain 5-chloro-N-[(1S,2R)-4,4,4-trifluoro-1-(hydroxymethyl)-2-methylbutyl] thiophene-2-sulfonamide as a white crystalline solid, mp 132-133° C. (0.93 g, 14.1%, chiral purity 100%, analytical purity 100%). Mass Spectrum (−ESI): 350 (M−H)⁻.

Anal: Calc'd for $C_{10}H_{13}ClF_3NO_3S_2$ C, 34.14; H, 3.72; N, 3.98.

Found: C, 34.44; H, 3.70; N, 3.74.

In a comparative study between the compound of this example and a similar compound which lacks the trifluoromethyl groups and differs in the stereochemistry of the C-2 center but is otherwise identical, the compound of this example demonstrated significantly longer metabolic stability (~193 minute vs 12.7 min half-life) in an assay of Phase I rat liver microsome metabolism.

In a comparative study between the compound of this example and the corresponding analog which lacks the trifluoromethyl groups, the compound of this example demonstrated significantly longer metabolic stability in an assay of Phase 1 and 2 rat (14 min vs 2 min half-life), mouse (10 min vs 2 min half-life), human (22 min vs 13 min half-life), and dog (31 min vs 4 min) liver microsome metabolism.

Thus, the compound of the invention remains in the circulation for a longer period of time than its corresponding non-$CF_3$ analog, increasing its bioavailability.

Example 2

5-Chloro-N-[(1S,2R)-2-ethyl-4,4,4-trifluoro-1-(hydroxymethyl)butyl]thiophene-2-sulfonamide A. Method 1

1. (4S)-4-Benzyl-3-[(3S)-3-ethyl-5,5,5-trifluoropentanoyl]-1,3-oxazolidin-2-one A slurry of copper bromide (I)-dimethyl sulfide complex (1.26 g, 6.13 mmol) in THF (20 mL) and dimethyl sulfide (10 mL) as co-solvent was cooled to −40° C. and ethyl magnesium bromide (3M in diethyl ether, 4.08 mL, 12.26 mmol) was added dropwise for 10 min. The slurry was stirred for 40 min while warming to −15° C. The greenish slurry was cooled to −40° C. and (4S)-4-benzyl-3-[(2E)-5,5,5-trifluoropent-2-enoyl]1,3-oxazolidin-2-one (prepared as in Example 1: method 3, Part C) (1.6 g, 5.10 mmol) was added dropwise as a solution in THF (5 mL) at −40° C. The reaction was allowed to warm to 25° C. overnight (18 h). The reaction was quenched with saturated aqueous $NH_4Cl$ (20 mL). A precipitate formed which was filtered off. The mother liquor was diluted with EtOAc (250 mL) and the organic extract washed with saturated aqueous NaCl (100 mL). The organic extract was dried over $MgSO_4$, filtered and concentrated to obtain a crude semi-solid. The crude semi-solid was not soluble in $CH_2Cl_2$, MeOH, or EtOAc, but was partially soluble in DMSO. The crude product was treated with 1N HCl (100 mL) and the aqueous solution washed with EtOAc (2×150 mL). The organic layer was dried over $MgSO_4$, filtered and concentrated to obtain a yellow oil (1.41 g). The crude product was purified by flash chromatography, eluent: 1:4 EtOAc-hexane, to furnish (4S)-4-benzyl-3-[(3S)-3-ethyl-5,5,5-trifluoropentanoyl]-1,3-oxazolidin-2-one as a colorless oil (0.96 g, 55%). Mass Spectrum (+ESI): 344 (M+H)⁺.

Anal: Calc'd for $C_{17}H_{20}NF_3O_3$ C, 59.47; H, 5.87; N, 4.08.
Found: C, 59.58; H, 5.91; N, 4.03.

2. (S)-3-[(2S,3R)-2-Azido-3-ethyl-5,5,5-trifluoropentanol]-4-benzyl-1,3-oxazolidin-2-one To a solution of (4S)-4-benzyl-3-[(3S)-3-ethyl-5,5,5-trifluoropentanoyl]-1,3-oxazolidin-2-one (0.9 g, 2.62 mmol) in THF (10 mL) cooled to −78° C. was added dropwise over a period of 10 min KHMDS (0.5 M in toluene, 6.3 mL, 3.14 mmol). After stirring at −78° C. for 1 h, a pre-cooled (−78° C., 50 min) solution of 2,4,6-triisopropylbenzenesulfonyl azide (1.04 g, 3.38 mmol) in 20 mL of THF was added via cannula over a period of 10 min. After an additional 10 min at −78° C., glacial acetic acid (0.7 mL, 11.79 mmol) was added all at once through a funnel. After 5 min at −78° C. anhydrous potassium acetate (1.07 g, 10.48 mmol) was added. The −78° C. bath was lowered and the reaction mixture was allowed to warm to 25° C. overnight (19 h). The reaction mixture was diluted with EtOAc (200 mL) and washed with saturated aqueous potassium phosphate monobasic (2×100 mL) and saturated aqueous NaCl (100 mL). The organic layer was dried over $MgSO_4$, filtered and concentrated to obtain a yellow oil (1.09 g). The crude product was purified by flash chromatography, eluent: 1:4 EtOAc-hexane, to furnish (S)-3-[(2S,3R)-2-azido-3-ethyl-5,5,5-trifluoropentanol]-4-benzyl-1,3-oxazolidin-2-one as a colorless oil (0.587 g, 59%). Mass Spectrum (−ESI): 357 (M−$N_2$)⁻.

3. (2S,3R)-2-Azido-3-ethyl-5,5,5-trifluoropentanoic acid

To a solution of (S)-3-[(2S,3R)-2-azido-3-ethyl-5,5,5-trifluoropentanol]-4-benzyl-1,3-oxazolidin-2-one (287 mg, 0.746 mmol) in THF:H$_2$O (3:1, 4 mL) under a N$_2$ atmosphere was added LiOH monohydrate (62.66 mg, 1.49 mmol) at 0° C. The reaction was monitored by TLC (1:2 EtOAc/Hex), after 3 h, solid NaHCO$_3$ (1.0 g) was added. The slurry was diluted with saturated aqueous NaHCO$_3$ (2 mL) and H$_2$O (4 mL) and extracted with EtOAc (3×50 mL). The organic layer was extracted with saturated aqueous NaHCO$_3$ (10 mL). The EtOAc contains the chiral auxiliary and was set aside. The combined aqueous extracts were acidified to a pH of less than 2, extracted with EtOAc (3×50 mL), dried over MgSO$_4$, filtered and concentrated to obtain (2S,3R)-2-azido-3-ethyl-5,5,5-trifluoropentanoic acid as a yellow oil (130 mg, 94%). Mass Spectrum (−ESI): 197 (M−N$_2$)$^−$.

4. (2S,3R)-2-Amino-3-ethyl-5,5,5-trifluoropentan-1-ol

To a gray slurry of lithium aluminum hydride (LAH—110.6 mg, 2.91 mmol) in THF (2 mL) at 0° C. was added dropwise over 5 min (2S,3R)-2-azido-3-ethyl-5,5,5-trifluoropentanoic acid (130 mg, 583 mmol). The resulting slurry was allowed to warm to 25° C. for 19 h. The reaction was quenched by sequential addition of H$_2$O (0.5 mL), 1N NaOH (1.5 mL) and H$_2$O (0.5 mL) at 0° C. The white precipitate that formed after 5 h was filtered off, the organic solvent was dried over MgSO$_4$, filtered and concentrated to obtain (2S,3R)-2-amino-3-ethyl-5,5,5-trifluoropentan-1-ol as a crude oil (120 mg, 96%). Mass Spectrum (+ESI): 186 (M+H)$^+$.

5. 5-Chloro-N-[(1S,2R)-2-ethyl-4,4,4-trifluoro-1-(hydroxymethyl)butyl]thiophene-2-sulfonamide To a stirred solution of (2S,3R)-2-amino-3-ethyl-5,5,5-trifluoropentan-1-ol (120 mg, 0.701 mmol), triethylamine (0.1 mL, 1.4 mmol) and methylene chloride (50 mL) cooled to 0° C., was added 5-chlorothiophene-2-sulfonyl chloride (220 mg, 0.841 mmol) as a solution in methylene chloride (5 mL), dropwise. After 15 min, the ice bath was removed and the reaction was allowed to attain 25° C. overnight. Additional methylene chloride (15 mL) was added and the reaction mixture was poured into saturated sodium bicarbonate solution (25 mL). The organic phase was separated and washed sequentially with 1N HCl solution, H$_2$O, brine and dried over MgSO$_4$. The organic phase was filtered and evaporated to produce a crude oil (0.36 g) that was purified by flash chromatography using ethyl acetate-hexane, 1-4 as eluent. This provided the title compound 5-chloro-N-[(1S,2R)-2-ethyl-4,4,4-trifluoro-1-(hydroxymethyl)butyl]thiophene-2-sulfonamide as an oil (125 mg, 53%). The oil (125 mg) was further purified by prep-chiral HPLC [SFC; AD, 25×0.46 cm; mobile phase, 8:2 hexane-ipa (1 mL/min)] to obtain 5-chloro-N-[(1S,2R)-2-ethyl-4,4,4-trifluoro-1-(hydroxymethyl)butyl]thiophene-2-sulfonamide as a white crystalline solid (0.15 mg, 6.4%, chiral purity 100%, analytical purity 100%). Mass Spectrum (−ESI): 364 (M−H)$^−$.

Anal: Calc'd for C$_{11}$H$_{15}$NClF$_3$O$_3$S$_2$+0.24 C$_4$H$_8$O$_2$ C, 37.50; H, 4.08; N, 3.73.

Found: C, 37.12; H, 4.41; N, 3.62.

B. Method 2

1. 2-Ethyl-4,4,4-trifluorobutyric acid

A solution of diisopropylamine (17.1 g, 169 mmol) in THF (180 mL) was stirred under nitrogen at 0° C. n-Butyl lithium (n-BuLi—67.6 mL, 2.5 M in hexane) was added dropwise over 15 min and the resulting solution stirred for 0.5 h at 0° C. After this time period, the reaction was cooled to −78° C., and 4,4,4-trifluorobutyric acid (10.0 g, 70.4 mmol) in THF (20 mL) was added dropwise over 0.5 h. The resulting solution was stirred for an additional 0.5 h at −78° C. After this time period, ethyl iodide (6.19 mL, 77.4 mmol) was added dropwise over 15 min. The resulting solution was stirred for 15 min. at −78° C. then warmed to 25° C. for 24 h. After this time period, the reaction mixture was quenched by slow addition of H$_2$O (~20 mL). After concentration, the residue was acidified to pH 1 with 2 N aq. HCl and then extracted with Et$_2$O (400 mL). The organic layer was then dried using MgSO$_4$. After concentration, the resulting residue was used directly in the next reaction without further purification.

2. 2-Ethyl-4,4,4-trifluorobutanol

A solution of LAH (2.74 g, 72.3 mmol) in Et$_2$O (230 mL) was stirred under nitrogen at 0° C. 2-Ethyl-4,4,4-trifluorobutyric acid (12.3 g, 72.3 mmol) in Et$_2$O (20 mL) was added dropwise, and the solution stirred for 15 min at 0° C. and then 2 h at 25° C. After this time period, the solution was quenched with the dropwise addition of H$_2$O (2.74 mL), 15% NaOH (2.74 mL), and H$_2$O (8.22 mL) with efficient stirring. Solid Na$_2$SO$_4$ was added to dry the solvent, and the resulting mixture was stirred for 1 h. The resulting slurry was filtered, and the filter cake washed with excess Et$_2$O. After concentration, the crude product was purified by the Biotage Flash™ 40 chromatography instrument, eluent: 20:80 to 30:70 Et$_2$O:PE to obtain 2-ethyl-4,4,4-trifluorobutanol as an oil (6.18 g, 55% yield for two steps).

3. 2-Ethyl-4,4,4-trifluorobutyl aldehyde

A solution of 2-ethyl-4,4,4-trifluorobutanol (6.18 g, 39.6 mmol) in CH$_2$Cl$_2$ (50 mL) was stirred under nitrogen at 0° C. Dess-Martin periodinane reagent (20.16 g, 47.5 mmol) was added in one portion and the solution stirred for 1 h at 0° C. After an additional 5 h at 25° C., the reaction was complete by NMR. The solution was diluted with Et$_2$O (100 mL), and to this solution was added Na$_2$S$_2$O$_3$ (55 g) in sat. aq. NaHCO$_3$ (100 mL). The resulting mixture was stirred for 0.5 h. The liquid layers were separated and the organic layer washed with additional sat. aq. NaHCO$_3$ (50 mL) and brine (50 mL) and then dried using Na$_2$SO$_4$. Most of the solvent was removed via distillation using a Vigreux column (flask heated at about 50 to about 55° C. and head temperature equal to about 38° C.). The resulting residue in the reaction flask was used directly in the next reaction without further purification (aldehyde very volatile).

4. 5-(1-Ethyl-3,3,3-trifluoropropyl)-imidazolidine-2,4-dione

A solution of crude 2-ethyl-4,4,4-trifluorobutyl aldehyde (6.10 g, 39.6 mmol) in H$_2$O (100 mL) was stirred at 0° C. To this solution was added sodium cyanide (5.82 g, 119 mmol), ammonium carbonate (15.2 g, 158 mmol), and EtOH (100 mL). The reaction mixture was heated to 90° C. for 3 days. After cooling to 25° C. and concentration, the resulting residue was acidified to a pH of about 1 to about 2 with concentrated HCl. The solid which formed was filtered off, washed with 2 N HCl and excess H$_2$O, and then dried on the vacuum pump overnight to afford 5-(1-ethyl-3,3,3-trifluoropropyl)-imidazolidine-2,4-dione (2.74 g, 31% yield for two steps). Mass Spectrum (+ESI): 225 (M+H)$^+$ and (−ESI): 223 (M−H)$^−$

5. 2-[(5'-Chloro-2'-thienyl)sulfonylamino]-3-ethyl-5,5,5-trifluoropentanoic acid A solution of 5-(1-ethyl-3,3,3-trifluoropropyl)-imidazolidine-2,4-dione (1.76 g, 7.85 mmol) in 20 mL of aq. NaOH (1.26 g, 31.4 mmol) was heated by microwave in a sealed vessel for 0.5 h (Microwave conditions: 15 min. at about 100% power, 150° C., 50 psi; then 5 min. 0% power; then 15 min. at about 100% power, 150° C., 50 psi). After cooling to 25° C., water and ammonia were removed from the reaction mixture in-vacuo, and the resulting crude amino acid sodium salt mixture was dissolved in H$_2$O (15 mL). To this solution at 0° C. was added THF (25 mL) followed by 5-chloro-thiophene-2-sulfonyl chloride (1.87 g, 8.64 mmol) in THF (5 mL) dropwise. After 18 h at 25° C., the reaction was concentrated and the residue was acidified to a pH of 1 with 2 N aqueous HCl. This aqueous layer was extracted with Et$_2$O (2×100 mL), and the resulting organic layer washed with brine (20 mL) and dried using MgSO$_4$. After concentration, the crude residue was recrystallized from EtOAc:hexane to remove by-products. Concentration of the filtrate afforded the product as a solid (1.31 g, 44%).

Mass Spectrum (+ESI): 380 (M+H)$^+$ and (−ESI): 378 (M−H)$^−$

6. 5'-Chloro-N-[(1S,2R)-2-ethyl, 4,4,4-trifluoro-1-(hydroxymethyl)butyl]thiophene-2'-sulfonamide A solution of 2-[(5'-chloro-2'-thienyl)sulfonylamino]-3-ethyl-5,5,5-trifluoropentanoic acid (2.19 g, 5.77 mmol) in THF (60 mL) was stirred under nitrogen at 25° C. Borane-THF complex (23.1 mL, 1.0 M in THF) was added dropwise, and the resulting solution stirred for 18 h at 25° C. After this time period, the reaction was complete by TLC (10:90 MeOH:CHCl$_3$). The reaction mixture was quenched by slow addition of 10% acetic acid (HOAc) in MeOH (80 mL). After concentration, the residue was dissolved in EtOAc (200 mL) and washed with saturated aqueous NaHCO$_3$ (3×20 mL) and brine (20 mL), and then dried using Na$_2$SO$_4$. After concentration, the crude product (2.20 g) was purified by the Biotage Flash™ 40 chromatography system, eluent: 20:80 to 30:70 EtOAc:PE to obtain one of two pairs of racemic mixtures (0.623 g). This compound was then further purified using chiral HPLC conditions (the Chiralcel™ AD column; 25×2.2 cm, 254 nm, 0.5 mL injections; mobile phase: 25 mL/min 12% MeCN in hexane; product is peak one, R$_t$=6.7, >99.9% purity) to afford enantiomerically pure 5'-chloro-N-[(1S,2R)-2-ethyl, 4,4,4-trifluoro-1-(hydroxymethyl)butyl]thiophene-2'-sulfonamide as a white solid, mp 128-129° C. (0.238 g, 45% yield related to specific enantiomer). Mass Spectrum (−ESI): 364 (M−H)$^−$.

Anal: Calc'd for C$_{11}$H$_{15}$ClF$_3$NO$_3$S$_2$ C, 36.12; H, 4.13; N, 3.83.

Found: C, 36.22; H, 4.20; N, 3.78.

Example 3

5'-Chloro-N-[(1S,2R)-2-ethyl, 4,4,4-trifluoro-1-(1-hydroxyethyl)butyl]thiophene-2'-sulfonamide

A. 5'-Chloro-N-[(1S,2R)-2-ethyl, 4,4,4-trifluoro-1-(formyl)butyl]thiophene-2'-sulfonamide A solution of 5'-chloro-N-[(1S,2R)-2-ethyl, 4,4,4-trifluoro-1-(hydroxymethyl)butyl]thiophene-2'-sulfonamide (prepared as in Example 2, 0.100 g, 0.273 mmol) in CH$_2$Cl$_2$ (4 mL) was stirred under nitrogen at 0° C. Dess-Martin periodinane reagent (0.151 g, 0.355 mmol) was added in one portion and the solution stirred for 1 h at 0° C. After an additional 1 h at 25° C., the reaction was complete by TLC (30:70 EtOAc:PE). The solution was diluted with Et$_2$O (50 mL), and to this solution was added Na$_2$S$_2$O$_3$ (0.363 g) in saturated aqueous NaHCO$_3$ (10 mL). The resulting mixture was stirred for 0.5 h. The liquid layers were separated, and the organic layer washed with additional sat. aq. NaHCO$_3$ (5 mL) and brine (5 mL) and then dried (Na$_2$SO$_4$). After concentration, the crude product was purified by preparatory plate chromatography, eluent: 30:70 EtOAc:PE to obtain 5'-chloro-N-[(1S,2R)-2-ethyl, 4,4,4-trifluoro-1-(formyl)butyl]thiophene-2'-sulfonamide as a solid (0.036 g, 36%).

B. 5'-Chloro-N-[(1S,2R)-2-ethyl, 4,4,4-trifluoro-1-(1-hydroxyethyl)butyl]thiophene-2'-sulfonamide A solution of 5'-chloro-N-[(1S,2R)-2-ethyl, 4,4,4-trifluoro-1-(formyl)butyl]thiophene-2'-sulfonamide (0.035 g, 0.0962 mmol) in THF (3 mL) was stirred under nitrogen at 0° C. Methyl magnesium bromide (0.206 mL, 1.4 M in toluene:THF) was added dropwise and the resulting solution was stirred for 1 h at 25° C. After this time period, the reaction was complete by TLC (30:70 EtOAc:PE). The solution was quenched with saturated aqueous NH$_4$Cl (2 mL) and extracted with Et$_2$O (20 mL). The organic layer washed with brine (3 mL) and then dried using Na$_2$SO$_4$. After concentration, the crude product was purified by preparatory plate chromatography, eluent: 30:70 EtOAc:PE to obtain 5'-chloro-N-[(1S,2R)-2-ethyl, 4,4,4-trifluoro-1-(1-hydroxyethyl)butyl]thiophene-2'-sulfonamide as an off-white solid (0.027 g, 73%). Mass Spectrum (−ESI): 378 (M−H)$^−$.

Anal: Calc'd for C$_{12}$H$_{17}$ClF$_3$NO$_3$S$_2$ C, 37.94; H, 4.51; N, 3.69.

Found: C, 38.35; H, 4.32; N, 3.29.

Example 4

5'-Chloro-N-[3,3,3-trifluoro-2-(trifluoromethyl)-1-(hydroxymethyl)propyl]thiophene-2'-sulfonamide

A. 3,3,3-Trifluoro-2-(trifluoromethyl)-1-(hydroxymethyl)propylamine

A solution of 4,4,4,4',4',4'-hexafluoro-DL-valine (0.500 g, 2.22 mmol) in THF (20 mL) was stirred under nitrogen at 25° C. Borane-THF complex (6.66 mL, 1.0 M in THF) was added dropwise and the resulting solution stirred for 4 h at 25° C. After this time period, the reaction was complete by TLC (10:2:1 EtOAc:EtOH:H$_2$O). The reaction mixture was quenched by slow addition of 10% HOAc in MeOH (23 mL). After concentration, the residue was dissolved in Et$_2$O (200 mL) and washed with saturated aqueous NaHCO$_3$ (3×20 mL) and brine (20 mL), and then dried using Na$_2$SO$_4$. After concentration, the resulting residue was used directly in the next reaction without further purification.

B. 5'-Chloro-N-[3,3,3-trifluoro-2-(trifluoromethyl)-1-(hydroxymethyl)propyl]thiophene-2'-sulfonamide A solution of 3,3,3-trifluoro-2-(trifluoromethyl)-1-(hydroxymethyl)propylamine (0.400 g, 1.89 mmol) in $CH_2Cl_2$ (20 mL) was stirred under nitrogen at 0° C. Triethylamine ($Et_3N$—0.369 mL, 2.65 mmol) was added dropwise followed by 5-chloro-thiophene-2-sulfonyl chloride (0.492 g, 2.27 mmol) in one portion, and the resulting solution was stirred for 18 h at 25° C. After this time period, the reaction was complete by TLC (30:70 EtOAc:PE). After quenching with MeOH and concentration, the residue was taken up in $Et_2O$ (200 mL) and washed with 1 N aqueous HCl (20 mL), saturated aqueous $NaHCO_3$ (20 mL), and brine (20 mL), and then dried ($MgSO_4$). After concentration, the crude product was purified by the Biotage Flash™ 40 chromatography system, eluent: 10:90 to 30:70 EtOAc:PE to obtain 5'-chloro-N-[3,3,3-trifluoro-2-(trifluoromethyl)-1-(hydroxymethyl)propyl]thiophene-2'-sulfonamide as an off-white solid (0.108 g, 14% yield for two steps, racemic mixture). Mass Spectrum (–ESI): 390 (M–H)⁻.

Anal: Calc'd for $C_9H_8ClF_6NO_3S_2$ C, 27.59; H, 2.06; N, 3.58;

Found: C, 28.24; H, 1.90; N, 3.48.

Example 5

5'-Chloro-N-[3,3,3-trifluoro-2-(trifluoromethyl)-1-S-(hydroxymethyl)propyl]thiophene-2'-sulfonamide

A. Methyl 2-amino-3-(trifluoromethyl)-4,4,4-trifluorobutanoate

A solution of 4,4,4,4',4',4'-hexafluoro-DL-valine (2.00 g, 8.89 mmol) in $CH_2Cl_2$:MeOH (4:1, 50 mL) was stirred under nitrogen at 0° C. Tetramethylsilane (TMS) diazomethane (5.33 mL, 2.0 M in hexane) was added dropwise, and the resulting solution stirred for 3 h at 25° C. After this time period, the reaction was complete by TLC (10% MeOH:chloroform). After concentration, the resulting residue (1.34 g, 63%) was used directly in the next reaction without further purification.

B. Methyl 2-[(5'-chloro-2'-thienyl)sulfonylamino]-3-trifluoromethyl-4,4,4-trifluorobutanoate A solution of methyl 2-amino-3-(trifluoromethyl)-4,4,4-trifluorobutanoate (1.34 g, 5.60 mmol) in $CH_2Cl_2$ (10 mL) was stirred under nitrogen at 25° C. Pyridine (10 mL, 126 mmol) was added dropwise followed by 5-chloro-thiophene-2-sulfonyl chloride (1.82 g, 8.40 mmol) in one portion and the resulting solution stirred for 72 h at 25° C. After this time period, the reaction was complete by TLC (20:80 EtOAc:PE). After quenching with $H_2O$, the mixture was diluted with $Et_2O$ (200 mL). The organic layer was washed with 1 N aq. HCl (20 mL), sat. aq. $NaHCO_3$ (20 mL), and brine (20 mL) and then dried ($MgSO_4$). After concentration, the crude product was purified by the Biotage Flash™ 40 chromatography system, eluent: 5:95 to 25:75 EtOAc:PE to obtain methyl 2-[(5'-Chloro-2'-thienyl)sulfonylamino]-3-trifluoromethyl-4,4,4-trifluorobutanoate as a solid (1.61 g, 69%). Mass Spectrum (–ESI): 418 (M–H)⁻.

C. 5'-Chloro-N-[3,3,3-trifluoro-2-(trifluoromethyl)-1-S-(hydroxymethyl)propyl]thiophene-2'-sulfonamide A slurry of LAH (0.146 g, 3.84 mmol) in $Et_2O$ (17 mL) was stirred under nitrogen at 0° C. To this mixture was added dropwise methyl 2-[(5'-chloro-2'-thienyl)sulfonylamino]-3-trifluoromethyl-4,4,4-trifluorobutanoate (1.61 g, 3.84 mmol) in $Et_2O$ (3 mL). After stirring at this temperature for 0.25 h, the reaction was complete by TLC (30:70 EtOAc:PE). This mixture (with efficient stirring) was quenched with the dropwise addition of $H_2O$ (0.146 mL), 15% aqueous NaOH (0.146 mL), and $H_2O$ (0.438 mL) and then stirred an additional 2 h at 25° C. The resulting slurry was dried ($Na_2SO_4$) and then filtered. After concentration, the crude product was purified by the Biotage Flash™ 40 chromatography system, eluent: 5:95 to 40:60 EtOAc:PE to obtain 5'-chloro-N-[3,3,3-trifluoro-2-(trifluoromethyl)-1-(hydroxymethyl)propyl]thiophene-2'-sulfonamide as a solid (0.590 g, 39%, racemic mixture). The active enantiomer, 5'-chloro-N-[3,3,3-trifluoro-2-(trifluoromethyl)-1-S-(hydroxymethyl)propyl]thiophene-2'-sulfonamide (0.185 g), was then isolated as an off-white solid (mp 148-150° C.) using chiral HPLC [the Chiralpak® AS column; 2×25 cm, 254 nm, 0.5 mL injections; mobile phase: 15 mL/min 8% IPA in hexane/0.1% TFA (premix); product is peak two, $R_f$=12.3, 98.5% purity]. Mass Spectrum (–ESI): 389.9 (M–H)⁻.

Anal: Calc'd for $C_9H_8ClF_6NO_3S_2$ C, 27.59; H, 2.06; N, 3.58;

Found: C, 27.76; H, 1.96; N, 3.47.

In a comparative study between the compound of this example and a similar compound which lacks the trifluoromethyl groups but is otherwise identical, the compound of this example demonstrated significantly higher (about 72 to about 133 fold) potency in a cellular assay and significantly longer metabolic stability (46 min vs 10 min half-life in an assay of transgenic mice (Tg2576) liver microsome metabolism). Thus, the compound of the invention may be used in lower doses than the corresponding compounds lacking the trifluoromethyl groups.

Example 6

5-Chloro-N-[(1R,2S)-2-ethyl-4,4,4-trifluoro-1-(hydroxymethyl)butyl]thiophene-2-sulfonamide

A. (4R)-4-Benzyl-3-(bromoacetyl)-1,3-oxazolidin-2-one

To a solution of R-(–)-4-benzyl-2-oxazolidinone (15.0 g, 84.65 mmol) in THF (200 mL) was added nBuLi (2.5M in hexanes, 34 mL, 84.65 mmol) dropwise at –78° C. The solution was stirred at –78° C. for 30 min and then bromo acetyl bromide (18.65 g, 7.8 mL, 124.15 mmol) was added. The solution was allowed to warm to 25° C. overnight (19 h). An aliquot was taken and TLC (1:2 EtOAc-hexane) indicated that reaction was complete. It was diluted in ethyl acetate (200 mL) and the organic layer washed with saturated aqueous $NaHCO_3$ (2×50 mL). The organic layer was dried over $MgSO_4$, filtered and concentrated to obtain a crude brown oil (24.6 g). The crude product was purified by flash chromatography, eluent: 1:4 EtOAc-hexane, to furnish (4R)-4-benzyl-3-(bromoacetyl)-1,3-oxazolidin-2-one as a colorless oil (19.9 g, 79.6%).

Mass Spectrum (+ESI): 300, 299 (M+H)⁺.

B. Diethyl-2-[(4R)-4-benzyl-2-oxo-1,3-oxazolidin-3-yl]-2-oxoethylphosphonate (4R)-4-Benzyl-3-(bromoacetyl)-1,3-oxazolidin-2-one (19.7 g, 66.07 mmol) and triethylphosphite (33.99 mL, 198.2 mmol) were heated at 120° C. for 18 h. An aliquot was taken and TLC (1:2 EtOAc-hexane) indicated that reaction was complete. The reaction was cooled to 25° C., diluted with ethyl acetate (200 mL). The organic layer washed with saturated aqueous $NaHCO_3$ (2×50 mL), dried over $MgSO_4$, filtered, and concentrated to obtain diethyl-2-[(4R)-4-benzyl-2-oxo-1,3-oxazolidin-3-yl]-2-oxoethylphosphonate as crude yellow oil (14.27 g, 60.77%). Mass Spectrum (−ESI): 326 (M−H)⁻.

C. (4R)-4-Benzyl-3-[(2E)-5,5,5-trifluoropent-2-enoyl]1,3-oxazolidin-2-one

To a solution of diethyl-2-[(4R)-4-benzyl-2-oxo-1,3-oxazolidin-3-yl]-2-oxoethylphosphonate (14.27 g, 40.17 mmol) in THF (200 mL) was added KHMDS (0.5M, 88 mL, 44.63 mmol), at −78° C. The solution was allowed to warm to 25° C. over 30 min and 3,3,3-trifluoropropionaldehyde (5.0 g, 44.63 mmol) was added at −20° C. The solution was allowed to warm to 25° C. overnight (19 h). An aliquot was taken and TLC (1:2 EtOAc-hexane) indicated that reaction was complete. The reaction was quenched by addition of saturated aqueous $NaHCO_3$ (50 mL). The aqueous layer was washed with ethyl acetate (3×100 mL). The organic layer was dried over $MgSO_4$, filtered and concentrated to obtain a light brown oil (32.1 g). The crude product was purified by flash chromatography, eluent: 1:6 EtOAc-hexane, to furnish (4R)-4-benzyl-3-[(2E)-5,5,5-trifluoropent-2-enoyl]-1,3-oxazolidin-2-one as a colorless oil (3.7 g, 29.4%).

Mass Spectrum (+ESI): 314 (M+H)⁺.

Anal: Calc'd for $C_{15}H_{14}NF_3O_3+0.25H_2O$ C, 56.70; H, 4.60; N, 4.41

Found: C, 56.44; H, 4.49; N, 4.41.

D. (4R)-4-Benzyl-3-[(2R,3S)-2-bromo-3-ethyl-5,5,5-trifluoropentanoyl]-1,3-oxazolidin-2-one A slurry of copper bromide (I)-dimethyl sulfide complex (1.57 g, 7.66 mmol) in THF (20 mL) and dimethyl sulfide (10 mL) as co-solvent was cooled to −40° C. and ethyl magnesium bromide (5 mL, 15.3 mmol) was added dropwise for 10 min. The slurry was stirred for 40 min while warming to −15° C. The greenish slurry was cooled to −40° C. and (4R)-4-benzyl-3-[(2E)-5,5,5-trifluoropent-2-enoyl]1,3-oxazolidin-2-one (2 g, 6.38 mmol) was added dropwise as a solution in THF (5 mL) at −40° C. The reaction was allowed to warm to 25° C. overnight (20 h). The black slurry was cooled down to −78° C. and N-bromosuccinimide (2.3 g 12.76 mmol) was added portionwise. It was allowed to warm to −40° C. and stirred for an additional 30 min. After this period, the black slurry became greenish to blue. A precipitate formed and was filtered off. The mother liquor was diluted with EtOAc (150 mL) and the organic layer washed with saturated NaCl (50 mL). The organic layer was dried over $MgSO_4$, filtered and concentrated to afford (4R)-4-benzyl-3-[(2R,3S)-2-bromo-3-ethyl-5,5,5-trifluoropentanoyl]-1,3-oxazolidin-2-one as a green semi-solid (1.6 g, 59.5%). Mass Spectrum (−ESI): 421, 420 (M−H)⁻.

E. (4R)-3-[(2S,3S)-2-Azido-3-ethyl-5,5,5-trifluoropentanoyl]-4-benzyl-1,3-oxazolidin-2-one To a solution of (4R)-4-benzyl-3-[(2R,3S)-2-bromo-3-ethyl-5,5,5-trifluoropentanoyl]-1,3-oxazolidin-2-one (1.6 g, 3.79 mmol) in DMF (20 mL) was added sodium azide (0.468 g, 7.199 mmol). The slurry was stirred at 25° C. for 20 h and the solvent was removed in vacuo. The crude product was dissolved in EtOAc (100 mL) and the organic phase washed with $H_2O$ (3×20 mL) and saturated aqueous NaCl (20 mL). The organic layer was dried over $MgSO_4$, filtered and concentrated to obtain a yellow oil (1.4 g). The crude product was purified by flash chromatography, eluent: 1:4 EtOAc-hexane, to furnish (4R)-3-[(2S,3S)-2-azido-3-ethyl-5,5,5-trifluoropentanoyl]-4-benzyl-1,3-oxazolidin-2-one as a colorless oil (1.21 g, 83.2%). Mass Spectrum (−ESI): 357 (M−$N_2$)⁻, 380, 381.

F. (2S,3S)-2-Amino-3-ethyl-5,5,5-trifluoropentan-1-ol

To a gray slurry of LAH (100 mg, 2.65 mmol) in THF (3 mL) at −10° C. was added (4R)-3-[(2S,3S)-2-azido-3-ethyl-5,5,5-trifluoropentanoyl]-4-benzyl-1,3-oxazolidin-2-one (300 mg, 0.78 mmol) as a solution in THF (2 mL) dropwise over 5 min. The resulting slurry was allowed to warm to 25° C. for 19 h. The reaction was quenched by sequential addition of $H_2O$ (0.3 mL), 1N NaOH (0.9 mL) and $H_2O$ (0.3 mL) at 0° C. The precipitate that formed after 5 h was filtered off. The mother liquor was dried over $MgSO_4$, filtered and concentrated to obtain (2S,3S)-2-amino-3-ethyl-5,5,5-trifluoropentan-1-ol as a light yellow oil (145 mg, 98%). Mass Spectrum (−ESI): 184 (M−H)⁻.

G. 5-Chloro-N-[(1S,2S)-2-ethyl-4,4,4-trifluoro-1-(hydroxymethyl)butyl]thiophene-2-sulfonamide To a stirred solution of (2S,3S)-2-amino-3-ethyl-5,5,5-trifluoropentan-1-ol (145 mg, 0.78 mmol), triethylamine (0.22 mL, 1.56 mmol) and methylene chloride (5 mL) cooled to 0° C., was added 5-chlorothiophene-2-sulfonyl chloride (225 mg, 0.861 mmol) as a solution in methylene chloride (5 mL), dropwise. After 15 min, the ice bath was removed and the reaction mixture was allowed to attain 25° C. overnight. Additional methylene chloride (15 mL) was added and the reaction was quenched by pouring it into saturated sodium bicarbonate solution (25 mL). The organic phase was separated and washed sequentially with 1N HCl solution, $H_2O$, brine and dried over $MgSO_4$. The organic phase was filtered and evaporated to produce a crude oil (0.250 g) that was purified via flash chromatography, eluent: 1:6 ethyl acetate-hexane. This produced the title compound 5-chloro-N-[(1S,2S)-2-ethyl-4,4,4-trifluoro-1-(hydroxymethyl)butyl]thiophene-2-sulfonamide as an oil (140 mg, 53.8%). The crude oil was further purified by recrystallization from 1:4 EtOAc-heptane. The mixed solvent system was added to 5-chloro-N-[(1S,2S)-4,4,4-trifluoro-1-(hydroxymethyl)-2-methylbutyl]thiophene-2-sulfonamide, heated to obtain a solution, allowed to cool to 25° C. for 3 h and then stored at 0° C. for 19 h. A crystalline white solid precipitated which was filtered and washed with ice-cold heptane to afford 5-chloro-N-[(1R,2S)-2-ethyl-4,4,4-trifluoro-1-(hydroxymethyl)butyl]thiophene-2-sulfonamide as a white crystalline solid (50 mg, 19.2%, chiral purity 91%, analytical purity 100%). Mass Spectrum (−ESI): 364 (M−H)⁻.

Anal: Calc'd for $C_{11}H_{15}NClF_3O_3S_2+0.10\ C_4H_8O_2$ C, 36.55; H, 4.25; N, 3.74.

Found: C, 36.94; H, 4.15; N, 3.57.

Example 7

5-Chloro-N-[4,4,4-trifluoro-1-(hydroxymethyl)butyl]thiophene-2-sulfonamide

A. 4,4,4-Trifluorobutanal

Diisobutylaluminum hydride (35 mL, 35.26 mmol) was added to a solution of ethyl-4,4,4-trifluorobutanoate (5 g, 29.38 mmol) in $CH_2Cl_2$ (50 mL) under $N_2$ atmosphere at $-70°$ C. After 6 h, 1N HCl (6 mL) was added and after warming to $-60°$ C., the reaction mixture was poured into $H_2O$ (5 mL) and extracted with $CH_2Cl_2$ (2×50 mL). The combined organic extracts were washed with $H_2O$ (2×0 mL). The organic extracts were dried over $MgSO_4$, filtered and concentrated to obtain 4,4,4-trifluorobutanal as a colorless non-viscous oil (3.7 g, 100%).

B. 5-(3,3,3-Trifluoropropyl)imidazolidine-2,4-dione

Sodium cyanide (4.31 g, 88.04 mmol) and 4,4,4-trifluorobutanal (3.7 g, 29.34 mmol) were added to ammonium carbonate (9.1 g, 117.4 mmol) in $H_2O$ (60 mL). The black reaction mixture was heated to 90° C. After 1 h, the mixture became homogeneous and it was stirred at 90° C. for 18 h. After cooling to 25° C., about 60 mL of solvent was removed in vacuo. Concentrated HCl (4 mL) was added to acidify the mixture to a pH of about 2 and a precipitate formed. It was filtered. The mother liquor washed with EtOAc (3×50 mL). The organic layer was dried over $MgSO_4$, filtered and concentrated to obtain 5-(3,3,3-trifluoropropyl)imidazolidine-2,4-dione as a brown oil (3.95 g, 69.7%). Mass Spectrum $(-ESI)$: 195 $(M-H)^-$.

C. 5,5,5-Trifluoronorvaline 5-(3,3,3-trifluoropropyl)imidazolidine-2,4-dione (0.9 g, 4.59 mmol) was dissolved in a 10 mL solution of aqueous NaOH (0.734 g in 10 mL $H_2O$, 18.35 mmol). The solution was divided in 2 special vessels for microwave technology. The solution was heated by microwave in sealed vessels for 1 h. Microwave conditions: 15 min at about 100% power, 150° C., 50 psi, then 5 min at rest, 0% power. Repeat sequence twice or until reaction is done. Water and ammonia were removed from the reaction mixture in vacuo and the resulting crude 5,5,5-trifluoronorvaline (1.1 g, 140%) and NaOH mixture was used in the next reaction without further purification. Mass Spectrum $(+ESI)$: 172 $(M+H)^+$.

D. N-[(5-Chlorothien-2-yl)sulfonyl]-5,5,5-trifluoronorvaline

To a solution of the crude 5,5,5-trifluoronorvaline (0.785 g, 4.59 mmol) and NaOH mixture dissolved in THF (10 ml) and 2N NaOH (10 mL) was added dropwise a solution of 5-chlorothiophene-2-sulfonyl chloride (1.32 g, 5.04 mmol) in THF (10 ml) over 30 min. After 60 min, the reaction mixture was allowed to warm gradually to 25° C. and stirred for 16 h. THF was removed in vacuo and the mixture was acidified to a pH of about 2 with 1N HCl. After 15 min, a precipitate began to crash out of the milky white solution. After 60 min, the mixture was cooled to 0° C. for 45 min and then filtered. The precipitate washed with 1N HCl (10 mL) to provide a white solid. The white solid gummed out. It was dissolved in EtOAc (100 mL). The aqueous was washed with EtOAc (3×50 mL) and the organic layers were washed with saturated aqueous NaCl (50 mL). The organic layer was dried over $MgSO_4$, filtered and concentrated to afford N-[(5-chlorothien-2-yl)sulfonyl]-5,5,5-trifluoronorvaline as a dark red oil (1.1 g, 68.3%). Mass Spectrum $(-ESI)$: 350 $(M-H)$.

E. 5-Chloro-N-[4,4,4-trifluoro-1-(hydroxymethyl)butyl]thiophene-2-sulfonamide Borane-THF (1 M, 15 mL, 14.21 mmol) was added dropwise over 30 min at 0° C. to a solution of N-[(5-chlorothien-2-yl)sulfonyl]-5,5,5-trifluoronorvaline (1.0 g, 2.84 mmol) in THF (10 mL). The reaction was allowed to warm to 25° C. for 18 h and then was quenched by addition of 50 mL of 10% acetic acid in methanol. After solvent evaporation, the crude product was dissolved in EtOAc and washed with 1N HCl, $H_2O$ and saturated $NaHCO_3$. The organic layer was dried over $MgSO_4$, filtered and concentrated to produce a crude oil (0.83 g) that was purified via flash chromatography, eluent: 1:6 ethyl acetate-hexane. This produced the title compound 5-chloro-N-[4,4,4-trifluoro-1-(hydroxymethyl)butyl]thiophene-2-sulfonamide as a colorless oil (0.46 g, 48%). Mass Spectrum $(-ESI)$: 337 $(M-H)^-$.

Anal: Calc'd for $C_{11}H_{15}NClF_3O_3S_2$+0.30 $C_4H_8O_2$ C, 33.64; H, 3.71; N, 3.85.

Found: C, 34.01; H, 3.65; N, 3.67.

Examples 8 and 9

5-Chloro-N-{(1S,2R)-4,4,4-trifluoro-1-[(1S)-1-hydroxyethyl]-2-methylbutyl}thiophene-2-sulfonamide and

5-Chloro-N-{(1S,2R)-4,4,4-trifluoro-1-[(1R)-1-hydroxyethyl]-2-methylbutyl}thiophene-2-sulfonamide To 5-chloro-N-[(1S,2R)-4,4,4-trifluoro-1-(hydroxymethyl)-2-methylbutyl]thiophene-2-sulfonamide (prepared as in Example 1, 290 mg, 0.824 mmol) in $CH_2Cl_2$ (15 mL) at 0° C. was added Dess-Martin periodinane (410 mg, 0.989 mmol). The reaction mixture was warmed to 25° C. After 10 min, TLC (3:7 EtOAc-hex,) indicated presence of starting material. Additional Dess Martin periodinane (410 mg, 0.989 mmol) was added and after 15 min TLC indicated consumption of starting material. Diethyl ether (30 mL) was added, followed by aqueous 1 N $Na_2S_2O_3$ (25 mL) and saturated aqueous $NaHCO_3$ (25 mL). The milky white solution was stirred vigorously until both phases were homogenous. The layers were separated and the aqueous phase was extracted with diethyl ether. The combined organic extracts were dried ($Na_2SO_4$) and concentrated. Flash chromatography (eluent: 3:7 EtOAc-hexane) provided 5-chloro-N-[(1S,2R)-4,4,4-trifluoro-1-(formyl-2-methylbutyl)]thiophene-2-sulfonamide (100 mg, 35%) as a white solid.

To 5-chloro-N-[(1S,2R)-4,4,4-trifluoro-1-(formyl-2-methylbutyl)]thiophene-2-sulfonamide (100 mg, 0.286 mmol) in THF (3 mL) at 0° C. was added a solution of methylmagnesium bromide (0.61 mL, 1.4 M in THF/toluene, 0.86 mmol) dropwise. The reaction mixture was warmed to 25° C. and stirred for 3 h. It was then quenched with saturated aqueous ammonium chloride, extracted with EtOAc (2×40 mL), dried ($Na_2SO_4$) and concentrated. Flash chromatography (eluent: 3:7 EtOAc-hexane) provided 5-chloro-N-{(1S,2R)-4,4,4-trifluoro-1-[1-hydroxyethyl]-2-methylbutyl}thiophene-2-sulfonamide (75 mg, 74%) as a 3:1 mixture of diastereomers. Diastereomers were separated by HPLC (the Zorbax® silica gel column, 25×5 cm, eluent: 3:2 Methyl tertiary butyl ether (MTBE)-hexane, diastereomer 1 elutes at 11.4 min, diastereomer 2 elutes at 14.1 min).

Diastereomer 1: Mass Spectrum (−ESI): 364 (M−H)⁻.
Diastereomer 2: Mass Spectrum (−ESI): 364 (M−H)⁻.

Example 10

5-Chloro-N-[(1S,2S)-4,4,4-trifluoro-1-(hydroxymethyl)-2-methylbutyl]thiophene-2-sulfonamide A. 5,5,5-Trifluoro-L-isoleucine hydrochloride To (S)-(−)-α-methylbenzylamine hydrochloride salt (0.340 g, 2.16 mmol) in 20 mL of 1:1 MeOH/$H_2O$ was added potassium cyanide (0.139 g, 2.13 mmol) and (2S)-4,4,4-trifluoro-2-methylbutanal (0.300 g, 2.14 mmol, prepared by the procedure reported in Example 1, method 2 but using (S)-(−)-4-benzyl-2-oxazolidinone as the chiral auxiliary) and the reaction mixture was stirred for 17 h. Methanol was removed in vacuo and the product was extracted with EtOAc. The organic extract washed with aqueous 0.1 N HCl, dried ($Na_2SO_4$) and concentrated. Flash chromatography (eluent: 1:9 EtOAc-hexane) provided the α-amino nitrile (0.224 g, 39%) as a yellow oil. $^1$H-NMR indicated that the product is a 3:1 mixture of diastereomers.

Sulfuric acid (3 mL) was added to the mixture of diastereomers (0.224 g, 0.829 mmol) and the solution was stirred for 22 h. Then the reaction mixture was poured over crushed ice (~10 g). Concentrated aqueous ammonium hydroxide was added to neutralize the acid. This mixture was extracted with EtOAc, dried ($Na_2SO_4$), filtered and concentrated to give the resulting amide (0.224 g, 94%), which was used in the next step without purification.

A mixture of the amide (0.224 g, 0.777 mmol) and 5% palladium/C (Pd/C—40 mg) was shaken for 2 days in a Parr apparatus under 3 atm of hydrogen ($H_2$). The mixture was filtered through a plug of the Celite® reagent and the solvent was removed in vacuo to give the resulting amine as a white solid (128 mg, 90%), which was used in the next reaction without further purification.

The amine (128 mg, 0.695 mmol), in concentrated hydrochloric acid (3 mL), was heated to reflux for 24 h. The reaction mixture was cooled to room temperature and concentrated to give a mixture of amino acid hydrochloride salt (3:1 diastereomeric ratio) and 1 equivalent of ammonium chloride as a white solid (183 mg, 95%). Mass Spectrum (+ESI): 186 (M+H)⁺.

B. (2S,3S)-2-Amino-5,5,5-trifluoro-3-methylpentan-1-ol

To a solution of lithium borohydride (1.0 mL, 2.0 N in THF, 2.0 mmol) in THF (5 mL) at 0° C. was added chlorotrimethylsilane (0.51 mL, 4.01 mmol). The reaction mixture was warmed to 25° C. and, after 30 min, added dropwise to a 0° C. suspension of crude amino acid hydrochloride salt (184 mg, 0.669 mmol) in THF (5 mL). The mixture was warmed to 25° C., and after 21 h, quenched with MeOH. The volatiles were removed in vacuo and the resulting residue was dissolved in aqueous 1 N NaOH, extracted with $CHCl_3$ (4×20 mL), dried ($Na_2SO_4$) and concentrated to give the amino alcohol as a yellow oil (92 mg, 81%) which, according to its $^1$H NMR spectra, is a 3:1 mixture of diastereomers. Mass Spectrum (+ESI): 172 (M+H)⁺.

C. 5-Chloro-N-[(1S,2S)-4,4,4-trifluoro-1-(hydroxymethyl)-2-methylbutyl]thiophene-2-sulfonamide To the amino alcohol (168 mg, 0.981 mmol) in $CH_2Cl_2$ (10 mL) was added triethylamine (170 µL, 1.20 mmol) and 5-chlorothiophene-2-sulfonyl chloride (256 mg, 1.18 mmol). The reaction mixture was stirred at 25° C. for 21 h. The solution was diluted with EtOAc (50 mL), washed with 0.1 N HCl twice, dried and concentrated. Careful removal of impurities and the minor diastereomer by flash chromatography (eluent: 3:7 EtOAc-hexane) provided 5-chloro-N-[(1S,2S)-4,4,4-trifluoro-1-(hydroxymethyl)-2-methylbutyl]thiophene-2-sulfonamide (97 mg, 28%) as a white solid, mp 99-100° C. HPLC (Zorbax® silica gel column, eluent: 3:2 MTBE-hexane) indicated a 97:3 mixture of diastereomers. Chiral HPLC (AD column, eluent: 1:9 isopropanol-hexane) indicated >99% enantiomeric purity. $[\alpha]_D^{25}$=+8.95° (c=1% SOLUTION, MeOH). Mass Spectrum (−ESI): 350 (M−H)⁻.

Anal: Calc'd for $C_{10}H_{13}ClF_3NO_3S_2$ C, 34.14; H, 3.72; N, 3.98.

Found: C, 34.43; H, 3.70; N, 3.91.

Example 11

(2S,3S)-2-(5-Chloro-3-methylbenzo[b]thiophene-2-sulfonyl)-amido-5,5,5-trifluoro-3-ethyl-pentan-1-ol A. (R)-4-Benzyl-3-(2-R-bromo-3-S-ethyl-5,5,5-trifluoro-pentanoyl)-oxazolidin-2-one To copper (I) bromide-dimethyl sulfide complex (328 mg, 1.56 mmol) in THF/DMS (2:1, 60 mL), cooled to −40° C., was added ethyl magnesium bromide (1.06 mL, 3 M solution in THF, 3.2 mmol). The solution was allowed to stir for 10 min while warming to −15° C. The mixture was re-cooled to −40° C. and (R)-4-benzyl-3-(5,5,5-trifluoro-pent-2-enoyl)-oxazolidin-2-one (prepared as in Example 6 part C, 416 mg, 1.3 mmol) in THF (15 mL) was added. The solution was stirred at 25° C. for 16 h. The solution was re-cooled to −78° C. and N-bromosuccinimide (473 mg, 2.6 mmol) in THF (10 mL) was added. The solution was allowed to warm to 0° C. and shaken at 0° C. for 3 h. The reaction was quenched with a 1:1 solution of saturated ammonium carbonate and 0.5 N potassium bisulfate (15 mL). The organic phase was decanted off and concentrated to give (R)-4-benzyl-3-(2-R-bromo-3-S-ethyl-5,5,5-trifluoro-pentanoyl)-oxazolidin-2-one, identified by liquid chromatography mass spectrometry (LCMS).

B. 3-(2-S-Azido-3-S-ethyl-5,5,5-trifluoro-pentanoyl)-4R-benzyl-oxazolidin-2-one

To (R)-4-benzyl-3-(2R-bromo-3S-ethyl-5,5,5-trifluoro-pentanoyl)-oxazolidin-2-one dissolved in dimethylformamide (DMF—10 mL) was added sodium azide (172 mg, 2.6 mmol). The solution was stirred for 72 h, diluted with water (20 mL), extracted into ethyl acetate (2×20 mL) and concentrated to give 3-(2-S-azido-3-S-ethyl-5,5,5-trifluoro-pentanoyl)-4R-benzyl-oxazolidin-2-one, identified by LCMS.

C. (2S,3S)-2-Azido-3-ethyl-5,5,5-trifluoro-pentanoic acid 3-(2-S-Azido-3-S-ethyl-5,5,5-trifluoro-pentanoyl)-4-benzyl-oxazolidin-2-one was dissolved in a 2:1 mixture of THF and water (20 mL) at 0° C. and lithium hydroxide monohydrate (1.4 mmol, 60 mg) was added. The solution was shaken for 1 h at 0° C. and then saturated sodium carbonate (20 mL) was added. The mixture was extracted with ethyl acetate (20 mL). The aqueous phase was acidified with 2N hydrochloric acid and extracted with ethyl acetate (20 mL) to give (2S,3S)-2-azido-3-ethyl-5,5,5-trifluoro-pentanoic acid, identified by LCMS.

D. (2S,3S)-2-Amino-3-ethyl-5,5,5-trifluoro-pentan-1-ol (2S,3S)-2-Azido-3-ethyl-5,5,5-trifluoro-pentanoic acid was dissolved in THF (5 mL) at 0° C. and lithium aluminum hydride (1 M solution in THF) (1 mL, 1 mmol) was added. The resulting solution was stirred at 40° C. for 2 h. The reaction was quenched by sequential addition of water (60 μL), 15% aqueous sodium hydroxide (60 μL), and water (150 μL) with vigorous stirring between each addition. The mixture was then filtered and concentrated to give (2S,3S)-2-amino-3-ethyl-5,5,5-trifluoro-pentan-1-ol.

E. (2S,3S)-2-(5-Chloro-3-methylbenzo[b]thiophene-2-sulfonyl)-amido-5,5,5-trifluoro-3-ethyl-pentan-1-ol To the solution of (2S,3S)-2-amino-3-ethyl-5,5,5-trifluoro-pentan-1-ol (0.1 mmol) in THF (2 mL) was added triethylamine (83.7 μL, 0.6 mmol) and 5-chloro-3-methyl-benzo[b]thiophene-2-sulfonyl chloride (28 mg, 0.1 mmol). The solution was stirred for 16 h and then concentrated. The solvent was removed and the residue was dissolved in MeOH (1.5 mL) and purified by semi-preparative reverse phase (RP)-HPLC using the conditions below.
Semi-preparative RP-HPLC conditions:
Column: the Phenomenex® C18 Luna® 21.6 mm×60 mm, 5 μM
Solvent A: Water (0.02% TFA buffer)
Solvent B: Acetonitrile (0.02% TFA buffer)
Solvent Gradient: Time 0: 10% B; 2.5 min: 10% B; 14 min: 90% B.
Flow Rate: 22.5 mL/min
The product peak was collected based on UV absorption and concentrated to give the title compound, 1.7 mg, HPLC retention time 2.97 min, observed ion 428 (M−H).

Example 12

(2S,3R)-2-(5-Chloro-1,3-dimethyl-1H-pyrazole-4-sulfonyl)-amido-5,5,5-trifluoro-3-phenyl-pentan-1-ol Following essentially the same procedure as Example 11 but using phenyl magnesium bromide and 5-chloro-1,3-dimethylpyrazole-4-sulfonyl chloride, (2S,3R)-2-(5-chloro-1,3-dimethyl-1H-pyrazole-4-sulfonyl)-amido-5,5,5-trifluoro-3-phenyl-pentan-1-ol was prepared, 7.1 mg, HPLC retention time 2.25 min, observed ion 424 (M−H).

Example 13

Synthesis of Trifluoromethyl-Containing Heterocyclic Sulfonamide

In one embodiment, the method outlined in Scheme 13 is performed using the following exemplary reagents and conditions. However, one of skill in the art will readily understand that certain reaction conditions, e.g., times, temperatures, catalysts, and certain reagents may be modified.

With reference to Scheme 13, the aminoester XLVIII (250 g, 0.64 mol) was suspended in toluene (4 L) and neutralized to pH 7-8 with 0.4 N NaOH (1.6 L). The layers were separated and the organic phase washed with water (1.6 L) followed by drying with $Na_2SO_4$ (250 g). The toluene solution was cooled to −68° C. to −62° C. and treated with 25% diisobutylaluminum hydride (DIBAL-H) in toluene (1278 mL, 1.9 mol, 3 eq.), keeping the temperature below −60° C. The mixture was warmed to room temperature and stirred for 1 hour. The reaction was quenched with 10% aqueous NaOH (128 mL) followed by sodium citrate dihydrate (500 g) and anhydrous sodium sulfate (385 g). After stirring for 1 hour, the solids were removed via filtration and the solution concentrated to an oil. This was dissolved in diethyl ether (2.6 L), cooled to 5° C. and treated with 1N HCl in ether (750 mL). After stirring for 30 minutes, the solids were collected via filtration, washed with ether and dried under vacuum to give 189 g (85%) of a benzyl amine as a white solid. The benzyl amine (150 g, 0.43 mol) in methanol (150 mL) was hydrogenated at 40 psi in the presence of 40 g of 10% Pd/C catalyst. After 1.5 hours, the catalyst was removed via filtration and the solution concentrated to a solid. The solid was triturated with ether/hexane, collected via filtration and dried to give 94.8 g (90%) of an aminoalcohol as a solid.

The aminoalcohol (100.2 g, 0.41 mol) in $CH_2Cl_2$ (1150 mL) was treated with N,O-Bis(trimethylsilyl)acetamide (BSA—110 mL, 0.45 mol) followed by triethylamine (152.4 mL, 1.09 mol) and dimethylaminopyridine (DMAP—13 g). After 15 minutes, a solution of sulfonylchloride (105.5 g, 0.49 mol) in $CH_2Cl_2$ (186 mL) was added and the mixture was allowed to stir at room temperature for 19 hours (overnight). THF (450 mL) and 5% aq. HCl (800 mL) were added and the mixture stirred for 1 hour. The layers were separated and the organic layer washed with 5% $NaHCO_3$ followed by water. The solution was concentrated to give an oil and passed through a silica gel plug eluting with 30% EtOAc/hexanes. The fractions containing product were concentrated under vacuo, which promoted crystallization. Hexane was added and the solids collected via filtration to give 87.1 g (55%) of the target compound as a white solid. Concentration of the mother liquors gave a second crop of target compound, 12.6 g in 8% yield.

Example 14

5-Chloro-N-[1-(4,4-difluorocyclohexyl)-2-hydroxyethyl]thiophene-2-sulfonamide

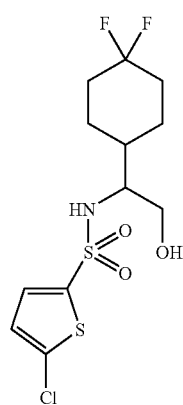

A. {[(5-Chlorothien-2-yl)sulfonyl]amino}(4,4-difluorocyclohexyl)acetic acid

The amino(4,4-difluorocyclohexyl)acetic acid (2.68 g, 10.973 mmol) was dissolved in 2N NaOH (20 mL). The solution was cooled to 0° C., 5-chlorothiophene-2-sulfonyl chloride (3.25 g, 12.42 mmol) was added (5 min) dropwise as a solution in THF (10 mL). The solution was allowed to warm up to 25° C. overnight. After 19 h, THF was removed in vacuo and the mixture was acidified to a pH of about 1 to about 2 with 2N HCl (20 mL). The aqueous layer washed with EtOAc (4×50 mL). The combined organic layers were dried over $MgSO_4$, filtered, and concentrated to produce {[(5-chlorothien-2-yl)sulfonyl]amino}(4,4-difluorocyclohexyl)acetic acid as a crude oil (3.8 g, 98.2%). Mass Spectrum (−ESI): 372 (M−H)⁻.

B. 5-Chloro-N-[1-(4,4-difluorocyclohexyl)-2-hydroxyethyl]thiophene-2-sulfonamide To a slurry of LAH (0.406 g, 10.70 mmol) in THF (20 mL) was added {[(5-chlorothien-2-yl)sulfonyl]amino}(4,4-difluorocyclohexyl)acetic acid (2.0 g, 5.35 mmol) dropwise at 0° C. over 20 min.

The reaction was heated to 70° C. for 18 h. The reaction slurry (light brown) was cooled to 0° C. and the reaction was quenched with $H_2O$ (1.5 mL), 1N NaOH (4.5 mL) and $H_2O$ (1.5 mL). The reaction was stirred for 4 h to obtain a white slurry. The slurry was filtered and the mother liquor was further dried over $MgSO_4$, filtered, and concentrated in vacuo to obtain a crude yellow oil (1.68 g). The crude product was purified by Biotage Flash™ 40 chromatography, eluent: 1:2 EtOAc-hexanes, to afford 5-chloro-N-[1-(4,4-difluorocyclohexyl)-2-hydroxyethyl]thiophene-2-sulfonamide as a white amorphous solid (0.15 g, 7.8%). Mass Spectrum (−ESI): 358 (M−H)⁻.

Anal: Calc'd for $C_{12}H_{16}ClNF_2O_3S_2 \cdot 0.17$ EtOAc C, 41.02; H, 4.49; N, 3.76.

Found: C, 40.63; H, 4.67; N, 3.74.

Example 15

5-Chloro-N-[1-(6,6-difluorobicyclo[3.1.0]hex-3-yl)-2-hydroxyethyl]thiophene-2-sulfonamide

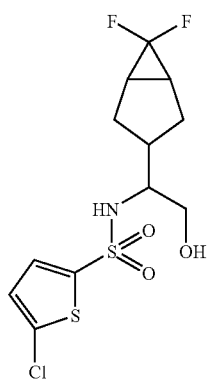

A. Methyl amino(6,6-difluorobicyclo[3.1.0]hex-3-yl)acetate

To a solution of amino(6,6-difluorobicyclo[3.1.0]hex-3-yl)acetic acid (1.0 g, 5.23 mmol) in $CH_2Cl_2$:MeOH (4:1) was added dropwise $TMSCHN_2$ (10.5 mL) over 10 min at 0° C. until a neon yellow color persisted. The reaction mixture was allowed to warm to 25° C. over 19 h. The solvent was removed in vacuo to obtain methyl amino(6,6-difluorobicyclo[3.1.0]hex-3-yl)acetate as a light yellow oil (0.9 g, 84.11%). Mass Spectrum (−ESI): 206 (M+H)⁺.

B. Methyl {[(5-chlorothien-2-yl)sulfonyl]amino}(6,6-difluorobicyclo[3.1.0]hex-3-yl)acetate 5-Chlorothiophene-2-sulfonyl chloride (1.26 g, 4.82 mmol) was added dropwise (5 min) as a solution in $CH_2Cl_2$ (10 mL) to a 0° C. solution of methyl amino(6,6-difluorobicyclo[3.1.0]hex-3-yl)acetate (0.9 g, 4.38 mmol) in $CH_2Cl_2$ (10 mL) and triethylamine (1.22 mL, 8.77 mmol). The solution was allowed to warm to 25° C. overnight (19 h). An aliquot was taken and TLC (1:4 EtOAc-hexane) indicated that the reaction was complete. It was diluted in $CH_2Cl_2$ (100 mL) and the organic layer was washed with 1N HCl (20 mL) and saturated aqueous NaCl (20 mL). The organic layer was dried over $MgSO_4$, filtered, and concentrated to obtain a crude off-yellow solid (1.69 g). The crude product was purified by the Biotage Flash™ 40 chromatography instrument, eluent: 1:4 EtOAc-hexanes, to afford methyl {[(5-chlorothien-2-yl)sulfonyl]amino}(6,6-difluorobicyclo[3.1.0]hex-3-yl)acetate as a colorless oil (0.230 g, 12.23%). Mass Spectrum (−ESI): 384 (M+H)⁺.

C. 5-Chloro-N-[1-(6,6-difluorobicyclo[3.1.0]hex-3-yl)-2-hydroxyethyl]thiophene-2-sulfonamide To a slurry of LAH (0.030 g, 0.78 mmol) in THF (5 mL) was added methyl {[(5-chlorothien-2-yl)sulfonyl]amino}(6,6-difluorobicyclo[3.1.0]hex-3-yl)acetate (0.154 g, 0.38 mmol) dropwise at 0° C. over 20 min. The slurry (gray) was allowed to warm to 25° C. over 19 h. The reaction slurry was cooled to 0° C. and the reaction was quenched with $H_2O$ (0.5 mL), 1N NaOH (1.5 mL) and $H_2O$ (0.5 mL). The reaction was stirred 4 h to obtain a white slurry. The slurry was filtered and the mother liquor was further dried over $MgSO_4$, filtered, and concentrated in vacuo to obtain a crude yellow oil (0.162 g). The crude product was purified by the Biotage Flash™ 40 chromatography system, eluent: 1:4 EtOAc-hexanes, to afford 5-chloro-N-[1-(6,6-difluorobicyclo[3.1.0]hex-3-yl)-2-hydroxyethyl]thiophene-2-sulfonamide as a colorless oil (0.105 g, 77.77%). Mass Spectrum (−ESI): 356 (M−H)⁻.

Anal: Calc'd for $C_{13}H_{14}ClNF_2O_4S_2 \cdot 0.20$ EtOAc C, 41.41; H, 3.84; N, 3.56.

Found: C, 41.08; H, 3.90; N, 3.47.

Example 16

5-Chloro-N-[(1S,2R)-4,4,4-trifluoro-1-formyl-2-methylbutyl]thiophene-2-sulfonamide

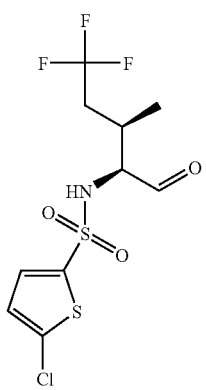

A solution of 5-chloro-N-[(1S,2R)-4,4,4-trifluoro-1-hydroxymethyl)-2-methylbutyl]thiophene-2-sulfonamide (prepared as in Example 1, 3.0 g, 8.53 mmol) in $CH_2Cl_2$ saturated with water (30 mL) was stirred under nitrogen at 0° C. Dess-Martin periodinane reagent (7.59 g, 17.90 mmol) was added in one portion. The resulting suspension was stirred at 25° C., monitoring the progress of reaction by TLC analysis (1:2 EtOAc/hexane). As the rate of conversion of the starting material slowed, additional 2 mL portions of $CH_2Cl_2$ saturated with water were added (three portions over 15 min). After 19 h at 25° C., the reaction was complete by TLC. The solution was diluted with $Et_2O$ (50 mL) and a solution of sodium thiosulfate, $Na_2S_2O_3$ (93.83 mmol, 14.8 g, 11 eq) in 80% saturated aqueous sodium bicarbonate solution (50 mL) was added. The mixture was stirred rapidly for 10 min until both phases were clear. The layers were separated and the aqueous phase was extracted with ether (30 mL). The combined organic layers were washed sequentially with saturated aqueous sodium bicarbonate (10 mL) and brine (15 mL), then dried over $MgSO_4$, filtered and concentrated to obtain a crude oil (2.67 g). The crude product was purified by the Biotage Flash™ 60 chromatography system, eluent: 1:6 EtOAc-hexanes, to afford 5-chloro-N-[(1S,2R)-4,4,4-trifluoro-1-formyl-2-methylbutyl]thiophene-2-sulfonamide as a colorless oil (2.65 g, 88.93%). Mass Spectrum (+ESI): 350 $(M+H)^+$.

Anal: Calc'd for $C_{10}H_{11}ClNF_3O_3S_2 \cdot 0.35 H_2O$ C, 33.34; H, 2.83; N, 3.87.

Found: C, 33.74; H, 3.31; N, 3.93.

Example 17

N-[(1S,2R)-1-Acetyl-4,4,4-trifluoro-2-methylbutyl]-5-chlorothiophene-2-sulfonamide

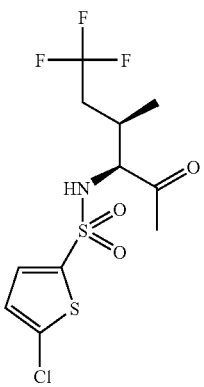

A. 5-Chloro-N-[(1S,2R)-4,4,4-trifluoro-1-(1-hydroxyethyl)-2-methylbutyl]thiophene-2-sulfonamide A solution of 5-chloro-N-[(1S,2R)-4,4,4-trifluoro-1-formyl-2-methylbutyl]thiophene-2-sulfonamide (prepared as in Example 16, 1.0 g, 2.86 mmol) in THF (10 mL) was stirred under nitrogen at 0° C. Methyl magnesium bromide (3.0 M in ethyl ether, 1.9 mL, 5.71 mmol.) was added dropwise and the resulting solution was stirred for 1 h at 25° C. After this time period, the reaction was complete by TLC (1:2 EtOAc/hexane). The solution was quenched with saturated aqueous $NH_4Cl$ (10 mL) and extracted with ether (40 mL). The organic layer washed with brine (20 mL) and then dried over $MgSO_4$ to obtain a crude oil (0.867 g). The crude product was purified by the Biotage Flash™ 60 chromatography system, eluent: 1:6 EtOAc-hexanes, to afford 5-chloro-N-[(1S,2R)-4,4,4-trifluoro-1-(1-hydroxyethyl)-2-methyl butyl]thiophene-2-sulfonamide as a colorless oil (0.495 g, 49.5%). Mass Spectrum (−ESI): 364 $(M-H)^-$.

B. N-[(1S,2R)-1-acetyl-4,4,4-trifluoro-2-methylbutyl]-5-chlorothiophene-2-sulfonamide A solution of 5-chloro-N-[(1S,2R)-4,4,4-trifluoro-1-(1-hydroxyethyl)-2-methylbutyl]thiophene-2-sulfonamide (0.390 g, 1.06 mmol) in $CH_2Cl_2$ saturated with water (30 mL) was stirred under nitrogen at 0° C. Dess-Martin periodinane reagent (0.95 g, 2.23 mmol) was added in one portion. The resulting suspension was stirred at 25° C., monitoring the progress of reaction by TLC analysis (1:2 EtOAc/hexane). As the rate of conversion of the starting material slowed, additional 1 mL portions of $CH_2Cl_2$ saturated with water were added (three portions over 15 min). After 19 h at 25° C., the reaction was complete by TLC. The solution was diluted with $Et_2O$ (50 mL) and a solution of sodium thiosulfate, $Na_2S_2O_3$ (11.83 mmol, 4.8 g, 11 eq) in 80% saturated aqueous sodium bicarbonate solution (40 mL) was added. The mixture was stirred rapidly for 10 min until both phases were clear. The layers were separated and the aqueous phase was extracted with ether (20 mL). The combined organic layers were washed sequentially with saturated aqueous sodium bicarbonate (10 mL) and brine (15 mL), then dried over $MgSO_4$, filtered and concentrated to obtain a crude oil (0.38 g). The crude product was purified by the Biotage Flash™ 40 chromatography system, eluent: 1:6 EtOAc-hexanes, to afford N-[(1S,2R)-1-acetyl-4,4,4-trifluoro-2-methylbutyl]-5-chlorothiophene-2-sulfonamide as a white solid (0.265 g, 73.10%). Mass Spectrum (−ESI): 362 (M−H)⁻.

Anal: Calc'd for $C_{11}H_{13}ClNF_3O_3S_2$ C, 36.32; H, 3.6; N, 3.85.

Found: C, 36.08; H, 3.2; N, 3.74.

Example 18

5-Chloro-N-[(1S,2R)-4,4,4-trifluoro-1-(1-hydroxy-1-methylethyl)2-methylbutyl]thiophene-2-sulfonamide

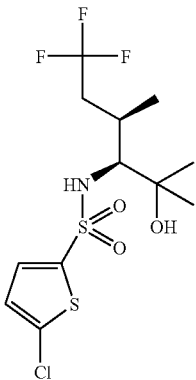

A solution of N-[(1S,2R)-1-acetyl-4,4,4-trifluoro-2-methylbutyl]-5-chlorothiophene-2-sulfonamide (prepared as in Example 17, 0.100 g, 0.275 mmol) in THF (5 mL) was stirred under nitrogen at 0° C. Methyl magnesium bromide (3.0 M in ethyl ether, 0.266 mL, 0.824 mmol,) was added dropwise and the resulting solution was stirred for 19 h at 25° C. After this time period, the reaction was complete by TLC (1:2 EtOAc/hexane). The solution was quenched with saturated aqueous $NH_4Cl$ (10 mL) and extracted with ether (40 mL). The organic layer washed with brine (20 mL) and then dried over $MgSO_4$ to obtain a crude oil (0.110 g). The crude product was purified by the Biotage Flash™ 40 chromatography system, eluent: 1:4 EtOAc-hexanes, to afford 5-chloro-N-[(1S,2R)-4,4,4-trifluoro-1-(1-hydroxy-1-methylethyl)-2-methylbutyl]thiophene-2-sulfonamide as a white solid (0.049 g, 46.6%). Mass Spectrum (−ESI): 378 (M−H)⁻.

Anal: Calc'd for $C_{12}H_{17}ClNF_3O_3S_2$ C, 37.94; H, 4.51; N, 3.69.

Found: C, 37.45; H, 4.03; N, 3.68.

Example 19

4-Bromo-5-chloro-N-[3,3,3-trifluoro-1-(hydroxymethyl)-2-(trifluoromethyl)propyl]thiophene-2-sulfonamide

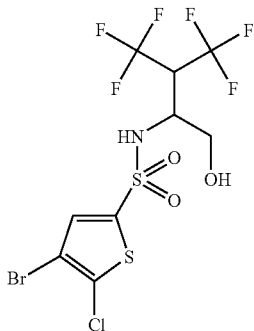

A. Methyl 4,4,4,4',4',4'-hexafluoro-dl-valinate

A solution of 4,4,4,4',4',4'-hexafluoro-dl-valine (1.1 g, 4.88 mmol) in $CH_2Cl_2$-MeOH (4:1, 25 mL) was stirred under nitrogen at 0° C. TMS-diazomethane (2.0 M in hexane, 20 mL, 19.55 mL) was added dropwise and the resulting neon greenish solution stirred for 19 h at 25° C. After this time period, the reaction was complete by TLC (10% MeOH in chloroform). After concentration, the resulting residue of methyl 4,4,4,4',4',4'-hexafluoro-dl-valinate (1.1 g) was used directly in the next step without further purification. Mass Spectrum (−ESI): 238 (M−H)⁻.

B. Methyl N-[(4-bromo-5-chlorothien-2-yl)sulfonyl]-4,4,4,4',4',4'-hexafluoro-dl-valinate A solution of methyl 4,4,4,4',4',4'-hexafluorovalinate (1.0 g, 4.18 mmol) in $CH_2Cl_2$ (10 mL) was stirred under $N_2$ atmosphere at 25° C. Pyridine (0.81 mL, 10.04 mmol) was added dropwise followed by 4-bromo-5-chlorothiophene-2-sulfonyl chloride (1.486 g, 5.05 mmol) in one portion and the resulting solution stirred for 19 h at 25° C. After this time period, the reaction was complete by TLC (1:4 EtOAc-hexane). After quenching with water (1.0 mL), the mixture was diluted with $CH_2Cl_2$ (30 mL). The organic layer washed sequentially with 1N aqueous HCl (10 mL), saturated aqueous $NaHCO_3$ (10 mL) and brine (15 mL), then dried over $MgSO_4$, filtered and concentrated to obtain a crude oil (2.1 μg). The crude product was purified by the Biotage Flash™ 40 chromatography system, eluent: 1:6 EtOAc-hexanes, to afford methyl N-[(4-bromo-5-chloro-thien-2-yl)sulfonyl]-4,4,4,4',4',4'-hexafluoro-dl-valinate as a white solid (1.62 g, 83.07%). Mass Spectrum (−ESI): 497 (M−H)⁻.

C. 4-Bromo-5-chloro-N-[3,3,3-trifluoro-1-(hydroxymethyl)-2-(trifluoromethyl)propyl]thiophene-2-sulfonamide To a solution of methyl N-[(4-bromo-5-chloro thien-2-yl)sulfonyl]-4,4,4,4',4',4'-hexafluorovalinate (1.45 g, 2.907 mmol) in THF (20 mL) was added lithium borohydride ($LiBH_4$) (5.82 mL, 11.64 mmol) under $N_2$ atmosphere at 0° C. The reaction was allowed to warm to 25° C. for 19 h. The reaction was cooled to 0° C., quenched with 2N HCl (slow addition), diluted in ether (40 mL) and the organic layer washed sequentially with 1N aqueous HCl (10 mL), saturated aqueous $NaHCO_3$ (10 mL) and brine (15 mL), then dried over $MgSO_4$, filtered and concentrated to obtain a crude oil (1.3 g). The crude product was purified by the Biotage Flash™ 40 chromatography system, eluent: 1:6 EtOAc-hexanes, to afford 4-bromo-5-chloro-N-[3,3,3-trifluoro-1-(hydroxymethyl)-2-(trifluoromethyl)propyl]thiophene-2-sulfonamide as a white solid (1.13 g, 84.32%). Mass Spectrum (−ESI): 469 (M−H)⁻.

Anal: Calc'd for $C_9H_7ClBrNF_6O_3S_2$ C, 22.97; H, 1.50; N, 2.98.

Found: C, 23.11; H, 1.16; N, 2.78.

Example 20

4-Bromo-5-chloro-N-[(1S)-3,3,3-trifluoro-1-(hydroxymethyl)-2-(trifluoromethyl)propyl]thiophene-2-sulfonamide

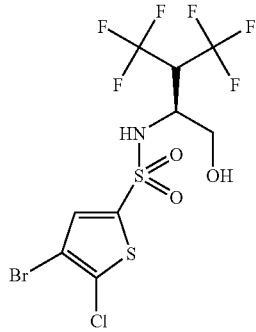

4-Bromo-5-chlorothiophene-2-sulfonyl chloride (0.193 g, 0.654 mmol) was added dropwise (5 min) as a solution in $CH_2Cl_2$ (1.0 mL) to a 0° C. solution of (2S)-2-amino-3,3,3-trifluoro-3-(trifluoromethyl)butan-1-ol (prepared according to the method of Example 13, 0.115 g, 0.548 mmol) in $CH_2Cl_2$ (10 mL) and pyridine (0.9 mL, 1.09 mmol). The solution was allowed to warm to 25° C. overnight (19 h). An aliquot was taken and TLC (1:1 EtOAc-hexane) indicated that reaction was complete. The reaction mixture was diluted with $CH_2Cl_2$ (100 mL) and the organic layer washed with 1N HCl (2×50 mL) and saturated aqueous NaCl (50 mL), dried over $MgSO_4$, filtered, and concentrated to obtain a crude off-white solid (0.270 g). The crude product was purified by the Biotage Flash™ 40 chromatography system, eluent: 1:6 EtOAc-hexanes, to afford 4-bromo-5-chloro-N-[(1S)-3,3,3-trifluoro-1-(hydroxymethyl)-2-(trifluoromethyl)propyl]thiophene-2-sulfonamide as a white solid (39 mg, 15.11%).

Mass Spectrum (–ESI): 469 (M–H)⁻.

Example 21

5-Chloro 4-fluoro-N-[3,3,3-trifluoro-1-(hydroxymethyl)-2-(trifluoromethyl)propyl]thiophene-2-sulfonamide

A. 5-Chloro-N-[3,3,3-trifluoro-1-(hydroxymethyl)-2-(trifluoromethyl)propyl]thiophene-4-(tributylstannyl)-2-sulfonamide Bis(tributyltin) (0.939 g, 2.87 mmol) and tetrakis(triphenyl phosphine)palladium (0) (0.221 g, 0.191 mmol) were added to a solution of 4-bromo-5-chloro-N-[3,3,3-trifluoro-1-(hydroxymethyl)-2-(trifluoromethyl)propyl]thiophene-2-sulfonamide (prepared as in Example 19, 0.9 g, 1.91 mmol) in 1,4-dioxane (42 mL). The brown solution was heated to reflux overnight (19 h). An aliquot was taken and TLC (1:1 EtOAc-hexane) indicated that reaction was complete. The slurry was then filtered and the solvent removed in vacuo to obtain a yellow-oil (1.31 g). The crude product was purified by the Biotage Flash™ 40 chromatography system, eluent: 1:6 EtOAc-hexanes, to afford 5-chloro-N-[3,3,3-trifluoro-1-(hydroxymethyl)-2-(trifluoromethyl)propyl]thiophene-4-(tributylstannyl)-2-sulfonamide as a white solid (0.220 g, 18.86%). Mass Spectrum (–ESI): 554 (M–H)⁻.

B. 5-Chloro-4-fluoro-N-[3,3,3-trifluoro-1-(hydroxymethyl)-2-(trifluoromethyl)propyl]thiophene-2-sulfonamide A solution of 5-chloro-N-[3,3,3-trifluoro-1-(hydroxymethyl)-2-(trifluoromethyl)propyl]thiophene-4-(tributylstannyl)-2-sulfonamide (0.220 g, 0.396 mmol) in dry acetonitrile (10 mL) was stirred under nitrogen at 25° C. The Selectfluor® reagent (0.147 g, 0.416 mmol) was added in one portion and the solution stirred for 19 h at 25° C. After 3 h, a white precipitate began to appear. After 19 h, an aliquot was taken and TLC (1:2 EtOAc-hexane) indicated that reaction was not complete. Mainly, starting material was present. The reaction was heated to 80° C. for 6 h. An aliquot was taken and TLC (1:2 EtOAc-hexane) indicated that reaction was complete. The slurry was then filtered and the solvent removed in vacuo to obtain a yellow oil (0.11 g). The crude product was purified by prep RP-HPLC (the Primesphere™ 2×25 cm column, eluent: 55% MeCN in 0.01% aqueous trifluoroacetic acid (TFA), flow rate=25 mL/min, Rt, 4.401 min) to obtain 5-chloro 4-fluoro-N-[3,3,3-trifluoro-1-(hydroxymethyl)-2-(trifluoromethyl)propyl]thiophene-2-sulfonamide as an amorphous white solid (0.004 g, 24.69%). Mass Spectrum (–ESI): 408 (M–H)⁻.

Example 22

5-Bromo-N-[3,3,3-trifluoro-1-(hydroxymethyl)-2-(trifluoromethyl)propyl]thiophene-2-sulfonamide

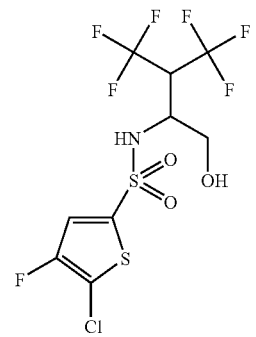

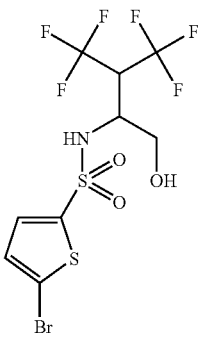

A. Ethyl N-[(5-bromothien-2-yl)sulfonyl]-4,4,4,4',4', 4'-hexafluoro-dl-valinate

A solution of ethyl 4,4,4,4',4',4'-hexafluoro-dl-valinate (1.64 g, 6.48 mmol), prepared as described (J. Med Chem. 1981, 24, 1043-1047), in CH$_2$Cl$_2$ (10 mL) was stirred under N$_2$ atmosphere at 25° C. Pyridine (0.81 mL, 10.04 mmol) was added dropwise followed by 5-bromothiophene-2-sulfonyl chloride (2.034 g, 7.77 mmol) in one portion and the resulting solution stirred for 19 h at 25° C. After this time period, the reaction was complete by TLC (1:4 EtOAc-hexane). After quenching with water (2.0 mL), the mixture was diluted with CH$_2$Cl$_2$ (40 mL). The organic layer washed sequentially with 1N aqueous HCl (20 mL), saturated aqueous NaHCO$_3$ (20 mL) and brine (15 mL), dried over MgSO$_4$, filtered, and concentrated to obtain a crude oil (3.3 g). The crude product was purified by the Biotage Flash™ 40 chromatography system, eluent: 1:6 EtOAc-hexanes, to afford ethyl N-[(5-bromothien-2-yl)sulfonyl]-4,4,4,4',4',4'-hexafluoro-dl-valinate as a white solid (2.40 g, 80.0%). Mass Spectrum (–ESI): 477 (M–H)$^-$.

B. 5-Bromo-N-[3,3,3-trifluoro-1-(hydroxymethyl)-2-(trifluoromethyl)propyl]thiophene-2-sulfonamide To a solution of ethyl N-[(5-bromo-thien-2-yl)sulfonyl]-4,4,4,4',4',4'-hexafluorovalinate (2.4 g, 5.02 mmol) in THF (20 mL) was added LiBH$_4$ (20 mL, 20.07 mmol) under N$_2$ atmosphere at 0° C. The reaction was allowed to warm to 25° C. for 19 h. The reaction was cooled to 0° C. and quenched with 2N HCl (slow addition), diluted in ether (50 mL) and the organic layer washed sequentially with 1N aqueous. HCl (10 mL), saturated aqueous NaHCO$_3$ (10 mL) and brine (15 mL), then dried over MgSO$_4$, filtered and concentrated to obtain a crude oil (2.31 g). The crude product was purified by the Biotage Flash™ 40 chromatography system, eluent: 1:6 EtOAc-hexanes, to afford 5-bromo-N-[3,3,3-trifluoro-1-(hydroxymethyl)-2-(trifluoromethyl)propyl]thiophene-2-sulfonamide as a white solid (1.3 g, 59.63%). Mass Spectrum (–ESI): 435 (M–H)$^-$.

Anal: Calc'd for C$_9$H$_8$BrNF$_6$O$_3$S$_2$ C, 24.78; H, 1.85; N, 3.21.

Found: C, 24.74; H, 1.32; N, 3.11.

Example 23

5-Fluoro-N-[3,3,3-trifluoro-1-(hydroxymethyl)-2-(trifluoromethyl)propyl]thiophene-2-sulfonamide

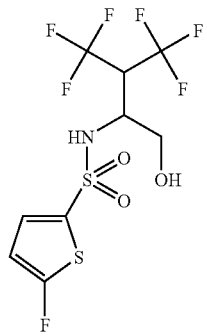

A. N-[3,3,3-Trifluoro-1-(hydroxymethyl)-2-(trifluoromethyl)propyl]thiophene-5-(tributylstannyl)-2-sulfonamide Bis(tributyltin) (1.36 g, 4.13 mmol) and tetrakis(triphenylphosphine)palladium (0) (0.32 g, 0.275 mmol) were added to a solution of 5-bromo-N-[3,3,3-trifluoro-1-(hydroxymethyl)-2-(trifluoromethyl)propyl]thiophene-2-sulfonamide (prepared as in Example 22, 1.2 g, 2.75 mmol) in 1,4-dioxane (40 mL). The brown solution was heated to reflux overnight (19 h). An aliquot was taken and TLC (1:2 EtOAc-hexane) indicated that reaction was complete. The slurry was then filtered and the solvent removed in vacuo to obtain a yellow-oil (1.4 g). The crude product was purified by the Biotage Flash™ 40 chromatography system, eluent: 1:6 EtOAc-hexanes, to afford N-[3,3,3-trifluoro-1-(hydroxymethyl)-2-(trifluoromethyl)propyl]thiophene-5-(tributylstannyl)-2-sulfonamide as a white solid (0.400 g, 27.97%). Mass Spectrum (–ESI): 520 (M–H)$^-$.

B. 5-Fluoro-N-[-3,3,3-trifluoro-1-(hydroxymethyl)-2-(trifluoromethyl)propyl]thiophene-2-sulfonamide A solution of N-[3,3,3-trifluoro-1-(hydroxymethyl)-2-(trifluoromethyl)propyl]thiophene-5-(tributyl stannyl)-2-sulfonamide (0.400 g, 0.76 mmol) in dry acetonitrile (10 mL) was stirred under nitrogen at 25° C. The Selectfluor® reagent (0.285 g, 0.806 mmol) was added in one portion and the solution stirred for 19 h at 25° C. After 3 h, a white precipitate began to appear. After 19 h, an aliquot was taken and TLC (1:2 EtOAc-hexane) indicated that reaction was not complete. Mainly, starting material was present. The reaction was heated to 80° C. for 6 h. An aliquot was taken and TLC (1:2 EtOAc-hexane) indicated that reaction was complete. The slurry was then filtered and the solvent removed in vacuo to obtain a yellow oil (0.191 g). The crude product was purified by the Biotage Flash™ 40 chromatography system, eluent: 1:6 EtOAc-hexanes, to obtain 5-fluoro-N-[3,3,3-trifluoro-1-(hydroxymethyl)-2-(trifluoromethyl)propyl]thiophene-2-sulfonamide as an amorphous white solid (0.010 g, 34.72%). Mass Spectrum (–ESI): 374 (M–H)$^-$.

Example 24

5-Bromo-N-[(1S)-3,3,3-trifluoro-1-(hydroxymethyl)-2-(trifluoromethyl)propyl]thiophene-2-sulfonamide

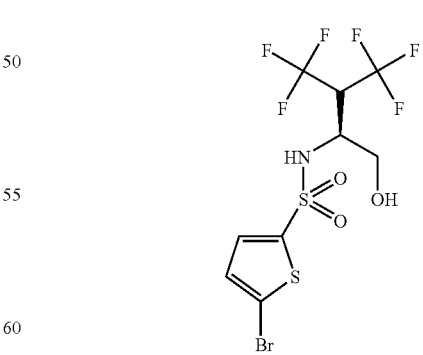

5-Bromothiophene-2-sulfonyl chloride (0.149 g, 0.568 mmol) was added dropwise (5 min) as a solution in CH$_2$Cl$_2$ (1.0 mL) to a 0° C. solution of (2S)-2-amino-4,4,4-trifluoro-3-(trifluoromethyl)butan-1-ol (0.100 g, 0.474 mmol) in CH$_2$Cl$_2$ (10 mL) and pyridine (0.1 mL, 0.95 mmol). The solution was allowed to warm to 25° C. overnight (19 h). An aliquot was taken and TLC (1:2 EtOAc-hexane) indicated that reaction was complete. It was diluted with CH₂Cl₂ (10 mL) and the organic layer washed with 1N HCl (2×10 mL), saturated aqueous NaCl (10 mL). The organic layer was dried over MgSO₄, filtered and concentrated to obtain a crude off white solid (0.120 g). The crude product was recrystallized from CH₂Cl₂:hexane (1:7) to afford 5-bromo-N-[(1S)-3,3,3-trifluoro-1-(hydroxymethyl)-2-(trifluoromethyl)propyl]thiophene-2-sulfonamide as a white fluffy solid (0.0541 g, 27.05%). Mass Spectrum (–ESI): 435 (M–H)⁻.

Example 25

5-Fluoro-N-[(1S)-3,3,3-trifluoro-1-(hydroxymethyl)-2-(trifluoromethyl)propyl]thiophene-2-sulfonamide

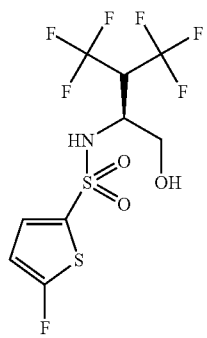

A. N-[(1S)-3,3,3-Trifluoro-1-(hydroxymethyl)-2-(trifluoromethyl)propyl]thiophene-5-(tributylstannyl)-2-sulfonamide Bis(tributyltin) (1.36 g, 4.13 mmol) and tetrakis(triphenyl phosphine)palladium (0) (0.32 g, 0.275 mmol) were added to a solution of 5-bromo-N-[(1S)-3,3,3-trifluoro-1-(hydroxymethyl)-2-(trifluoromethyl)propyl]thiophene-2-sulfonamide (prepared as in Example 24, 1.1 g, 2.52 mmol) in 1,4-dioxane (40 mL). The brown solution was heated to reflux overnight (19 h). An aliquot was taken and TLC (1:2 EtOAc-hexane) indicated that reaction was complete. The slurry was then filtered and the solvent removed in vacuo to obtain a yellow-oil (1.05 g). The crude product was purified by the Biotage Flash™ 40 chromatography system, eluent: 1:6 EtOAc-hexanes, to afford N-[(1S)-3,3,3-trifluoro-1-(hydroxymethyl)-2-(trifluoromethyl)propyl]thiophene-5-(tributylstannyl)-2-sulfonamide as a white solid (0.350 g, 26.7%). Mass Spectrum (–ESI): 520 (M–H)⁻.

B. 5-Fluoro-N-[(1S)-3,3,3-trifluoro-1-(hydroxymethyl)-2-(trifluoromethyl)propyl]thiophene-2-sulfonamide A solution of N-[(1S)-3,3,3-trifluoro-1-(hydroxymethyl)-2-(trifluoromethyl)propyl]thiophene-5-(tributyl stannyl)-2-sulfonamide (0.400 g, 0.76 mmol) in dry acetonitrile (10 mL) was stirred under nitrogen at 25° C. The Selectfluor® reagent (0.285 g, 0.806 mmol) was added in one portion and the solution stirred for 19 h at 25° C. After 3 h, a white precipitate began to appear. After 19 h, an aliquot was taken and TLC (1:2 EtOAc-hexane) indicated that reaction was not complete. Mainly, starting material was present. The reaction was heated to 80° C. for 6 h. An aliquot was taken and TLC (1:2 EtOAc-hexane) indicated that reaction was complete. The slurry was then filtered and the solvent removed in vacuo to obtain a yellow-oil (0.078 g). The crude product was purified by the Biotage Flash™ 40 chromatography system, eluent: 1:6 EtOAc-hexanes, to obtain 5-fluoro-N-[(1S)-3,3,3-trifluoro-1-(hydroxymethyl)-2-(trifluoromethyl)propyl]thiophene-2-sulfonamide as an amorphous white solid (0.0061 g, 2.8%). Mass Spectrum (–ESI): 374 (M–H)⁻.

Example 26

5-Chloro-N-[4,4,4-trifluoro-1-(hydroxymethyl)-2-(2,2,2-trifluoroethyl)butyl]thiophene-2-sulfonamide

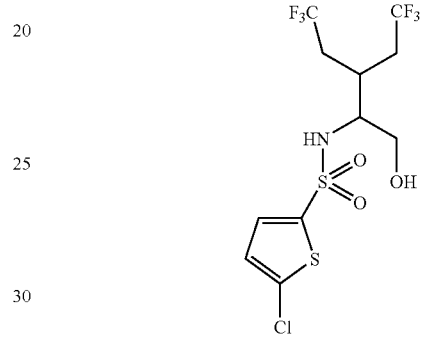

A. (3,3,3-Trifluoropropyl)-triphenylphosphonium iodide

To a solution of 1-iodo-3,3,3-trifluoropropane (19.3 g, 86.1 mmol) in toluene (50 mL) at 23° C. was added triphenylphosphine (25.8 g, 98.5 mmol). The reaction mixture was warmed to reflux and stirred for 28 h. The resulting mixture was cooled to 0° C. in an ice bath and filtered to collect the white solid product. The product washed with toluene (3×) and air-dried to afford the pure product as white solid (33.4 g, 80%).

B. 4,4,4-Trifluoro-2-(triphenyl-1⁵-phosphanylidene)-butyric acid ethyl ester

To a suspension of (3,3,3-trifluoropropyl)-triphenylphosphonium iodide (23.5 g, 48.4 mmol) in THF (100 mL) at –78° C. was added slowly a solution of potassium bis(trimethylsilyl)amide (0.5 M in toluene, 175 mL) through an addition funnel under nitrogen. The resulting mixture was stirred at –78° C. for 45 min followed by dropwise addition of ethylchloroformate (neat, 5.0 mL). The reaction mixture was then allowed to warm up to –20° C. over 3 h while stirring. The reaction was then quenched by pouring into brine (100 mL) and extracted with ethyl acetate (100 mL×2). The organic extract was dried (Na₂SO₄) and concentrated under reduced pressure. Flash chromatography with ethyl acetate-hexane (0-100%) through a silica gel column (120 g) afforded the product as light yellow solid. Recrystallization of this material with Et₂O afforded the pure product as white solid (6.7 g, 32%). Mass Spectrum (+ESI): 431 [M+H]⁺

C. 4,4,4-Trifluoro-2-(2,2,2-trifluoroethyl)-but-2-enoic acid ethyl ester

To a solution of 4,4,4-trifluoro-2-(triphenyl-$\lambda^5$-phosphanylidene)-butyric acid ethyl ester (2.0 g, 4.65 mmol) in THF (5 mL) was added 1 mL of trifluoroacetaldehyde hydrate (tech.). The mixture was sealed in a pressure tube and heated at 100° C. for 3.5 h. After cooling to 23° C., the reaction mixture was eluted through a pad of silica gel (100 g) and $Na_2SO_4$ with $Et_2O$ (100 mL) to remove the by-products triphenylphosphine oxide and water. The eluent was distilled to remove $Et_2O$ and to afford the product as a colorless liquid (1.0 g, 86%).

D. 4,4,4-Trifluoro-2-(2,2,2-trifluoroethyl)-butyric acid ethyl ester 4,4,4-Trifluoro-2-(2,2,2-trifluoroethyl)-but-2-enoic acid ethyl ester (5.0 g, 20.0 mmol) in THF (20 mL) was treated with Pd/C (2.5 g, 5%), and $H_2$ (1 atm.) at 25° C. for 17 h. The reaction mixture was filtered through a pad of the Celite® reagent, rinsed with $Et_2O$ (50 mL) and the filtrate was distilled to remove $Et_2O$ and THF to afford the product as colorless liquid (5.0 g, 99%).

E. 4,4,4-Trifluoro-2-(2,2,2-trifluoroethyl)-butan-1-ol

To a suspension of LAH (1.0 g) in $Et_2O$ (100 mL) at 25° C. was added slowly 4,4,4-trifluoro-2-(2,2,2-trifluoroethyl)-butyric acid ethyl ester (5.0 g, 19.8 mmol). The resulting mixture was stirred at reflux for 4 h. The cooled reaction mixture was quenched sequentially with water (1.0 mL), 15% NaOH in water (1.0 mL) and water (3.0 mL). After the resulting mixture was allowed to stir at 25° C. for 17 h, $Na_2SO_4$ (20 g) was added and stirring at 25° C. continued for 1 h. The resulting suspension was filtered through a pad of the Celite® reagent and $Na_2SO_4$. The filtrate was distilled to remove all solvents to afford the desired product as a colorless liquid (1.7 g, 41%). Mass Spectrum (−ESI): 269 [M+OAc]−

F. 4,4,4-Trifluoro-2-(2,2,2-trifluoro-ethyl)-butyraldehyde

A solution of 4,4,4-trifluoro-2-(2,2,2-trifluoroethyl)butan-1-ol (1.5 g, 7.14 mmol) in $CH_2Cl_2$ saturated with water (30 mL) was stirred under nitrogen at 0° C. Dess-Martin periodinane reagent (6.35 g, 14.99 mmol) was added in one portion. The resulting suspension was stirred at 25° C., monitoring the progress of reaction by TLC analysis (1:2 EtOAc/hexane). As the rate of conversion of the starting material slowed, additional 2 mL portions of $CH_2Cl_2$ saturated with water were added (three portions over 15 min). After 19 h at 25° C., the reaction was complete by TLC. The solution was diluted with $Et_2O$ (50 mL) and a solution of sodium thiosulfate, $Na_2S_2O_3$ (73.33 mmol, 11.6 g, 11 eq) in 80% saturated aqueous sodium bicarbonate solution (50 mL) was added. The mixture was stirred rapidly for 10 min until both phases were clear. The layers were separated and the aqueous phase was extracted with ether (30 mL). The combined organic layers were washed sequentially with saturated aqueous sodium bicarbonate (10 mL) and brine (15 mL), then dried over $MgSO_4$, filtered and concentrated to 50% of its original volume to give 4,4,4-trifluoro-2-(2,2,2-trifluoro-ethyl)-butyraldehyde as a solution (20 mL). Mass Spectrum (+ESI): (M+H)+.

G. 5-(3,3,3-Trifluoro-1-(2,2,2-trifluoroethyl)propyl)imidazolidine-2,4-dione To sodium cyanide (0.425 g, 8.65 mmol) and ammonium carbonate (0.9 g, 11.54 mmol) in $H_2O$ (30 mL) was added 4,4,4-trifluoro-2-(2,2,2-trifluoroethyl)butyraldehyde (0.6 g, 2.88 mmol) in ethanol (30 mL). The black reaction mixture was heated to 90° C. After 1 h, the mixture became homogeneous and was stirred at 90° C. for 18 h. After cooling to 25° C., about 40 mL of solvent was removed in vacuo. Concentrated HCl (4 mL) was added to acidify the mixture to pH 1-2 and a precipitate formed. It was filtered. The mother liquor washed with EtOAc (3×50 mL). The organic layer was dried over $MgSO_4$, filtered and concentrated to obtain 5-(3,3,3-trifluoro-1-(2,2,2-trifluoroethyl)propyl)imidazolidine-2,4-dione as a brown oil (1.01 g, 100%). Mass Spectrum (+ESI): 279, 280 (M+H)+.

H. 5,5,5-Trifluoro-3-(2,2,2-trifluoroethyl)-dl-norvaline 5-(3,3,3-Trifluoro-1-(2,2,2-trifluoroethyl)propyl)imidazolidine-2,4-dione (1.0 g, 3.59 mmol) was dissolved in a 10 mL solution of aqueous NaOH (0.575 g in 10 mL $H_2O$, 14.38 mmol). The solution was divided in 2 special vessels for microwave technology. The solution was heated by microwave in sealed vessels for 1 h. Microwave conditions: 15 min at about 100% power, 150° C., 50 psi, then 5 min at rest, 0% power. The sequence was repeated until the reaction was done. Water and ammonia were removed from the reaction mixture in vacuo and the resulting crude 5,5,5-trifluoro-3-(2,2,2-trifluoroethyl)-dl-norvaline (0.92 g, 100%) and NaOH mixture was used in the next reaction without further purification. Mass Spectrum (+ESI): 254 (M+H)+.

I. N-[(5-Chlorothien-2-yl)sulfonyl]-5,5,5-trifluoro-3-(2,2,2-trifluoroethyl)-dl-norvaline The crude 5,5,5-trifluoro-3-(2,2,2-trifluoroethyl)-dl-norvaline (0.92 g, 3.56 mmol) and NaOH mixture was dissolved in water (10 ml). The mixture was cooled to 0° C. in an ice bath. 5-Chlorothiophene-2-sulfonyl chloride (0.852 g, 3.9 mmol) was dissolved in THF (10 mL) and added dropwise to the reaction mixture over 10 min. After 60 min, the reaction mixture was allowed to warm gradually to 25° C. and stirred for 16 h. THF was removed in vacuo and the mixture was acidified to pH <2 with 1N HCl. After 15 min, a precipitate began to crash out of the milky white mixture. After 60 min, the mixture was cooled in a refrigerator for 45 min and then filtered. The precipitate was washed with 1N HCl (10 mL) to provide a white solid which gummed out. It was dissolved in EtOAc (100 mL). The aqueous layer washed with EtOAc (3×50 mL) and the organic layers were washed with saturated aqueous NaCl (50 mL). The organic layer was dried over $MgSO_4$, filtered and concentrated to afford N-[(5-chlorothien-2-yl)sulfonyl]-5,5,5-trifluoro-3-(2,2,2-trifluoroethyl)-dl-norvaline as a brown oil (1.3 g, 86.3%). Mass Spectrum (+ESI): 434 (M+H)+.

J. Methyl N-[(5-chlorothien-2-yl)sulfonyl]-5,5,5-trifluoro-3-(2,2,2-trifluoroethyl)-dl-norvalinate To a solution of N-[(5-chlorothien-2-yl)sulfonyl]-5,5,5-trifluoro-3-(2,2,2-trifluoroethyl)-dl-norvaline (1.3 g, 5.23 mmol) in $CH_2Cl_2$:MeOH (4:1) $TMSCHN_2$ (6 mL, 12 mmol) was added dropwise over 10 min at 0° C. until a neon yellow color persisted. When the dropwise addition was completed, the reaction mixture was allowed to warm to 25° C. over 19 h.

The solvent was removed in vacuo to obtain methyl N-[(5-chlorothien-2-yl)sulfonyl]-5,5,5-trifluoro-3-(2,2,2-trifluoroethyl)-dl-norvalinate (0.5 g, 37.31%). Mass Spectrum (−ESI): 445 (M−H)⁻.

K. 5-Chloro-N-[4,4,4-trifluoro-1-(hydroxymethyl)-2-(2,2,2-trifluoroethyl)butyl]thiophene-2-sulfonamide To a solution of methyl N-[(5-chlorothien-2-yl)sulfonyl]-5,5,5-trifluoro-3-(2,2,2-trifluoroethyl)-dl-norvalinate (0.5 g, 1.11 mmol) in THF (10 mL) was added LiBH₄ (2.28 mL, 4.46 mmol) under N₂ atmosphere at 0° C. The reaction was allowed to warm to 25° C. for 19 h. The reaction was cooled to 0° C. and quenched with 2N HCl (slow addition), diluted in ether (40 mL) and the organic layer washed sequentially with 1N aqueous HCl (10 mL), saturated aqueous NaHCO₃ (10 mL) and brine (15 mL), then dried over MgSO₄, filtered and concentrated to obtain a crude oil (0.362 g). The crude product was purified by the Biotage Flash™ 12 chromatography system, eluent: 1:6 EtOAc-hexanes, to afford 5-chloro-N-[4,4,4-trifluoro-1-(hydroxymethyl)-2-(2,2,2-trifluoroethyl)butyl]thiophene-2-sulfonamide as a colorless oil (0.001 g, 2.36%). Mass Spectrum (−ESI): 418 (M−H)⁻.

Example 27

5-Chloro-N-[(1S)-(4,4,4-trifluoro-1-(hydroxymethyl)-2-(2,2,2-trifluoroethyl)butyl)]thiophene-2-sulfonamide

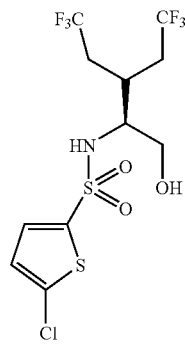

A. 4-Methyl-N-[(1Z)-4,4,4-trifluoro-2-(2,2,2-trifluoroethyl)butylidene]benzenesulfinamide To the crude organic extract of 4,4,4-trifluoro-2-(2,2,2-trifluoroethyl)butyraldehyde (prepared as in Example 26, part F, 0.6 g, 2.88 mmol) in ether (5 mL) was added titanium (IV) ethoxide (2.63 g, 11.54 mmol) followed by (S)-(+)-toluene sulfinamide (0.537 g, 3.46 mmol) and the solution was heated to reflux for 5 h. The mixture was then cooled to 0° C. and water (35 mL) was added to precipitate titanium salts. The suspension was filtered through a pad of the Celite® reagent and the filter cake washed with CH₂Cl₂. The layers of the filtrate were separated and the aqueous layer was extracted with CH₂Cl₂. The combined organic extracts were dried over MgSO₄, filtered, and concentrated to obtain a crude yellow oil (1.05 g). The crude product was purified by the Biotage Flash™ 40 chromatography system, eluent: 1:9 EtOAc-hexanes, to afford 4-methyl-N-[(1Z)-4,4,4-trifluoro-2-(2,2,2-trifluoroethyl)butylidene]benzenesulfinamide as a yellow oil (0.41 g, 41.2%). Mass Spectrum (−ESI): 344 (M−H)⁻.

B. 4-Methyl-N-[(1S)-4,4,4-trifluoro-1-isocyano-2-(2,2,2-trifluoroethyl)butyl]benzenesulfinimide To diethylaluminum cyanide (0.223 mL, 1.73 mmol) in THF (10 mL) at 0° C. was added isopropyl alcohol (76 mg, 1.27 mmol). After 15 min, this solution was added to a −78° C. solution of 4-methyl-N-[(1Z)-4,4,4-trifluoro-2-(2,2,2-trifluoroethyl)butylidene]benzene sulfonamide (0.4 g, 1.158 mmol) in THF (10 mL). After 15 min, the reaction mixture was warmed to 25° C. After 5 h, TLC (1:4 EtOAc-hexane) indicated consumption of starting material. The mixture was cooled to −78° C. and saturated aqueous NH₄Cl (30 mL) was added. The resulting suspension was filtered through a pad of the Celite® reagent and the filter pad washed with EtOAc (2×50 mL). The layers of the filtrate were separated and the aqueous layer was extracted with EtOAc. The combined organic extracts were dried over MgSO₄, filtered, and concentrated to obtain a crude oil (0.360 g).

The crude product was purified by the Biotage Flash™ 40 chromatography system, eluent: 1:6 EtOAc-hexane, to afford 4-methyl-N-[(1S)-4,4,4-trifluoro-1-isocyano-2-(2,2,2-trifluoroethyl)butyl]benzenesulfinimide as a colorless oil (0.065 g, 15.18%). Mass Spectrum (−ESI): 371 (M−H)⁻.

C. 5,5,5-Trifluoro-3-(2,2,2-trifluoroethyl)-L-norvaline

A solution of 4-methyl-N-[(1S)-4,4,4-trifluoro-1-isocyano-2-(2,2,2-trifluoroethyl)butyl]benzenesulfinimide (0.065 g, 0.170 mmol) in concentrated HCl (10 mL) was heated to 100° C. for 19 h. After cooling the mixture to 25° C., it washed with diethyl ether several times. The aqueous layer was concentrated in vacuo to give a mixture of 5,5,5-trifluoro-3-(2,2,2-trifluoroethyl)-L-norvaline, NH₄Cl, and 4-methylbenzenesulfinic acid (0.045 g, 100%). The crude amino acid was used in the next step without further purification. Mass Spectrum (+ESI): 255 (M+H)⁺.

D. (2S)-2-Amino-5,5,5-trifluoro-3-(2,2,2-trifluoroethyl)pentan-1-ol

To a solution of LiBH₄ (0.35 mL, 0.71 mmol) in THF (5 mL) at 0° C. was added chlorotrimethylsilane (0.112 mL, 0.885 mmol). The reaction mixture was warmed to 25° C. and, after 30 min, added dropwise to a 0° C. suspension of crude 5,5,5-trifluoro-3-(2,2,2-trifluoroethyl)-L-norvaline hydrochloride salt (0.045 g, 0.177 mmol) in THF (1 mL). The mixture was warmed to 25° C. and, after 21 h, quenched with MeOH. The volatiles were removed in vacuo to give a residue, which was dissolved in 1N aqueous NaOH (5 mL) and extracted with CH₂Cl₂ (4×10 mL). The organic layer was dried over MgSO₄, filtered and concentrated to obtain (2S)-2-amino-5,5,5-trifluoro-3-(2,2,2-trifluoroethyl)pentan-1-ol as a crude light yellow oil (0.046 g, 100%). The crude amino alcohol was used in the next step without further purification. Mass Spectrum (+ESI): 240 (M+H)⁺.

E. 5-Chloro-N-[(1S)-(4,4,4-trifluoro-1-(hydroxymethyl)-2-(2,2,2-trifluoroethyl)butyl)]thiophene-2-sulfonamide 5-Chlorothiophene-2-sulfonyl chloride (0.193 g, 0.654 mmol) was added dropwise (5 min) as a solution in CH₂Cl₂ (1.0 mL) to a 0° C. solution of (2S)-2-amino-5,5,5-trifluoro-3-(2,2,2-trifluoroethyl)pentan-1-ol (0.042 g, 0.175 mmol) in CH₂Cl₂ (1.0 mL) and pyridine (0.1 mL, 1.09 mmol). The solution was allowed to warm to 25° C. overnight (19 h). An aliquot was taken and TLC (1:2 EtOAc-hexane) indicated that reaction was complete. It was diluted with CH₂Cl₂ (10 mL) and the organic layer was washed with 1N HCl (2×5 mL), saturated aqueous NaCl (5 mL). The organic layer was dried over MgSO₄, filtered and concentrated to obtain a crude off white solid (0.014 g). The crude product was purified by the Biotage Flash™ 12 chromatography system, eluent: 1:4 EtOAc-hexanes, to afford 5-chloro-N-[(1S)-(4,4,4-trifluoro-1-(hydroxymethyl)-2-(2,2,2-trifluoroethyl)butyl)]thiophene-2-sulfonamide as a white solid (0.003 g, 4.1%). Mass Spectrum (+ESI): 420 (M+H)⁺.

Example 28

4,5-Dichloro-N-[3,3,3-trifluoro-1-(hydroxymethyl)-2-(trifluoromethyl)propyl]thiophene-2-sulfonamide

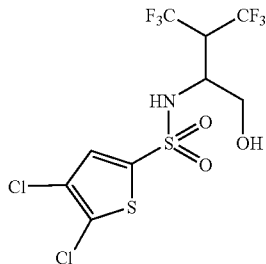

A. 3,3,3-Trifluoro-2-(trifluoromethyl)-1-(hydroxymethyl)propylamine

A solution of lithium borohydride (2M THF, 19.8 mL) was added to a solution of 2-amino-4,4,4-trifluoro-3-trifluoromethyl-butyric acid ethyl ester (5 g, 19.8 mmol), prepared as described (J. Med Chem. 1981, 24, 1043-1047), in THF (80 mL) at 25° C. and was stirred for 4 h. 2M HCl was added to the reaction mixture very carefully until a pH less than 2. The organic solvent was removed in vacuo and the aqueous layer was neutralized with sat NaHCO₃ until pH=7. The aqueous layer was extracted with EtOAc (2×50 mL) and the organic extracts were dried over Na₂SO₄ and concentrated to provide 3,3,3-trifluoro-2-(trifluoromethyl)-1-(hydroxymethyl)propylamine as a yellow oil (3.2 g, 77% yield). The crude oil was of sufficient purity to utilize in the subsequent reaction.

B. 4,5-Dichloro-N-[3,3,3-trifluoro-1-(hydroxymethyl)-2-(trifluoromethyl)propyl]thiophene-2-sulfonamide A solution of 3,3,3-trifluoro-2-(trifluoromethyl)-1-(hydroxymethyl)propylamine (0.192 g, 0.9 mmol) in THF (1 mL) was stirred under nitrogen at 25° C. Pyridine (0.147 mL, 1.82 mmol) was added followed by 4,5-dichlorothiophene-2-sulfonyl chloride (0.226 g, 0.391 mmol) in THF (1 mL), and the resulting solution stirred for 18 h at 25° C. After concentration, the residue was taken up in EtOAc (15 mL) and washed with 1 N aq. HCl (10 mL), brine (10 mL), and then dried (Na₂SO₄). After concentration, the crude product was purified by preparatory TLC, eluent: 30:70 EtOAc:hexanes, to provide 4,5-dichloro-N-[3,3,3-trifluoro-1-(hydroxymethyl)-2-(trifluoromethyl)propyl]thiophene-2-sulfonamide as a white solid (0.037 g, 9% yield, racemic mixture). Mass Spectrum (-ESI): 423.9 (M-H)⁻.

Example 29

N-[(1S)-3,3,3-Trifluoro-1-(hydroxymethyl)-2-(trifluoromethyl)propyl]thiophene-3-sulfonamide

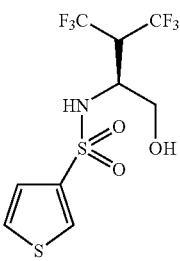

A solution of (1S)-3,3,3-trifluoro-2-(trifluoromethyl)-1-(hydroxymethyl)propylamine (prepared according to the method of Example 13, 0.100 g, 0.4 mmol) in CH₂Cl₂ (1 mL) was stirred under nitrogen at 25° C. Pyridine (0.097 mL, 1.2 mmol) was added followed by 3-thiophenesulfonyl chloride (0.072 g, 0.4 mmol) in CH₂Cl₂ (0.5 mL), and the resulting solution stirred for 18 h at 25° C. The crude reaction mixture was loaded onto the TsOH Syntage™ samplet and after concentration was purified by the Biotage Flash™ 12 chromatography system, eluent: 30:70 EtOAc:hexanes, to obtain N-[(1S)-3,3,3-trifluoro-1-(hydroxymethyl)-2-(trifluoromethyl)propyl]thiophene-3-sulfonamide as a white solid (0.053 g, 35% yield).

Mass Spectrum (-ESI): 355.9 (M-H)⁻.

Anal: Calc'd for C₉H₈ClF₆NO₃S₂ C, 30.25; H, 2.54; N, 3.92;

Found: C, 30.55; H, 2.27; N, 3.77.

Example 30

2,5-Dichloro-N-[(1S)-3,3,3-trifluoro-1-(hydroxymethyl)-2-(trifluoromethyl)propyl]thiophene-3-sulfonamide

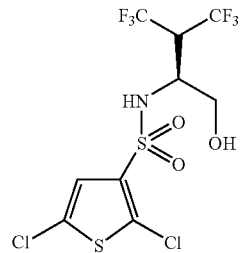

The procedure described in example 29 was followed with the exception that 2,5-dichlorothiophene-3-sulfonyl chloride was used to provide 2,5-dichloro-N-[(1S)-3,3,3-trifluoro-1-(hydroxymethyl)-2-(trifluoromethyl)propyl]thiophene-3-sulfonamide as a white solid (0.026 g, 17% yield). Mass Spectrum (-ESI): 423.8 (M-H)⁻.

Example 31

N-[(1S)-3,3,3-Trifluoro-1-(hydroxymethyl)-2-(trifluoromethyl)propyl]thiophene-2-sulfonamide

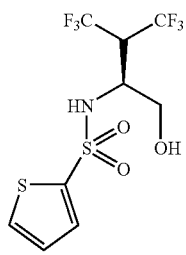

The procedure described in example 29 was followed with the exception that 2-thiophenesulfonyl chloride was used to provide N-[(1S)-3,3,3-trifluoro-1-(hydroxymethyl)-2-(trifluoromethyl)propyl]thiophene-2-sulfonamide as a white solid (0.024 g, 17% yield). Mass Spectrum (−ESI): 355.9 (M−H)⁻.

Example 32

4,5-Dichloro-N-[(1S)-3,3,3-trifluoro-1-(hydroxymethyl)-2-(trifluoromethyl)propyl]thiophene-2-sulfonamide

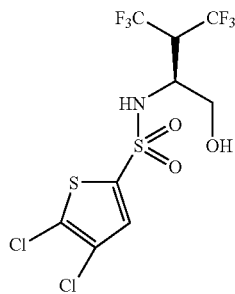

The procedure described in example 29 was followed with the exception that 4,5-dichlorothiophene-2-sulfonyl chloride was used to provide 4,5-dichloro-N-[(1S)-3,3,3-trifluoro-1-(hydroxymethyl)-2-(trifluoromethyl)propyl]thiophene-2-sulfonamide as a white solid (0.050 g, 29% yield). Mass Spectrum (−ESI): 423.8 (M−H)⁻.

Example 33

Thiophene-2-sulfonic acid (3,3,3-trifluoro-1-hydroxymethyl-2-trifluoromethyl-propyl)-amide

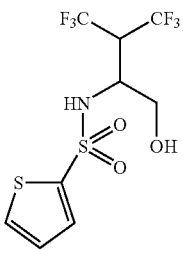

To a solution of 3,3,3-trifluoro-2-(trifluoromethyl)-1-(hydroxymethyl)propylamine (prepared according to the method of Example 28, Part A, 105 mg, 0.5 mmol) in $CH_2Cl_2$ (1 mL) was added pyridine (100 μL) and 2-thiophenesulfonyl chloride (90.5 mg, 0.5 mmol) in $CH_2Cl_2$ (1 mL). The solution was stirred for about 8 to about 16 h at 25° C. and then concentrated. EtOAc (1 mL) was added and the solution washed with 1M HCl (1 mL), brine (1 mL), dried over $Na_2SO_4$ and concentrated. The crude solid was purified by the Biotage Flash™ 12 chromatography system, eluting with EtOAc/hexanes (2:3), to give thiophene-2-sulfonic acid (3,3,3-trifluoro-1-hydroxymethyl-2-trifluoromethyl-propyl)-amide (26.5 mg) as a white solid.

The following compounds (Examples 33-35, Table 1) were prepared using 2-thiophenesulfonyl chloride, 3-thiophenesulfonyl chloride and 2,5-dichlorothiophene-3-sulfonyl chloride and employing the procedure outlined in Example 33.

TABLE 1

(LCMS Data*: Molecular ion and retention time)

$$F_3C\diagdown\diagup CF_3 \quad \xrightarrow{RSO_2Cl,\ pyr,\ CH_2Cl_2} \quad F_3C\diagdown\diagup CF_3$$

| RSO₂Cl | 3,3,3-trifluoro-2-(trifluoromethyl)-1-(hydroxymethyl)propylamine |
|---|---|
| 2-thiophenesulfonyl chloride | Example 33 (356 M-H); 2.063 min |
| 3-thiophenesulfonyl chloride | Example 34 (356 M-H); 2.013 min |
| 2,5-dichlorothiophene-3-sulfonyl chloride | Example 35 (424 M-H); 2.564 min |

*Hewlett Packard Series 1100 HPLC/MS, Luna C18 2 × 30 mm column, elution gradient: 40% acetonitrile/water (0.1% HCOOH) to 100% acetonitrile (0.1% HCCOH) over 3 minutes at a flow rate of 0.6 mL/min.

Example 36

Dibromo-N-[3,3,3-trifluoro-1-(hydroxymethyl)-2-(trifluoromethyl)propyl]thiophene-2-sulfonamide

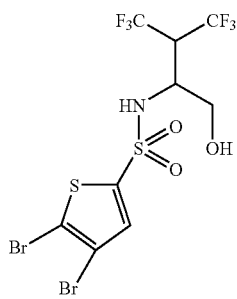

To a solution of 3,3,3-trifluoro-2-(trifluoromethyl)-1-(hydroxymethyl)propylamine (prepared according to the method of Example 28, Part A, 105 mg, 0.5 mmol) in CH$_2$Cl$_2$ (1 mL) was added pyridine (100 μL) and 4,5-dibromo thiophene-2-sulfonyl chloride (170 mg, 0.5 mmol) in CH$_2$Cl$_2$ (1 mL). The solution was stirred for about 8 to about 16 h at 25° C. and then concentrated. EtOAc (1 mL) was added and the solution washed with 1M HCl (1 mL), brine (1 mL), dried over Na$_2$SO$_4$ and concentrated. The crude solid was taken up in DMSO (0.5 mL) and purified by reverse phase HPLC (the Gilson® HPLC instrument, the Luna® C18 100×30 mm column, elution gradient: 40% acetonitrile/water (0.075% TFA) to 100% acetonitrile (0.075% TFA) over 15 min at a flow rate of 20 mL/min) providing the title compound (13.8 mg) as a white solid.

The following compounds (Examples 36-39, Table 2) were prepared using 4,5 dibromothiophene-2-sulfonyl chloride, 2-bromo-5-chloro thiophene-2-sulfonyl chloride, 3-bromo-2,5-dichlorothiophene-3-sulfonyl chloride and benzothiophene-2-sulfonyl chloride and employing the procedure outlined in Example 36.

TABLE 2

(LCMS Data*: Molecular ion and retention time)

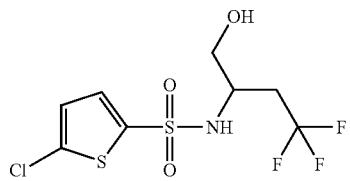

| RSO$_2$Cl | 3,3,3-trifluoro-2-(trifluoromethyl)-1-(hydroxymethyl)propylamine |
|---|---|
| 4,5-dibromothiophene-2-sulfonyl chloride | Example 36 (514.1 M-H); 1.882 min |
| 3-bromo-5-chlorothiophene-2-sulfonyl chloride | Example 37 (470.1 M-H); 1.699 min |
| 4-bromo-2,5-dichlorothiophene-3-sulfonyl chloride | Example 38 (504.0 M-H); 1.916 min |
| benzothiophene-2-sulfonyl chloride | Example 39 (406.2 M-H); 1.508 min |

*Hewlett Packard Series 1100 HPLC/MS, Luna C18 2 × 30 mm column, elution gradient: 40% acetonitrile/water (0.1% HCOOH) to 100% acetonitrile (0.1% HCCOH) over 3 minutes at a flow rate of 0.6 mL/min.

Example 40

Chloro-(3,3,3-trifluoro-1-hydroxymethyl-propyl)-thiophene-2-sulfonamide

A. 2-Amino-4,4,4-trifluoro-butan-1-ol

A solution of trimethylsilyl chloride (1.38 g, 12.73 mmol) was added to a solution of lithium borohydride (3.2 mL, 2.0 M in THF) and THF (5 mL) at 25° C. After stirring 5 min, 2-amino-4,4,4-trifluoro-butyric acid (0.50 g, 3.18 mmol) was added portionwise over a 5 min period. The reaction was allowed to stir 48 h. The reaction was quenched by cautious addition of MeOH (5 mL) dropwise. The solvent was evaporated and the residue treated with potassium hydroxide (KOH) solution (20%, 6 mL). The aqueous phase was extracted using dichloromethane, 3 times (10 mL each). The organic phases were combined and dried over anhydrous sodium sulfate. After filtration the solvent was evaporated to afford the 2-amino-4,4,4-trifluoro-butan-1-ol as an oil (0.174 g, 38%). This oil was used directly in the next reaction without further purification.

B. 5-Chloro-(3,3,3-trifluoro-1-hydroxymethyl-propyl)-thiophene-2-sulfonamide To a solution of 2-amino-4,4,4-trifluoro-butan-1-ol (0.161 g, 1.12 mmol) in dry CH$_2$Cl$_2$ (4 mL) at 25° C. under nitrogen was added dropwise Et$_3$N (0.17 mL, 1.23 mmol) followed also by dropwise addition of 5-chlorothiophene-2-sulfonyl chloride (0.243 g, 1.12 mmol) as a solution in dichloromethane (1 mL). The reaction was stirred for 18 h at 25° C. The reaction was then quenched by pouring it into a separatory funnel containing saturated NaHCO$_3$ solution. Additional CH$_2$Cl$_2$ (15 mL) was added. After extraction, the organic layer washed with 1N HCl solution, distilled water and brine. The organic phase was then dried over MgSO$_4$ and concentrated to a crude solid. After concentration, the crude product was purified by flash chromatography, eluent:hexane:EtOAc, 4:1 to 2:1, to obtain 5-chloro-(3,3,3-trifluoro-1-hydroxymethyl-propyl)-thiophene-2-sulfonamide as a clear oil that crystallized under vacuum (0.191 g, 53%).

Mass Spectrum (−ESI): 321.9 (M−H)⁻.

Anal: Calc'd for C$_8$H$_9$ClF$_3$NO$_3$S$_2$ C, 29.68; H, 2.80; N, 4.33;

Found: C, 29.75; H, 2.72; N, 4.10.

Example 41

5-Chloro-N-[(1S)-3,3,3-trifluoro-1-[(1R)-1-hydroxy-ethyl]-2-(trifluoromethyl)propyl]thiophene-2-sulfonamide

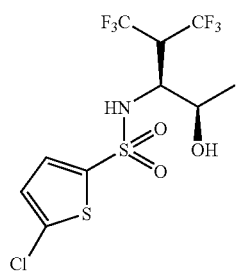

A. 5-Chloro-N-[3,3,3-trifluoro-2-(trifluoromethyl)-1-S-(formyl)propyl]thiophene-2-sulfonamide A solution of 5-chloro-N-[3,3,3-trifluoro-2-(trifluoromethyl)-1-S-(hydroxymethyl)propyl]thiophene-2-sulfonamide (prepared according to Example 5, 0.200 g, 0.511 mmol) in $CH_2Cl_2$ (10 mL) was stirred under nitrogen at 0° C. Dess-Martin periodinane reagent (0.325 g, 0.767 mmol) was added in one portion, and the solution stirred for 1 h at 0° C. After an additional 1 h at 25° C., the reaction was complete by TLC (30:70 EtOAc:PE). The solution was diluted with $Et_2O$ (100 mL), and to this solution was added $Na_2S_2O_3$ (1.10 g) in sat. aq. $NaHCO_3$ (10 mL). The resulting mixture was stirred for 0.5 h. The liquid layers were separated, and the organic layer washed with additional sat. aq. $NaHCO_3$ (10 mL) and brine (10 mL) and then dried ($Na_2SO_4$). After concentration, the resulting residue (0.190 g, 95%) was used directly in the next reaction without further purification.

B. 5-Chloro-N-[(1S)-3,3,3-trifluoro-1-[(1R)-1-hydroxyethyl]-2-(trifluoromethyl)propyl]thiophene-2-sulfonamide A solution of 5-chloro-N-[3,3,3-trifluoro-2-(trifluoromethyl)-1-S-(formyl)propyl]thiophene-2-sulfonamide (0.188 g, 0.482 mmol) in THF (5 mL) was stirred under nitrogen at 0° C. Methyl magnesium bromide (0.482 mL, 3.0 M in $Et_2O$) was added dropwise, and the resulting solution stirred for 2 h at 25° C. After this time period, the reaction was complete by TLC (30:70 EtOAc:PE). The solution was quenched with sat. aq. $NH_4Cl$ (10 mL) and then extracted with $Et_2O$ (100 mL). The organic layer washed with brine (10 mL) and then dried ($Na_2SO_4$). After concentration, the crude product was purified by preparatory plate chromatography, eluent: 30:70 EtOAc:PE, followed by chiral HPLC [the Chiralcel® OJ column; 2×25 cm, 254 nm, 0.6 mL injections; mobile phase: 10 mL/min 10% EtOH in 7200; product is peak one, $R_f$=6.106, 99.9% purity] to obtain the major diastereomer, 5-chloro-N-[(1S)-3,3,3-trifluoro-1-[(1R)-1-hydroxyethyl]-2-(trifluoromethyl)-propyl]thiophene-2-sulfonamide, as an off-white solid (0.043 g, 22%). Mass Spectrum (−ESI): 404 (M−H)⁻.

Anal: Calc'd for $C_{10}H_{10}ClF_6NO_3S_2$ C, 29.60; H, 2.48; N, 3.45.

Found: C, 29.59; H, 2.40; N, 3.41.

Example 42

Aβ40/42 ELISA Assay

A. Short Description of the Assay:

Compounds are diluted from DMSO stocks to 2 µM and below in a cell culture medium. Compounds are then applied to CHO cells carrying the APP-REP-NL plasmid [Sudhir et. al, J. Biolog. Chem. 267:25602-25608 (1992)] for a period of 22 hours. After the conditioning period, medium is collected, diluted in assay buffer containing protein, and samples, controls, and synthetic peptide standards are incubated on a prepared ELISA plate. Using a sandwich ELISA with antibodies specifically directed against the carboxyl terminus of beta amyloid 40 or 42 [analogous to the method reported by Haugabook et al., J. Neurosci. Methods 108:171-179 (2001) but using goat anti-mouse IgG1 (source: Southern Biotech) as the anchor, 6E10 as the capture antibody (Source: SENETEK), rabbit antiAβ40 and antiAβ42 (source: QCB) and APL-donkey anti-rabbit IgG (H+L, source: Southern Biotech) as the detection antibody], the effect of the compound treatment on the cellular production of extracellular beta amyloid is quantified. Cells treated with compound are subsequently incubated in cell culture medium containing MTS-formazan. After a short incubation period, MTS/medium containing plates are read in a spectrophotometer to determine the extent to which compound toxicity affected the cell's metabolism and ability to synthesize beta amyloid.

B. Materials for the Assay:

(i) Test Samples: compound samples are supplied as 20 mM stock solutions in a 100% DMSO solution.

(ii) APP-REP-NL cells: Qualified cell lines are carried from week to week using 1:100 dilutions and are cultured in DMEM supplemented with 1× antibiotic/antimycotic, 200 ug/ml of G418 antibiotic, and 10% certified fetal calf serum. Cells are also banked in liquid nitrogen. Periodically, beta amyloid production is assessed, and cells are either kept in culture or replaced with progenitors at full expression.

(iii) Antibodies: Are from certified lots that have already been qualified in this assay. Antibodies are stored in small frozen aliquots at −80° C. that are thawed and used.

(iv) Reagents: are of the highest quality available. Certain reagents are "lot specific" and only reagents from that specific manufacturer and lot may be used.

(v) Plasticware: is of the highest quality available.

C. Criteria for Activity

A compound is considered active if it has an $EC_{50}$ for Aβ40 reduction of <100 µM and no toxicity at doses in the vicinity the $EC_{50}$.

D. Standard Beta Amyloid Inhibitor

The reference gamma secretase inhibitor DAPT (LY374973, AN37124: Dovey, H. F. et al., J. Neurochem. 76: 173-181 (2001)) was prepared as outlined in WO 98/22494 and tested in the Ab40/42 ELISA and gave Aβ40$EC_{50}$=171 nM and Aβ42$EC_{50}$=128 nM.

Example 43

Repressor Release Assay (RRA)

The compounds generated as described in the Examples above are tested in the RRA in accordance with published techniques [Shuey, D. J., Sheiffele, P., Jones, D., Cockett, M. I., and Quinet, E. M. (1999), "Repressor release: a useful tool for monitoring amyloid precursor protein (APP) proteolysis in mammalian cells", Society for Neuroscience Abstracts, Vol. 25, 29$^{th}$ Annual Meeting of Society for Neuroscience, Miami Beach, Fla., Oct. 23-28, 1999]. Briefly, this assay is performed as follows.

A. Cell Culture

CHO-K1 cells are cultured in whole DMEM media (DMEM—High Glucose with 10% fetal bovine serum, 1% Non-essential Amino Acids, and 1% Penicillin-Streptomycin) at 37° C. with 5% $CO_2$. Two million cells are plated into 10-cm dishes 24 hrs prior to transfection.

Transient transfections are completed as recommended by Gibco BRL using their Lipofectamine Plus® system. First, 6 µg of pRSVO-luc and 6 µg of APP-lacI construct DNA are added to 460 µL Opti-Mem transfection media and incubated with the 30 µL Plus® reagent for 15 minutes. Then, a lipid mixture of 40 µL Lipofectamine Plus® reagent and 460 µL Opti-Mem transfection media is incubated with the DNA-Plus reagent mixture for 15 minutes. During the DNA-lipid incubation, the CHO-K1 cells are washed once and covered in 5.0 mL DMEM media without Penicillin-Streptomycin. The DNA-lipid preparation is then layered onto these cells and incubated at 37° C. overnight.

One and one half million transfected cells per well (100 µL total volume) are plated into sterile, opaque Packard 96-well Cultur-Plates™ in clear DMEM whole media (DMEM—without phenol red) and incubated at 37° C. with 5% $CO_2$ for 3-5 hours.

B. Compound Dilution

Compounds are diluted using two different protocols; one protocol is used for compounds supplied neat (weighed powder in vial) and the other protocol is used for compounds supplied in solution (20 mM in DMSO in 96-well plates). For both protocols, 25 mM Hepes and 25 mM Hepes/1% DMSO are prepared fresh to be used as diluent. The Hepes/DMSO is used as the diluent control on all experimental plates.

The following table depicts the steps for compound dilution (please note that the last step is the addition of compound to cells/media in tissue culture plate):

TABLE 3

| | Concentration | Dilution |
|---|---|---|
| Stock Solution | 10 mg/mL | x mg compound (vial) diluted with 100% DMSO |
| Dilution 1 | 1 mg/mL | 20 µL stock solution 180 µL 25 mM Hepes |
| Dilution 2 | 200 µg/mL | 60 µL Dilution 1 240 µL 25 mM Hepes |
| Dilution 3 (in Cell Plate) | 20 µg/mL | 11.3 µL Dilution 2 (in 100 µL cells/well) |

Because some compounds arrive in 96-well format at 20 mM, the following represents the protocol for their dilution (note that an average molecular weight of these compounds was used to calculate these dilutions and as above, the last step is the addition of compound to cells/media in tissue culture plate):

TABLE 4

| | Concentration | Dilution |
|---|---|---|
| Stock Solution (original conc.) | — | 20 mM Solution |
| Dilution 1 | about 200 µg/mL | 6 µL stock solution 194 µL 25 mM Hepes |
| Dilution 2 (in Cell Plate) | about 20 µg/mL | 11.3 µL Dilution 2 (in 100 µL cells/well) |

Once compounds are diluted, they are applied in duplicate on cells in tissue culture plates (prepared above). Cells are incubated with compound at 37° C. with 5% $CO_2$ for an additional 36-48 hours.

C. Assay Measurement

Luciferase assays (the LucLite® reagent, Packard) are performed and are read on a Packard TopCount® instrument. Media is removed from each 96-well plate and replaced with 100 µL PBS per well (with $Mg^{2+}$ and $Ca^{2+}$). An equal volume (100 µL) of the LucLite® lysis/substrate buffer is added to each well and the plates are sealed and mixed in the dark on a rotary shaker for about 15 to about 30 minutes at room temperature. Luciferase readings are then taken on the TopCount® instrument. Measurements are expressed as relative light units (RLU) and are calculated and analyzed in the MS Excel® program as follows.

D. Analysis of Data

The results of the assay with respect to the compounds exemplified herein are provided in the following table. A compound is considered active in RRA if it leads to at least a 1.5 fold increase in luciferase activity at 20 µg/mL and is non-toxic, as determined by loss of signal ($\leq 0.75$ fold increase). Fold increase is the amount of luciferase activity (measured in relative light units) over diluent control. SEM represents the standard error of the mean for fold increase (not shown). All compounds tested were found to be non-toxic.

E. Standard Beta Amyloid Inhibitor

The reference gamma secretase inhibitor DAPT (LY374973, AN37124: Dovey, H. F. et al., J. Neurochem. 76: 173-181 (2001)) was prepared as outlined in International Patent Publication No. WO 98/22494 and tested in RRA and exhibited a 18.5-28.1 fold increase in luciferase activity at 20 µg/mL.

TABLE 5

Exemplary Compounds of the Invention:

| Ex # | RRA data* | Name |
|---|---|---|
| 1 | 3.2 3.7 | 5-chloro-N-[(1S,2R)-4,4,4-trifluoro-1-(hydroxymethyl)-2-methylbutyl]thiophene-2-sulfonamide |
| 2 | 3.7 4.3 5.4 | 5-chloro-N-[(1S,2R)-2-ethyl-4,4,4-trifluoro-1-(hydroxymethyl)butyl]thiophene-2-sulfonamide |

TABLE 5-continued

Exemplary Compounds of the Invention:

| Ex # | RRA data* | Name |
|---|---|---|
| 3 | 4.3 | 5'-chloro-N-[(1S,2R)-2-ethyl, 4,4,4-trifluoro-1-(1-hydroxyethyl)butyl]thiophene-2'-sulfonamide |
| 4 | 3.7 | 5'-chloro-N-[3,3,3-trifluoro-2-(trifluoromethyl)-1-(hydroxymethyl)propyl]thiophene-2'-sulfonamide |
| 5 | 3.8 | 5'-chloro-N-[3,3,3-trifluoro-2-(trifluoromethyl)-1-S-(hydroxymethyl)propyl]thiophene-2'-sulfonamide |
| 6 | 4.2 | 5-chloro-N-[(1R,2S)-2-ethyl-4,4,4-trifluoro-1-(hydroxymethyl)butyl]thiophene-2-sulfonamide |
| 7 | 3.9 | 5-chloro-N-[4,4,4-trifluoro-1-(hydroxymethyl)butyl]thiophene-2-sulfonamide |
| 8 | 2.8 | 5-chloro-N-{(1S,2R)-4,4,4-trifluoro-1-[(1S)-1-hydroxyethyl]-2-methylbutyl}thiophene-2-sulfonamide |
| 9 | 2.8 | 5-chloro-N-{(1S,2R)-4,4,4-trifluoro-1-[(1R)-1-hydroxyethyl]-2-methylbutyl}thiophene-2-sulfonamide |
| 10 | 5.2 | 5-chloro-N-[(1S,2S)-4,4,4-trifluoro-1-(hydroxymethyl)-2-methylbutyl]thiophene-2-sulfonamide |
| 11 | 4.2 | 2S,3S)-2-(5-chloro-3-methylbenzo[b]thiophene-2-sulfonyl)-amido-5,5,5-trifluoro-3-ethyl-pentan-1-ol. |
| 12 | 1.6 | (2S,3R)-2-(5-chloro-1,3-dimethyl-1H-pyrazole-4-sulfonyl)-amido-5,5,5-trifluoro-3-phenyl-pentan-1-ol. |
| 14 | 6.2 5.8 | 5-chloro-N-[1-(4,4-difluorocyclohexyl)-2-hydroxyethyl]thiophene-2-sulfonamide. |
| 15 | 4.7 | 5-chloro-N-[1-(6,6-difluorobicyclo[3.1.0]hex-3-yl)-2-hydroxyethyl]thiophene-2-sulfonamide |
| 16 | 3.9 | 5-chloro-N-[(1S,2R)-4,4,4-trifluoro-1-formyl-2-methylbutyl]thiophene-2-sulfonamide |
| 17 | 3.6 | N-[(1S,2R)-1-acetyl-4,4,4-trifluoro-2-methylbutyl]-5-chlorothiophene-2-sulfonamide |
| 18 | 2.9 | 5-chloro-N-[(1S,2R)-4,4,4-trifluoro-1-(1-hydroxy-1-methylethyl)2-methylbutyl]thiophene-2-sulfonamide |
| 19 | | 4-bromo-5-chloro-N-[3,3,3-trifluoro-1-(hydroxymethyl)-2-(trifluoromethyl)propyl]thiphene-2-sulfonamide. |
| 20 | | 4-bromo-5-chloro-N-[(1S)-3,3,3-trifluoro-1-(hydroxymethyl)-2-(trifluoromethyl)propyl]thiophene-2-sulfonamide |
| 21 | | 5-chloro 4-fluoro-N-[3,3,3-trifluoro-1-(hydroxymethyl)-2-(trifluoromethyl)propyl]thiophene-2-sulfonamide |
| 22 | | 5-bromo-N-[3,3,3-trifluoro-1-(hydroxymethyl)-2-(trifluoromethyl)propyl]thiophene-2-sulfonamide |
| 23 | | 5-fluoro-N-[3,3,3-trifluoro-1-(hydroxymethyl)-2-(trifluoromethyl)propyl]thiophene-2-sulfonamide |
| 24 | | 5-bromo-N-[(1S)-3,3,3-trifluoro-1-(hydroxymethyl)-2-(trifluoromethyl)propyl]thiophene-2-sulfonamide |
| 25 | | 5-fluoro-N-[(1S)-3,3,3-trifluoro-1-(hydroxymethyl)-2-(trifluoromethyl)propyl]thiophene-2-sulfonamide |
| 26 | | 5-chloro-N-[4,4,4-trifluoro-1-(hydroxymethyl)-2-(2,2,2-trifluoroethyl)butyl]thiophene-2-sulfonamide |
| 27 | | 5-chloro-N-[(1S)-(4,4,4-trifluoro-1-(hydroxymethyl)-2-(2,2,2-trifluoromethyl)butyl)]thiophene-2-sulfonamide |
| 28 | | 4,5-dichloro-N-[3,3,3-trifluoro-1-(hydroxymethyl)-2-(trifluoromethyl)propyl]thiophene-2-sulfonamide |
| 29 | | N-[(1S)-3,3,3-trifluoro-1-(hydroxymethyl)-2-(trifluoromethyl)propyl]thiophene-3-sulfonamide |
| 30 | | 2,5-dichloro-N-[(1S)-3,3,3-trifluoro-1-(hydroxymethyl)-2-(trifluoromethyl)propyl]thiophene-3-sulfonamide |
| 31 | | N-[(1S)-3,3,3-trifluoro-1-(hydroxymethyl)-2-(trifluoromethyl)propyl]thiophene-2-sulfonamide |
| 32 | | 4,5-dichloro-N-[(1S)-3,3,3-trifluoro-1-(hydroxymethyl)-2-(trifluoromethyl)propyl]thiophene-2-sulfonamide |
| 33 | | thiophene-2-sulfonic acid (3,3,3-trifluoro-1-hydroxymethyl-2-trifluoromethyl-propyl)-amide |
| 34 | | thiophene-3-sulfonic acid (3,3,3-trifluoro-1-hydroxymethyl-2-trifluoromethyl-propyl)-amide |
| 35 | | 2,5-dichloro-thiophene-3-sulfonic acid (3,3,3-trifluoro-1-hydroxymethyl-2-trifluoromethyl-propyl)-amide |
| 36 | | 4,5-dibromo-N-[3,3,3-trifluoro-1-(hydroxymethyl)-2-(trifluoromethyl)propyl]thiophene-2-sulfonamide |
| 37 | | 3-bromo-5-chloro-N-[3,3,3-trifluoro-1-(hydroxymethyl)-2-(trifluoromethyl)propyl]thiophene-2-sulfonamide |
| 38 | | 4-bromo-2,5-dichloro-N-[3,3,3-trifluoro-1-(hydroxymethyl)-2-(trifluoromethyl)propyl]thiophene-3-sulfonamide |
| 39 | | benzo[b]thiophene-2-sulfonic acid (3,3,3-trifluoro-1-hydroxymethyl-2-trifluoromethyl-propyl)-amide |
| 40 | 3.8, 4.2 | 5-chloro-(3,3,3-trifluoro-1-hydroxymethyl-propyl)-thiophene-2-sulfonamide |
| 41 | 6.2 | 5-chloro-N-[(1S)-3,3,3-trifluoro-1-[(1R)-1-hydroxyethyl]-2-(trifluoromethyl)propyl]thiophene-2-sulfonamide |

*fold increase of APPI, all compounds tested at 20 μg/mL.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A method of treating a disease selected from the group consisting of Alzheimer's Disease, amyloid angiopathy, cerebral amyloid angiopathy, systemic amyloidosis, hereditary cerebral hemorrhage with amyloidosis of the Dutch type, inclusion body myositis, mild cognitive impairment (MCI) and Down's syndrome, in a subject, said method comprising administering a compound of formula I to said subject in an amount sufficient to alleviate the symptoms or progress of said disease, wherein said compound of formula I is of the structure:

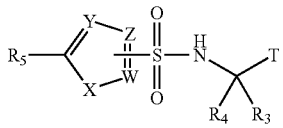

(I)

wherein:
T is selected from the group consisting of CHO, $COR_8$, and $C(OH)R_1R_2$;
$R_1$ and $R_2$ are independently selected from the group consisting of hydrogen, lower alkyl, substituted lower alkyl, $CF_3$, alkenyl, substituted alkenyl, alkynyl, and substituted alkynyl;
$R_3$ is selected from the group consisting of hydrogen, lower alkyl and substituted lower alkyl;
$R_4$ is selected from the group consisting of $(CF_3)_n$alkyl, $(CF_3)_n$(substituted alkyl), $(CF_3)_n$alkylphenyl, $(CF_3)_n$alkyl(substituted phenyl), and $(F)_n$cycloalkyl;
n=1-3;
$R_5$ is selected from the group consisting of hydrogen, halogen, $CF_3$, diene fused to Y when Y=C, and substituted diene fused to Y when Y=C;
W, Y and Z are independently selected from the group consisting of C, $CR_6$ and N with the proviso that at least one of W or Y or Z must be C;
$R_6$ is selected from the group consisting of hydrogen, halogen, lower alkyl, and substituted lower alkyl;
X is selected from the group consisting of O, S, $SO_2$, and $NR_7$;
$R_7$ is selected from the group consisting of hydrogen, lower alkyl, substituted lower alkyl, benzyl, substituted benzyl, phenyl, and substituted phenyl; and
$R_8$ is selected from the group consisting of lower alkyl, $CF_3$, phenyl, and substituted phenyl;
or a pharmaceutically acceptable salt, hydrate, or prodrug thereof.

2. The method according to claim 1, wherein said compound is delivered orally, by injection or by inhalation.

3. The method according to claim 1, wherein $R_5$ is halogen.

4. The method according to claim 1, wherein $R_1$ and $R_2$ are each hydrogen.

5. The method according to claim 1, wherein X is S, W is C, Y is CH, Z is CH, $R_5$ is chlorine, $R_4$ is $CF_3CH_2CHCH_3$, $R_3$, $R_1$ and $R_2$ are each hydrogen, which has 1S, 2R stereochemistry.

6. The method according to claim 1, wherein X is S, W is C, Y is CH, Z is CH, $R_5$ is chlorine, $R_4$ is $CF_3CHCF_3$, $R_3$, $R_1$ and $R_2$ are each hydrogen, which has 1S stereochemistry.

7. The method according to claim 1, wherein said compound is selected from the group consisting of 5-Chloro-N-[(1S,2R)-4,4,4-trifluoro-1-(hydroxymethyl)-2-methylbutyl]thiophene-2-sulfonamide; 5-Chloro-N-[(1S,2R)-2-ethyl-4,4,4-trifluoro-1-(hydroxymethyl)butyl]thiophene-2-sulfonamide; 5'-Chloro-N-[(1S,2R)-2-ethyl, 4,4,4-trifluoro-1-(1-hydroxyethyl)butyl]thiophene-2'-sulfonamide; 5'-Chloro-N-[3,3,3-trifluoro-2-(trifluoromethyl)-1-hydroxymethyl)propyl]thiophene-2'-sulfonamide; 5'-Chloro-N-[3,3,3-trifluoro-2-(trifluoromethyl)-1-S-(hydroxymethyl)propyl]thiophene-2'-sulfonamide; 5-Chloro-N-[(1R,2S)-2-ethyl-4,4,4-trifluoro-1-(hydroxymethyl)butyl]thiophene-2-sulfonamide; 5-Chloro-N-[4,4,4-trifluoro-1-(hydroxymethyl)butyl]thiophene-2-sulfonamide; 5-Chloro-N-{(1S,2R)-4,4,4-trifluoro-1-[(1S)-1-hydroxyethyl]-2-methylbutyl}thiophene-2-sulfonamide; 5-Chloro-N-{(1S,2R)-4,4,4-trifluoro-1-[(1R)-1-hydroxyethyl]-2-methylbutyl}thiophene-2-sulfonamide; 5-Chloro-N-[(1S,2S)-4,4,4-trifluoro-1-(hydroxymethyl)-2-methylbutyl]thiophene-2-sulfonamide; (2S,3S)-2-(5-Chloro-3-methylbenzo[b]thiophene-2-sulfonyl)-amido-5,5,5-trifluoro-3-ethyl-pentan-1-ol; (2S,3R)-2-(5-Chloro-1,3-dimethyl-1H-pyrazole-4-sulfonyl)-amido-5,5,5-trifluoro-3-phenyl-pentan-1-ol; 5-Chloro-N-[1-(4,4-difluorocyclohexyl)-2-hydroxyethyl]thiophene-2-sulfonamide; 5-Chloro-N-[1-(6,6-difluorobicyclo[3.1.0]hex-3-yl)-2-hydroxyethyl]thiophene-2-sulfonamide; 5-Chloro-N-[(1S,2R)-4,4,4-trifluoro-1-formyl-2-methylbutyl]thiophene-2-sulfonamide; N-[(1S,2R)-1-Acetyl-4,4,4-trifluoro-2-methylbutyl]-5-chlorothiophene-2-sulfonamide; 5-Chloro-N-[(1S,2R)-4,4,4-trifluoro-1-(1-hydroxy-1-methylethyl)2-methylbutyl]thiophene-2-sulfonamide; 4-Bromo-5-chloro-N-[3,3,3-trifluoro-1-(hydroxymethyl)-2-(trifluoromethyl)propyl]thiophene-2-sulfonamide; 4-Bromo-5-chloro-N-[(1S)-3,3,3-trifluoro-1-(hydroxymethyl)-2-(trifluoromethyl)propyl]thiophene-2-sulfonamide; 5-Chloro4-fluoro-N-[3,3,3-trifluoro-1-(hydroxymethyl)-2-(trifluoromethyl)propyl]thiophene-2-sulfonamide; 5-Bromo-N-[3,3,3-trifluoro-1-(hydroxymethyl)-2-(trifluoromethyl)propyl]thiophene2-sulfonamide; 5-Fluoro-N-[3,3,3-trifluoro-1-(hydroxymethyl)-2-(trifluoromethyl)propyl]thiophene-2-sulfonamide; 5-Bromo-N-[(1S)-3,3,3-trifluoro-1-(hydroxymethyl)-2-(trifluoromethyl)propyl]thiophene-2-sulfonamide; 5-Fluoro-N-[(1S)-3,3,3-trifluoro-1-(hydroxymethyl)-2-(trifluoromethyl)propyl]thiophene-2-sulfonamide; 5-Chloro-N-[4,4,4-trifluoro-1-(hydroxymethyl)-2-(2,2,2-trifluoroethyl)butyl]thiophene-2-sulfonamide; 5-Chloro-N-[(1S)-(4,4,4-trifluoro-1-(hydroxymethyl)-2-(2,2,2-trifluoroethyl)butyl)]thiophene-2-sulfonamide; 4,5-Dichloro-N-[3,3,3-trifluoro-1-(hydroxymethyl)-2-(trifluoromethyl)propyl]thiophene-2-sulfonamide; N-[(1S)-3,3,3-Trifluoro-1-(hydroxymethyl)-2-(trifluoromethyl)propyl]thiophene-3-sulfonamide; 2,5-Dichloro-N-[(1S)-3,3,3-trifluoro-1-(hydroxymethyl)-2-(trifluoromethyl)propyl]thiophene-3-sulfonamide; N-[(1S)-3,3,3-Trifluoro-1-(hydroxymethyl)-2-(trifluoromethyl)propyl]thiophene-2-sulfonamide; 4,5-Dichloro-N-[(1S)-3,3,3-trifluoro-1-(hydroxymethyl)-2-(trifluoromethyl)propyl]thiophene-2-sulfonamide; Thiophene-2-sulfonic acid (3,3,3-trifluoro-1-hydroxymethyl-2-trifluoromethyl-propyl)-amide; Thiophene-3-sulfonic acid (3,3,3-trifluoro-1-hydroxymethyl-2-trifluoromethyl-propyl)-amide; 2,5-Dichloro-Thiophene-3-sulfonic acid (3,3,3-trifluoro-1-hydroxymethyl-2-trifluoromethyl-propyl)-amide; 4,5-Dibromo-N-[3,3,3-trifluoro-1-(hydroxymethyl)-2-(trifluoromethyl)propyl]thiophene-2-sulfonamide; 3-Bromo-5-chloro-N-[3,3,3-trifluoro-1-(hydroxymethyl)-2-

(trifluoromethyl)propyl]thiophene2-sulfonamide; 4-Bromo-2,5-dichloro-N-[3,3,3-trifluoro-1-(hydroxymethyl)-2-(trifluoromethyl)propyl]thiophene-2-sulfonamide; Benzo[b]thiophene-2-sulfonic acid (3,3,3-trifluoro-1-(hydroxymethyl)-2-(trifluoromethyl)propyl)-amide; 5-Chloro-(3,3,3-trifluoro-1-hydroxymethyl-propyl)-thiophene-2-sulfonamide; and 5-Chloro-N-[(1S)-3,3,3-trifluoro-1-[(1R)-1-hydroxyethyl]-2-(trifluoromethyl)propyl]thiophene-2-sulfonamide; or a pharmaceutically acceptable salt, hydrate, or prodrug thereof.

8. The method according to claim 1, which comprises administering about 375 to about 1000 mg of said compound of formula (I).

9. The method according to claim 3, wherein $R_5$ is chlorine, bromine, or fluorine.

10. The method according to claim 1, wherein W is C and Z is $CR_6$.

11. The method according to claim 1, wherein X is S, and W, Y and Z are independently C or $CR_6$, provided that one of W, Y or Z is C.

12. The method according to claim 1, wherein $R_4$ is selected from the group consisting of $(CF_3)_n$lower alkyl, $(CF_3)_n$(substituted lower alkyl), $(CF_3)_n$lower alkyl phenyl, and $(CF_3)_n$lower alkyl(substitutedphenyl) of S-stereochemistry.

13. The method according to claim 1, wherein W is N and X is $NR_7$.

14. The method according to claim 1, which is 5'-Chloro-N-[3,3,3-trifluoro-2-(trifluoromethyl)-1-S-(hydroxymethyl)propyl]thiophene-2'-sulfonamide or a pharmaceutically acceptable salt, hydrate, or prodrug thereof.

15. The method according to claim 1, wherein X is o, and W, Y and Z are independently selected from C and $CR_6$, provided that one of W, Y or Z is C.

16. The method according to claim 1, wherein $R_5$ is halogen, $R_4$ is selected from the group consisting of $(CF_3)_n$lower alkyl, $(CF_3)_n$(substituted lower alkyl), $(CF_3)_n$lower alkyl phenyl, $(CF_3)_n$lower alkyl(substituted phenyl) of S-stereochemistry, and $R_3$, $R_1$ and $R_2$ are all H.

17. The method according to claim 1, wherein T is C(OH)$R_1R_2$, $R_1$, $R_2$, and $R_3$ are H, and $R_4$ is $(F)_n$cycloalkyl.

18. The method according to claim 1, wherein T is C(OH)$R_1R_2$, $R_1$, $R_2$, and $R_3$ are H, and $R_4$ is $(CF_3)_n$alkyl.

19. The method according to claim 1, wherein T is C(OH)$R_1R_2$, $R_1$ is $CH_3$, $R_2$ is H, $R_3$ is H, and $R_4$ is $(CF_3)_n$alkyl.

20. The method according to claim 1, wherein T is CHO, $R_3$ is H, and $R_4$ is $(CF_3)_n$alkyl.

21. The method according to claim 1, wherein T is C(OH)$R_1R_2$, $R_1$, $R_2$ and $R_3$ are H, and $R_4$ is $(CF_3)_2$CH of S-stereochemistry.

22. The method according to claim 1, wherein T is CHO, $R_3$ is H, and $R_4$ is $CH(CH_3)CH_2CF_3$ of S-stereochemistry.

23. The method according to claim 1, wherein T is $C(O)R_8$, $R_3$ is H, $R_4$ is $CH(CH_3)CH_2CF_3$ of S-stereochemistry, and $R_8$ is $CH_3$.

24. The method according to claim 1, wherein T is C(OH)$R_1R_2$, $R_1$, $R_2$ and $R_3$ are H, and $R_4$ is $CH(CH_2CF_3)_2$ of S-stereochemistry.

25. The method according to claim 1, wherein T is C(OH)$R_1R_2$, $R_1$, $R_2$ and $R_3$ are H, and $R_4$ is $CH(CH_3)CH_2CF_3$ of S-stereochemistry.

26. The method according to claim 1, wherein T is C(OH)$R_1R_2$, $R_1$ is $CH_3$, $R_2$ and $R_3$ are H, and $R_4$ is $CH(CF_3)_2$ of S-stereochemistry.

27. The method according to claim 1, wherein T is C(OH)$R_1R_2$, $R_1$, $R_2$ and $R_3$ are H, and $R_4$ is $(F)_n$cycloalkyl.

28. The method according to claim 1, wherein the pharmaceutically acceptable salt of said compound is selected from the group consisting of salts of organic acids, salts of inorganic acids, salts of bases, and mixtures thereof.

29. The method according to claim 28, wherein the salts of organic and inorganic acids are selected from the group consisting of acetic acid, lactic acid, citric acid, tartaric acid, succinic acid, fumaric acid, maleic acid, malonic acid, mandelic acid, malic acid, hydrochloric acid, hydrobromic acid, phosphoric acid, nitric acid, sulfuric acid, methanesulfonic acid, toluenesulfonic acid, and mixtures thereof.

30. The method according to claim 28, wherein the salts of bases are selected from the group consisting of sodium hydroxide, lithium hydroxide and potassium hydroxide, and mixtures thereof.

* * * * *